US009926602B2

(12) United States Patent
Chinnaiyan et al.

(10) Patent No.: US 9,926,602 B2
(45) Date of Patent: Mar. 27, 2018

(54) RECURRENT GENE FUSIONS IN PROSTATE CANCER

(71) Applicant: THE REGENTS OF THE UNIVERSITY OF MICHIGAN, Aann Arbor, MI (US)

(72) Inventors: Arul M. Chinnaiyan, Plymouth, MI (US); Xiaosong Wang, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 14/302,199

(22) Filed: Jun. 11, 2014

(65) Prior Publication Data

US 2014/0364331 A1    Dec. 11, 2014

Related U.S. Application Data

(62) Division of application No. 12/882,533, filed on Sep. 15, 2010.

(60) Provisional application No. 61/243,226, filed on Sep. 17, 2009.

(51) Int. Cl.
*C12Q 1/68* (2018.01)

(52) U.S. Cl.
CPC ..... *C12Q 1/6886* (2013.01); *C12Q 2600/106* (2013.01); *C12Q 2600/118* (2013.01); *C12Q 2600/136* (2013.01); *C12Q 2600/156* (2013.01); *G01N 2800/7028* (2013.01)

(58) Field of Classification Search
None
See application file for complete search history.

(56) References Cited

U.S. PATENT DOCUMENTS

| | | | |
|---|---|---|---|
| 4,109,496 A | 8/1978 | Allemann et al. |
| 4,323,546 A | 4/1982 | Crockford |
| 4,683,195 A | 7/1987 | Mullis et al. |
| 4,683,202 A | 7/1987 | Mullis et al. |
| 4,800,159 A | 1/1989 | Mullis et al. |
| 4,873,191 A | 10/1989 | Wagner et al. |
| 4,965,188 A | 10/1990 | Mullis et al. |
| 4,968,103 A | 11/1990 | McNab et al. |
| 5,130,238 A | 7/1992 | Malek |
| 5,225,326 A | 7/1993 | Bresser |
| 5,270,184 A | 12/1993 | Walker et al. |
| 5,283,174 A | 2/1994 | Arnold, Jr. et al. |
| 5,283,317 A | 2/1994 | Saifer et al. |
| 5,399,491 A | 3/1995 | Kacian et al. |
| 5,455,166 A | 10/1995 | Walker et al. |
| 5,480,784 A | 1/1996 | Kacian et al. |
| 5,545,524 A | 8/1996 | Trent |
| 5,614,396 A | 3/1997 | Bradley et al. |
| 5,631,169 A | 5/1997 | Lakowicz et al. |
| 5,710,029 A | 1/1998 | Ryder et al. |
| 5,776,782 A | 7/1998 | Tsuji |
| 5,814,447 A | 9/1998 | Ishiguro |
| 5,824,518 A | 10/1998 | Kacian et al. |
| 5,854,206 A | 12/1998 | Twardzik et al. |
| 5,856,125 A | 1/1999 | Mavrothalassitis et al. |
| 5,925,517 A | 7/1999 | Tyagi et al. |
| 5,928,862 A | 7/1999 | Morrison et al. |
| 6,034,218 A | 3/2000 | Reed et al. |
| 6,043,033 A | 3/2000 | Bandman et al. |
| 6,080,912 A | 6/2000 | Bremel et al. |
| 6,121,489 A | 9/2000 | Dorner |
| 6,150,097 A | 11/2000 | Tyagi et al. |
| 6,166,194 A | 12/2000 | Wong |
| 6,198,107 B1 | 3/2001 | Seville et al. |
| 6,262,245 B1 | 7/2001 | Xu et al. |
| 6,303,305 B1 | 10/2001 | Wittwer et al. |
| 6,350,448 B1 | 2/2002 | Bandman et al. |
| 6,395,278 B1 | 5/2002 | Xu et al. |
| 6,444,419 B1 | 9/2002 | Wong |
| 6,534,274 B2 | 3/2003 | Becker et al. |
| 6,541,205 B1 | 4/2003 | Yokoyama et al. |
| 6,573,043 B1 | 6/2003 | Cohen |
| 6,828,429 B1 | 12/2004 | Srivastava et al. |
| 6,872,811 B1 | 3/2005 | MacBeth et al. |
| 6,902,892 B1 | 6/2005 | Salceda et al. |
| 7,008,765 B1 | 3/2006 | Bussemakers et al. |
| 7,037,667 B1 | 5/2006 | Afar et al. |
| 7,125,969 B1 | 10/2006 | Benz et al. |
| 7,138,235 B2 | 11/2006 | Bussemakers et al. |
| 7,199,137 B2 | 4/2007 | Dean |
| 7,229,774 B2 | 6/2007 | Chinnaiyan |
| 7,374,885 B2 | 5/2008 | Becker et al. |
| 7,638,278 B2 | 12/2009 | Pollack |
| 7,718,369 B2 | 5/2010 | Tomlins et al. |
| 2002/0119531 A1 | 8/2002 | Bandman et al. |
| 2002/0182586 A1 | 12/2002 | Morris |
| 2002/0183251 A1 | 12/2002 | Xu et al. |
| 2003/0103981 A1 | 6/2003 | Spancake et al. |
| 2003/0108963 A1 | 6/2003 | Schlegel et al. |
| 2003/0170625 A1 | 9/2003 | Rosenthal et al. |
| 2003/0175736 A1 | 9/2003 | Chinnaiyan et al. |
| 2003/0185830 A1 | 10/2003 | Xu et al. |

(Continued)

FOREIGN PATENT DOCUMENTS

| | | |
|---|---|---|
| EP | 0684315 | 6/2002 |
| EP | 1409727 | 4/2004 |
| WO | 1994010300 | 5/1994 |
| WO | 1998015837 | 4/1998 |
| WO | 98045420 | 10/1998 |

(Continued)

OTHER PUBLICATIONS

Kumar-Sinha (Cancer Discovery 2012 vol. 2 p. 582).*
Ciampi et al. (The Jorunal of Clinical Investigation 2005 vol. 115 p. 94).*
Singh et al. (Cancer Letters 2008 vol. 259 p. 28).*
Gao et al. (PNAS 2006 vol. 103 p. 14477).*

(Continued)

*Primary Examiner* — Katherine D Salmon
(74) *Attorney, Agent, or Firm* — Casimir Jones, S.C.

(57) ABSTRACT

The present invention relates to compositions and methods for cancer diagnosis, research and therapy, including but not limited to, cancer markers. In particular, the present invention relates to recurrent gene fusions as diagnostic markers and clinical targets for prostate cancer.

26 Claims, 30 Drawing Sheets

(56) References Cited

U.S. PATENT DOCUMENTS

| | | |
|---|---|---|
| 2004/0009481 A1 | 1/2004 | Schlegel et al. |
| 2004/0259086 A1 | 12/2004 | Schlegel et al. |
| 2005/0009086 A1 | 1/2005 | Salceda et al. |
| 2005/0042638 A1 | 2/2005 | Arnold, Jr. et al. |
| 2005/0112711 A1 | 5/2005 | Romano et al. |
| 2005/0164223 A1 | 7/2005 | Schalken et al. |
| 2005/0214309 A1 | 9/2005 | Hinrichs et al. |
| 2006/0019256 A1 | 1/2006 | Clarke et al. |
| 2006/0046265 A1 | 3/2006 | Becker et al. |
| 2006/0068425 A1 | 3/2006 | Monahan |
| 2006/0115821 A1 | 6/2006 | Einstein |
| 2006/0275794 A1 | 12/2006 | Carrino et al. |
| 2007/0042381 A1 | 2/2007 | Bentwich et al. |
| 2007/0212702 A1 | 9/2007 | Tomlins et al. |
| 2008/0269157 A1 | 10/2008 | Srivastava et al. |
| 2009/0170075 A1 | 7/2009 | Petrovics et al. |
| 2009/0208937 A1 | 8/2009 | Chinnaiyan |
| 2009/0239221 A1 | 9/2009 | Chinnaiyan et al. |
| 2010/0063088 A1 | 3/2010 | Wood |
| 2010/0305188 A1 | 12/2010 | Nakano |
| 2011/0065113 A1 | 3/2011 | Chinnaiyan et al. |
| 2013/0040858 A1 | 2/2013 | Tomlins et al. |
| 2016/0097104 A1 | 4/2016 | Tomlins et al. |
| 2016/0319369 A1 | 11/2016 | Tomlins et al. |

FOREIGN PATENT DOCUMENTS

| | | |
|---|---|---|
| WO | 9962942 | 12/1999 |
| WO | 9965929 | 12/1999 |
| WO | 0000605 | 1/2000 |
| WO | 0004149 | 1/2000 |
| WO | 0012758 | 3/2000 |
| WO | 0018961 | 4/2000 |
| WO | 0023111 | 4/2000 |
| WO | 0065067 | 11/2000 |
| WO | 0070092 | 11/2000 |
| WO | 0153836 | 7/2001 |
| WO | 0157058 | 8/2001 |
| WO | 0160860 | 8/2001 |
| WO | 0188124 | 11/2001 |
| WO | 2002010443 | 2/2002 |
| WO | 03009814 | 2/2003 |
| WO | 2003011888 | 2/2003 |
| WO | 20003053223 | 7/2003 |
| WO | 2004070056 | 2/2004 |
| WO | 2004023973 | 3/2004 |
| WO | 04074320 | 9/2004 |
| WO | 04092397 | 10/2004 |
| WO | 04097358 | 11/2004 |
| WO | 04113571 | 12/2004 |
| WO | 2005007090 | 1/2005 |
| WO | 2005007830 | 1/2005 |
| WO | 05003387 | 3/2005 |
| WO | 2005113816 | 12/2005 |
| WO | 2006028655 | 3/2006 |
| WO | 2007033187 | 3/2007 |
| WO | 2009009432 | 1/2009 |
| WO | 2010096660 | 8/2010 |

OTHER PUBLICATIONS

Sotiriou, et al., "Breast cancer classification and prognosis based on gene expression profiles from a population-based study", PNAS Sep. 2, 2003, 100(18):10393-10398.

Specht et al., "Quantitative Gene Expression Analysis in Microdissected Archival Formalin-Fixed and Paraffin-Embedded Tumor Tissue." Am J. Pathol. 2001, 158:419-29.

Sramkoski, R.M. et al., "A New Human Prostate Carcinoma Cell Line 22RV1." In Vitro Cell Dev Biol Anim (1999) 35:403-9.

Sridhar et al., "Raf kinase as a target for anticancer therapeutics," Mol Cancer Ther 2005; 4(4): 677-85.

Stauffer et al., "Digital Expression profiles of human endogenous retroviral families in normal and cancerous tissues," Cancer Immunity 2004, 4:2.

Stavenhagen & Robins, "An Ancient Provirus Has Imposed Androgen Regulation on the Adjacent Mouse Sex-Limited Protein Gene", Cell Oct. 21, 1988; 55(2):247-254.

Stenman, "Tumor-associated Trypsin Inhibitor." Clin Chem (2002) 48:1206-9.

Stergianou et al., "Fusion of NUP214 to ABL1 on amplified episomes in T-ALL—implications for treatment," Leukemia 2005, 19:1680-1681.

Strausberg et al., "The cancer genome anatomy project: building an annotated gene index." Trends Genet. Mar. 2000;16(3):103-6.

Strefford, "The use of multicolor fluorescence technologies in the characterization of prostate carcinoma cell lines: a comparison of multiplex fluorescence in situ hybridization and spectral karyotyping data" Cancer Genetics and Cytogenetics 2001; 124:112-121.

Su et al., "Molecular Classification of Human Carcinomas by Use of Gene Expression Signatures." Cancer Res 2001; 61:7388-93.

Sumerdon et al., "An Optimized Antibody-Chelator Conjugate for Imaging of Carcinoembryonic Antigen with Indium-111," Nucl Med Biol 1990; 17:247-254.

Sun et al., "TMPRSS2-ERG fusion, a common genomic alteration in prostate cancer activates C-MYC and prostate epithelial differentiation." Oncogene Jun. 9, 2008, 27(40):5348-5353.

Suzukawa, Kazumi, et al., "Identification of a Breakpoint Cluster Region 3' of the Ribophorin I Gene at 3q21 Associated With the Transcriptional Activation of the EVil Gene in Actue Myelogenous Leukemias With inv(3) (q21q26)", Blood, vol. 84, No. 8, Oct. 15, 1994, pp. 2681-2688.

Swiss Protein Acc. No. P11308.2, RecName: Full=Transcriptional regulator ERG; AltName: Full=Transforming protein ERG, 6 pages, Mar. 6, 2013.

Szabo et al., "Surface plasmon resonance and its use in biomolecular interaction analysis (BIA)." Curr Opin Struct Biol. Oct. 1995;5(5):699-705.

Takaha, Natsuki, et al., "High Mobility Group Protein 1(Y): A Candidate Architectural protein for Chromosomal Rearrangements in Prostate Cancer Cells", Cancer Research Feb. 1, 2002; 62:647-651.

Thalmann, George N., "Androgen-independent Cancer Progression and Bone Metastasis in the LNCaP Model of Human Prostate Cancer", Cancer Research May 15, 1994, 54: 2577-2581.

Tian et al., "The role of the Wnt-signaling antagonist DKK1 in the development of osteolytic lesions in multiple myeloma", The New England Journal of Medicine Dec. 25, 2003; 349(26):2483-2494.

Tognon et al., "Expression of the ETV6-NTRK3 gene fusion as a primary event in human secretory breast carcinoma" Cancer Cell (Nov. 2002); 2(5):367-376.

Tomlins et al., "Whole Transcriptome Amplification for Gene Expression Profiling and Development of Molecular Archives." Neoplasia (2006) 8:153-62.

Tomlins et al., "Distinct classes of chromosomal rearrangements create oncogenic ETS gene fusions in prostate cancer," Nature, Aug. 2, 2007, 448:595-599.

Tomlins, et al., "Recurrent Fusion of TMPRSS2 and ETS Transcription Factor Genes in Postate Cancer" Science Oct. 28, 2005; 310(5748):644-648.

Tomlins et al., "TMPRSS2: ETV4 Gene Fusions Define a Third Molecular Subtype of Prostate Cancer", Cancer Research Apr. 1, 2006; 66:(7):3396-3400.

Tomlins et al., "Integrative Biology of Prostate Cancer Progression", Annual Review of pathology: Mechanisms of Disease 2006; 1:243-271.

Tomlins et al., "Integrative molecular concept modeling of prostate cancer progression" Nature Genetics, Jan. 2007, 39(1):41-51.

Tusher et al., "Significance analysis of microarrays applied to the ionizing radiation response," PNAS Apr. 24, 2001; 98(9): 5116-5121.

Tuzun et al., "Fine-scale structural variation of the human genome" Nat Genet. Jul. 2005; 37(7):727-32.

U.S. Office Action dated Feb. 23, 2009 (Feb. 23, 2009), U.S. Appl. No. 11/519,397, filed Sep. 12, 2006 (Sep. 12, 2006) 50 Pages.

(56) References Cited

OTHER PUBLICATIONS

U.S. Final Office Action dated Aug. 13, 2009 (Aug. 13, 2009), U.S. Appl. No. 11/519,397; filed Sep. 12, 2006 (Sep. 12, 2006) 36 Pages.
U.S. Office Action dated Feb. 1, 2011 (Feb. 1, 2011), U.S. Appl. No. 11/825,552, filed Jul. 6, 2007 (Jul. 6, 2007) Publication No. 2009-0208937 (20 Pages).
U.S. Office Action dated May 26, 2010 (May 26, 2010), U.S. Appl. No. 11/825,552, filed Jul. 6, 2007 (Jul. 6, 2007); Publication No. 2009-0208937 (61 Pages).
U.S. Office Action dated Sep. 29, 2010 (Sep. 29, 2010), U.S. Appl. No. 12/272,865, filed Nov. 18, 2008 (Nov. 18, 2008) 20 Pages.
UniProtKB/Swiss-Prot: P43268.3, RecName: Full=ETS translocation variant 4; AltName: Full=Adenovirus E1A enhancer-binding protein; AltName: Full=E1A-F; AltName: Full=Polyomavirus enhancer activator 3 homolog; Short=Protein PEA3, 6 pages, Mar. 6, 2013.
U.S. Final Office Action dated Jun. 22, 2011, U.S. Appl. No. 12/272,865.
U.S. Final Office Action dated Aug. 23, 2011, U.S. Appl. No. 11/825,552, 42 Pages.
Vaarala, et al. "The TMPRSS2 Gene Encoding Transmembrane Serine Protease is Overexpressed in a Majority of Prostate Cancer Patients: Detection of Mutated TMPRSS2 Form in a Case of Aggressive Disease." International Journal of Cancer, (2001) 94:705-710.
Van Bokhoven, Adrie, et al., "Spectral Karyotype (SKY) Analysis of Human Prostate Carcinoma Cell Lines", The Prostate 2003, 57:226-244.
Vanaja et al., "Transcriptional Silencing of Zinc Finger Protein 185 Identified by expression Profiling is Associated with Prostate Cancer Progression." Cancer Res 2003; 63:3877-82.
Vandesompele et al., "Accurate normalization of real-time quantitative RT-PCR data by geometric averaging of multiple internal control genes." Genome Biol 2002; 3 Research 0034.1-0034.11.
Varambally et al., "Integrative genomic and proteomic analysis of prostate cancer reveals signatures of metastatic progression." Cancer Cell Nov. 2005, 8:393-406.
Vasselli et al., "Predicting survival in patients with metastatic kidney cancer by gene-expression profiling in the primary tumor", PNAS, vol. 100, No. 12, Jun. 10, 2003, pp. 6858-6963.
Velasco et al., "Identification and validation of novel androgen-regulated genes in prostate cancer" Endocrinology 2004,145(8): 3913-3924.
Volik et al., "End-sequence profiling: sequence-based analysis of aberrant genomes." Proc Natl Acad Sci U S A. Jun. 24, 2003;100(13):7696-701.
Walker G. et al., (1992), "Isothermal in vitro amplification of DNA by a restriction enzyme/DNA polymerase system," Proc Natl Acad Sci USA, 89: 392-396.
Walker Michael G. et al., "Prediction of gene function by genome-scale expression analysis: Prostate cancer-associated genes" Genome Research, Dec. 1, 1999, 9:1198-1203.
Wallace, James C. et al., "High-density rhesus macaque Oligonucleotide Microarray design using early-stage rhesus genome sequence information and human genome annotations." BMC Genomics (Jan. 2007) 8:28.
Wan et al., "Mechanism of activation of the RAF-ERK signaling pathway by oncogenic mutations of B-RAF." Cell Mar. 19, 2004; 116(6):855-67.
Wang et al., "An integrative approach to reveal driver gene fusions from paired-end sequencing data in cancer." Nat. Biotechnol. Nov. 2009;27(11):1005-1011.
Wang et al., "BRAF mutations in colon cancer are not likely attributable to defective DNA mismatch repair." Cancer Res. Sep. 1, 2003;63(17):5209-12.
GenBank: M30829.1, Human bcr/abl fusion protein mRNA, partial cds, clone K28, 1 page, Feb. 14, 1996.
GenBank: U75329.1, Human serine protease mRNA, complete cds, 2 pages, Oct. 10, 1997.
Gibas, "A high-resolution study of chromosome changes in a human prostatic carcinoma cell line (LNCaP)." Cancer Genet Cytogenet. Apr. 1984; 11(4):399-404.
Glinsky et al., "Gene expression profiling predicts clinical outcome of prostate cancer." J Clin Invest (2004) 113:913-23.
Golub, et al., "Molecular classification of cancer: class discovery and class prediction by gene expression monitoring." Science. Oct. 15, 1999; 286(5439):531-7.
Goodsell, "The molecular perspective: the ras oncogene." Oncologist. 1999; 4(3):263-4.
Graff et al., "Increased AKT activity contributes to prostate cancer progression by dramatically accelerating prostate tumor growth and diminishing p27Kip1 expression." J Biol Chem. Aug. 11, 2000; 275(32):24500-5.
Graux et al., "Fusion of NUP214 to ABL1 on amplified episomes in T-cell acute lymphoblastic leukemia." Nat Genet. Oct. 2004; 36(10):1084-9.
Greene et al., "Human pancreatic secretory trypsin inhibitor." Methods Enzymol. 1976; 45:813-25.
Greenman et al., "Patterns of somatic mutation in human cancer genomes." Nature. Mar. 8, 2007; 446(7132):153-8.
Griffin et al., "Initial clinical study of indium-111-labeled clone 110 anticarcinoembryonic antigen antibody in patients with colorectal cancer." J Clin Oncol. Apr. 1991; 9(4):631-40.
Groskopf et al., "APTIMA PCA3 Molecular Urine Test: Development of a Method to Aid in the Diagnosis of Prostate Cancer." Clin Chem 2006 52:1089-95.
Guasch et al., "Endogenous retroviral sequence is fused to FGFR1 kinase in the 8p12 stem-cell myeloproliferative disorder with t(8;19)(p12;q13.3)." Blood. Jan. 1, 2003; 101(1):286-8.
Guatelli et al., "Isothermal, in vitro amplification of nucleic acids by a multienzyme reaction modeled after retroviral replication," Proc Natl Acad Sci U S A. Oct. 1990; 87(19):7797.
Hahn et al., "Finding fusion genes resulting from chromosome rearrangement by analyzing the expressed sequence databases." Proc Natl Acad Sci U S A. Sep. 7, 2004;101(36):13257-61.
Hampton et al., "A sequence-level map of chromosomal breakpoints in the MCF-7 breast cancer cell line yields insights into the evolution of a cancer genome." Genome Res. Feb. 2009;19(2):167-77.
Han et al., "Long-term biochemical disease-free and cancer-specific survival following anatomic radical retropubic prostatectomy. The 15-year Johns Hopkins experience." Urol Clin North Am. Aug. 2001; 28(3):555-65.
Han et al., "A Fluoresence in Situ Hybridization Screen for E26 Transformation-Specific Aberrations: Identification of DDX5-ETV4 Fusion Protein in Prostate Cancer" Cancer Research Sep. 2008 68(18):7629-7637.
Harbig et al., "A sequence based identification of the genes detected by probesets on the Affymetrix U133 plus 2.0 array." Nucleic Acids Research. Feb. 2005, 33(3): e31.
Harlow and Lane, Antibodies: A Laboratory Manual, Cold Spring Harbor Laboratory (1988).
Hartel, "Characterisation of steroid receptor expression in the human prostate carcinoma cell line 22RV1 and quantification of androgen effects on mRNA regulation of prostate-specific genes." J Steroid Biochem Mol Biol. Oct. 2004,92(3):187-97.
Haverback et al., "Trypsin, Trypsinogen and Trypsin Inhibitor in Human Pancreatic Juice." Am J Med. Sep. 1960; 29:421-33.
Helgeson et al., "Characterization of TMPRSS2:ETV5 and SLC45A3:ETV5 gene fusions in prostate cancer." Cancer Res. Jan. 1, 2008;68(1):73-80.
Hendriksen et al., "Evolution of the Androgen Receptor Pathway during Progression of Prostate Cancer." Cancer Research, (2006) 66(10):5012-5020.
Hermans et al., "Truncated ETV1, Fused to Novel Tissued-Specific Gense, and Full Length ETV1 in Prostate Cancer" Cancer Research, Sep. 2008, 68:7541-7549.
Hermans et al., "TMPRSS2:ERG Fusion by Translocation or Interstitial Deletion is Highly Relevant in Androgen-Dependent Prostate Cancer, But is Bypassed in Late-Stage Androgen Receptor—Negative Prostate Cancer." Cancer Res. Nov. 15, 2006;66(22):10658-63.

(56) References Cited

OTHER PUBLICATIONS

Hessels et al., "DD3PCA3-based Molecular Urine Analysis for the Diagnosis of Prostate Cancer." Eur Urol (2003) 44:8-16.
Hnatowich et al., "The preparation and labeling of DTPA-coupled albumin." Int J Appl Radiat Isot. May 1982;33(5):327-32.
Hoeflich et al., "In vivo antitumor activity of MEK and phosphatidylinositol 3-kinase inhibitors in basal-like breast cancer models." Clin Cancer Res. Jul. 15, 2009;15(14):4649-64.
Hoeller et al., "Targeting the ubiquitin system in cancer therapy," Nature. Mar. 26, 2009;458(7237):438-44.
*Homo sapiens* angiotensin II receptor-associated protein (AGTRAP), transcript variant 2, mRNA, NCBI Reference Sequence: NM_001040194.1, 4 pages, Jan. 6, 2013.
*Homo sapiens* angiotensin II receptor-associated protein (AGTRAP), transcript variant 3, mRNA, NCBI Reference Sequence: NM_001040195.1, 4 pages, Jan. 6, 2013.
*Homo sapiens* angiotensin II receptor-associated protein (AGTRAP), transcript variant 4,mRNA, NCBI Reference Sequence: NM_001040196.1, 4 pages, Jan. 6, 2013.
*Homo sapiens* angiotensin II receptor-associated protein (AGTRAP), transcript variant 5, mRNA, NCBI Reference Sequence: NM_001040197.1, 4 pages, Jan. 6, 2013.
*Homo sapiens* epithelial splicing regulatory protein 1 (ESRP1), transcript variant 1, mRNA NCBI Reference Sequence: NM_017697.3, 5 pages, Dec. 30, 2012.
*Homo sapiens* v-raf murine sarcoma viral oncogene homolog B (BRAF), Mrna NCBI Reference Sequence: NM_004333.4, 6 pages, Oct. 28, 2013.
*Homo sapiens* v-raf murine sarcoma viral oncogene homolog B1 (BRAF), RefSeqGene on chromosome 7, NCBI Reference Sequence: NG_007873.2, 31 pages, Feb. 3, 2013.
*Homo sapiens* v-raf-1 murine leukemia viral oncogene homolog 1 (RAF1), mRNA NCBI Reference Sequence: NM_002880.3, 8 pages, Jan. 28, 2013.
*Homo sapiens* v-raf-1 murine leukemia viral oncogene homolog 1 (RAF1), RefSeqGene (LRG_413) on chromosome 3 NCNI Reference Sequence: NG_007467.1, 24 pages, Feb. 18, 2013.
Hoshikawa et al., "Hypoxia induces different genes in the lungs of rats compared with mice." Physiol. Genomics 2003, 12:209-219.
Huang et al., "Gene expression predictors of breast cancer outcomes", The Lancet May 10, 2003, 361:1590-1596.
Huang et al., "Whole genome DNA copy number changes identified by high density oligonucleotide arrays." Hum Genomics. May 2004;1(4):287-99.
Hull et al., G.W. et al., "Cancer Control with Radical Prostatectomy Alone in 1,000 Consecutive Patients." J. Urol (2002) 167:528-34.
Iftikhar et al., "Disease-and cell-specific expression of GP73 in human liver disease." Am. J Gastrenterology 2004, 99(6):1087-1095.
Ikawa et al., "B-raf, a new member of the raf family, is activated by DNA rearrangement" Mol Cell Biol. Jun. 1988; 8(6):2651-4.
Iljin, et al. "TMPRSS2 fusions with oncogenic ETS factors in prostate cancer involve unbalanced genomic rearrangements and are associated with HDAC1 and epigenetic reprogramming." Cancer Res. Nov. 1, 2006; 66(21):10242-6.
Illum & Jones, "Attachment of monoclonal antibodies to microspheres." Methods Enzymol. 1985; 112:67-84.
In situ hybridization : medical applications, Edited by G.R. Coulton and J. de Belleroche. Kluwer Academic Publishers, Boston 1992.
In situ hybridization in neurobiology:advances in methodology. Edited by Eberwine, Valentino, Barchas. Oxford University Press Inc., England 1994.
In Situ Hybridization: A Practical Approach. Edited by D. G. Wilkinson. Oxford University Press, USA, 1992.
Perner Sven et al., "TMPRSS2-ERG fusion prostate cancer: an early molecular event associated with invasion," The American Journal of Surgical Pathology, Jun. 2007. 31(6):882-888.
Perner et al., "TMPRSS2:ERG Fusion-Associated Deletions Provide Insight into the Heterogeneity of Prostate Cancer." Cancer Res (2006); 66(17):8337-8341.

Persing, David H. "In Vitro Nucleic Acid Amplification Techniques" Diagnostic Medical Microbiology: In Principles and Applications (Persing, David H. ed.) 1993, 51-87.
Petrovics et al. "Frequent overexpression of ETS-related gene-1 (ERG1) in prostate cancer transcriptome." Oncogene (2005); 24:3847-3852.
Pettus et al., "Multiple abnormalities detected by dye reversal genomic microarrays in prostate cancer: A much greater sensitivity than conventional cytogenetics." Cancer Genet. Cytogent. 2004, 154(2):110-118.
Pflueger Dorothee et al., "N-MYC Downstream Regulated Gene 1 (NDRG1) is fused to ERG in Prostate Cancer." Neoplasia (Aug. 2009) 11(8):804.
Pratilas et al., "(V600E)BRAF is associated with disabled feedback inhibition of RAF-MEK signaling and elevated transcriptional output of the pathway." Proc Natl Acad Sci U S A. Mar. 17, 2009; 106(11):4519-24.
Rabbitts, "Chromosomal translocations in human cancer", Nature Nov. 10, 1994; 372:143-149.
RAF Family Antibody Sampler Kit #2330, Cell Signaling Technology, downloaded from: http://www.cellsignal.com/products/2330.html on May 16, 2013.
Rao et al., "erg, a Human ets-Related Gene on Chromosome 21: Alternative Splicing, Polyadenylation, and Translation." Science (1987), 237(4815):635-639.
Reddy et al., "The erg gene: A human gene related to the ets oncogene." Proc. Natl. Acad. Sci. (1987) 84:6131-6135.
Rhodes et al., "Large-scale meta-analysis of cancer microarray data identifies common transcriptional profiles of neoplastic transformation and progression" Proc Natl Acad Sci USA (2004) 101:9309.
Rhodes, et al., "ONCOMINE: A cancer microarray database and integrated data-mining platform", Neoplasia, vol. 6, No. 1, Jan./Feb. 2004, pp. 1-6.
Rickman et al., "SLC45A3-ELK4 is a novel and frequent erythroblast transformation-specific fusion transcript in prostate cancer," Cancer Research 2009; 69:2734-2738.
Rikova et al., "Global survey of phosphotyrosine signaling identifies oncogenic kinases in lung cancer." Cell. Dec. 14, 2007; 131(6):1190-203.
Rodriguez-Viciana et al, "Cancer targets in the Ras pathway," Cold Spring Harb Symp Quant Biol 2005, 70:461-467.
Rosenwald et al. "The proliferation gene expression signature is a quantitative integrator of oncogenic events that predicts survival in mantle cell lymphoma," Cancer Cell. Feb. 2003, 3:185-197.
Rowley, "A new Consistent Chromosomal Abnormality in Chronic Myelogenous Leukaemia Identified by Quinacrine Fluorescence and Giemsa Staining" Nature Jun. 1, 1973; 243:290-293.
Rowley, "Chromosome translocations: dangerous liaisons revisited", Nature Reviews, Cancer Dec. 2001; 1:245-250.
Ruan et al., "Fusion transcripts and transcribed retrotransposed loci discovered through comprehensive transcriptome analysis using Paired-End diTags (PETs)." Genome Res. Jun. 2007;17(6):828-38.
Rubin and Chinnaiyan. "Bioinformatics approach leads to the discovery of the TMPRSS2:ETS gene fusion in prostate cancer." Laboratory Investigation 2006; 86:1099-1102.
Rubin et al., "Methylacyl Coenzyme A Racemase as a Tissue Biomarker for Prostate Cancer." JAMA (2002) 287:1662-70.
Rubin et al., "Rapid ("warm") autopsy study for procurement of metastatic prostate cancer." Clin Cancer Res. Mar. 2000;6(3):1038-45.
Rubin et al., "Overexpression, amplification, and androgen regulation of TPD52 in prostate cancer", Cancer Research, Jun. 1, 2004, 64:3814-3822.
Sala et al., "BRAF silencing by short hairpin RNA or chemical blockade by PLX4032 leads to different responses in melanoma and thyroid carcinoma cells." Mol Cancer Res. May 2008; 6(5):751-9.
Schalken, "Molecular Diagnostics and Therapy of Prostate Cancer: New Avenues." Eur. Urol 1998 34 (Suppl.3):3-6.
Scheinberg et al., "Tumor imaging with radioactive metal chelates conjugated to monoclonal antibodies." Science. Mar. 19, 1982; 215(4539):1511-3.
Schmidt et al., "Quantitative Multi-Gene Expression Profiling of Primary Prostate Cancer." The Prostate 66:1521-1534.

(56) References Cited

OTHER PUBLICATIONS

Schroeder (2007) European Urology 2247-1-4 Comments on Attard et al. (2007), "Duplication of the Fusion of TMPRSS2 to ERG sequences identifies Fatal Human Prostate Cancer", Onogene 2007; 1-11.
Schubbert et al., "Hyperactive Ras in developmental disorders and cancer," Nat Rev Cancer 7, 295-308, (2007).
Schwartz, et al., "Gene expression in ovarian cancer reflects both morphology and biological behavior, distinguishing clear cell from other poor-prognosis ovarian carcinomas", Cancer Research 62, Aug. 15, 2002, pp. 4722-4729.
Seeburg et al, "Biological properties of human c-Ha-ras1 genes mutated at codon 12," Nature 1984, 312:71-75.
Seton-Rodgers, "Breast cancer: A striking resemblance" Nature Reviews Sep. 2007; 7:638.
Shadeo & Lam. "Comprehensive copy number profiles of breast cancer cell model genomes." Breast Cancer Res. 2006;8(1):R9.
Shi et al., "Molecular Alterations Associated With LNCaP Cell Progression to Androgen Indpendence", The Prostate 2004, 60:257-271.
Shimizu et al., "Structure of the activated c-raf-1 gene from human stomach cancer," Oncogenes and Cancer 1986, 17: 85-91.
Shtivelman et al., "Fused transcript of abl and bcr genes in chronic myelogenous leukaemia." Nature. Jun. 13-19, 1985; 315(6020):550-4.
Singh et al., "Annotation of androgen dependence to human prostate cancer associated genes by microarray analysis of mouse prostate" Cancer Letters 2006, 237:298-304.
Singh et al., "RNA Reference mediated silencing of SPINK reduces invasion and proliferation of prostate cancer cells." Proceedings of the Annual Meeting of the American Association for Cancer Research, (Apr. 2006) 47(1):823.
Sithanandam et al, "Complete coding sequence of a human B-raf cDNA and detection of B-raf protein kinase with isozyme specific antibodies," ONCOGENE 1990; 5(12): 1775-80.
Sithanandam et al., "B-raf and a B-raf pseudogene are located on 7q in man," ONCOGENE 1992, 7(4): 795-9.
Sjolander et al., "Integrated fluid handling system for biomolecular interaction analysis." Anal Chem. Oct. 15, 1991;63(20):2338-45.
Slamon et al., "Use of chemotherapy plus a monoclonal antibody against HER2 for metastatic breast cancer that overexpresses HER2." N Engl J Med. Mar. 15, 2001;344(11):783-92.
Slamon, et al., "Human breast cancer: correlation of relapse and survival with amplification of the HER-2/neu oncogene", Science Jan. 9, 1987; 235(4785):177-182.
Smith et al., "Cloning, expression, and characterization of a soluble calcium-activated nucleotidase, a human enzyme belonging to a new family of extracellular nucleotidases." Arch Biochem Biophys. Oct. 1, 2002; 406(1):105-15.
Smith et al., "Expression profiling of EWS/FLI identifies NKX2.2 as a critical target gene in Ewing's sarcoma" Cancer Cell May 2006, 9:405-416.
Soda et al., "Identification of the transforming EML4-ALK fusion gene in non-small-cell lung cancer." Nature. Aug. 2, 2007;448(7153):561-6.
Solakidi et al., "Co-expression of trypsin and tumour-associated trypsin inhibitor (TATI) in colorectal adenocarcinomas." Histology and Histopathology 2003, 18(4):1181-1188.
Sollar et al., "Confirmation of the High Frequency of the TMPRSS2/ERG Fusion Gene in Prostate Cancer", Genes, Chromosomes & Cancer 2006, 45:717-719.
Sorenson et al., "A Second Ewing's sarcoma translocation, t (21; 22), fuses the EWS gene to another ETS-family transcription factor, ERG." Nature Genetics 1994, 6(2):146-151.
International Search Report dated May 20, 2011 Application No. PCT/US2010/048915; 13 Pages.
International Search Report dated Apr. 15, 2009 (Apr. 15, 2009); Application No. PCT/US2008/069204; Filing Date: Jul. 3, 2008 (Jul. 3, 2008); WIPO Publication No. WO 2009/009432 (8 Pages).
International Search Report dated Dec. 4, 2007 (Dec. 4, 2007), Application No. PCT/US2006/035507; Filing Date: Sep. 12, 2006 (Sep. 12, 2006); WIPO Publication No. WO 2007/033187 (5 Pages).
International Search Report dated Jan. 30, 2009 (Jan. 30, 2009), Application No. PCT/2008/069201; Filing Date: Jul. 3, 2008 (Jul. 3, 2008); WIPO Publication No. WO 2009/009431 (5 Pages).
International Search Report dated Jul. 28, 2009 (Jul. 28, 2009); Application No. PCT/US2007/084090; Filing Date: Nov. 8, 2007 (Nov. 8, 2007) WIPO Publication No. WO 2008/058239 (5 Pages).
International Search Report dated May 25, 2010 (May 25, 2010), Application No. PCT/US2009/064957; Filing Date: Nov. 18, 2009 (Nov. 18, 2009) WIPO Publication No. WO 2010/059702 (9 Pages).
International Search Report dated Nov. 5, 2010 (Nov. 5, 2010); Application No. PCT/US2010/020501; Filing Date: Jan. 8, 2010 (Jan. 8, 2010); WIPO Publication No. WO 2010/081001 (9 Pages).
Iwabuchi et al, "Use of the two-hybrid system to identify the domain of p53 involved in oligomerization," OCOGENE 8: 1693-1696 (1993).
Jacquinet, et al. "Cloning and characterization of the cDNA and gene for human epitheliasin." European Journal of Biochemistry (2001); 268: 2687-2699.
Jain et al., "Expression profiles provide insights into early malignant potential and skeletal abnormalities in multiple endocrine neoplasia type 2B syndrome tumors." Cancer Res. Jun. 1, 2004;64(11):3907-13.
Janknecht, "Analysis of the ERK-stimulated ETS transcription factor ER81." Mol Cell Biol. Apr. 1996; 16(4):1550-6.
Jarrard et al., "Deletional, mutational, and methylation analyses of CDKN2 (p16/MTS1) in primary and metastatic prostate cancer." Genes Chromosomes Cancer Jun. 1997; 19(2):90-6.
Jayaraman et al., "p300/cAMP-responsive Element-binding Protein Interactions with Ets-1 and Ets-2 in the Transcriptional Activation of the Human Stromelysin Promoter." J Biol Chem 1999, 274:17342-17352.
Jeon In-Sang et al., "A variant Ewing's sarcoma translocation (7;22) fuses the EWS gene to the ETS gene ETV1." Oncogene 1995, 10(6):1229-1234.
Jeong et al., "BRAF activation initiates but does not maintain invasive prostate adenocarcinoma." PLoS One. 2008; 3(12):e3949.
Johansson et al., "Natural History of Early, Localized Prostate Cancer." JAMA (2004) 291: 2713-9.
Jones, D.T. et al., "Tandem duplication producing a novel oncogenic BRAF fusion gene defines the majority of pilocytic astrocytomas." Cancer Research 2008 68(21):8673-8677.
Joosten et al., "The production of antibody fragments and anitbody fusion proteins by yeasts and filamentous fungi." Microbial Cell Factories 2003, 2:1-15.
Kalos et al., "Prostein expression is highly restricted to normal and malignant prostate tissues." Prostate. Aug. 1, 2004; 60(3):246-56.
Kamnasaran et al., "Rearrangment in the PITX2 and MIPOL1 genes in a patient with a t(4;14) chromosome." European Journal of Human Genetics, Apr. 2003, 11(4):315-324.
Karnoub et al., "Ras oncogenes: split personalities." Nat Rev Mol Cell Biol. Jul. 2008; 9(7):517-31.
Karolchik et al., "The UCSC Table Browser data retrieval tool." Nucleic Acids Res. Jan. 1, 2004;32(Database issue): D493-6.
Kato et al., "Activation of Holliday junction-recognizing protein involved in the chromosomal stability and immortality of cancer cells." Cancer Res. Sep. 15, 2007;67(18):8544-53.
Kattan et al., "Postoperative Nomogram for Disease Recurrence After Radical Prostatectomy for Prostate Cancer." J. Clinical Oncol. (1999) 17:1499-507.
Kattan et al., "The Addition of Interleukin-6 Soluble Receptor and Transforming Growth Factor Beta1 Improves a Preoperative Nomogram for Predicting Biochemical Progression in Patients with Clinically Localized Prostate Cancer." J Clin Oncol (2003) 21:3537-9.
Kazal et al., "Isolation of a Crystalline Trypsin Inhibitor-Anticoagulant Protein from Pancreas." Journal of the American Chemical Society (1948) 70:3034-3040.

(56) References Cited

OTHER PUBLICATIONS

Keats, et al., "Overexpression of transcripts originating from the MMSET locus characterizes all (t;14)(p16;q32)-positive multiple myeloma patients", Blood, vol. 105, No. 10, May 15, 2005, pp. 4060-4069.
Khaw et al., "Myocardial infarct imaging of antibodies to canine cardiac myosin with indium-111-diethylenetriamine pentaacetic acid." Science. Jul. 11, 1980; 209(4453):295-7.
Kim et al., "Cooperativity of Nkx3.1 and Pten loss of function in a mouse model of prostate carcinogenesis" Proc Natl Acad Sci U S A. Mar. 5, 2002; 99(5):2884-9.
Kladney et al., "GP73, a novel Golgi-localized protein upregulated by viral infection." Gene 2000 249:53-65.
Klinger et al., "Rapid detection of chromosome aneuploidies in uncultured amniocytes by using fluorescence in situ hybridization (FISH)." Am J Hum Genet. Jul. 1992;51(1):55-65.
Kohler and Milstein, (1975), "Continuous cultures of fused cells secreting antibody of predefined specificity," Nature 256: 495-497.
Koivunen et al, "EML4-ALK fusion gene and efficacy of an ALK kinase inhibitor in lung cancer." Clin Cancer Res. Jul. 1, 2008; 14(13):4275-83.
Kong et al. "Consistent Detection of TLS/FUS-ERG Chimeric Transcripts in Acute Myeloid Leukemia With t(16;21) (p11;q22) and Identification of a Novel Transcript" Blood. Aug. 1, 1997;90(3):1192-9.
Kozbor & Roder "The production of monoclonal antibodies from human lymphocytes." Immunol Today. Mar. 1983; 4(3)12-9.
Kranenburg, "The KRAS oncogene: past, present, and future." Biochim Biophys Acta. Nov. 25, 2005; 1756(2):81-2.
Kumar-Sinha Chandan et al., "Evidence of Recurrent Gene Fusions in Common Epithelial Tumors," Trends in Mol. Medicine, Nov. 2006, 12(11):529-536.
Kumar-Sinha Chandan et al., "Recurrent gene fusions in prostate cancer." Nature reviews, Cancer (Jul. 2008) 8(7):497-511.
Kumar-Sinha et al., "Elevated Methylacyl-CoA Racemase Enzymatic Activity in Prostate Cancer." Am J. Path (2004) 164:787-93.
Kuo et al., "Detection of aneuploidy involving chromosomes 13, 18, or 21, by fluorescence in situ hybridization (FISH) to interphase and metaphase amniocytes." Am. J. Human Genet. 1991, 49:112-119.
Kwoh et al, "Transcription-based amplification system and detection of amplified human immunodeficiency virus type 1 with a bead-based sandwich hybridization format," Proc Natl Acad Sci USA 1989, 86: 1173-1177.
Lapointe et al., "Gene expression profiling identifies clinically relevant subtypes of prostate cancer." Proc Natl Acad Sci U S A. Jan. 20, 2004; 101(13):811-6.
Latulippe et al., "Comprehensive gene expression analysis of prostate cancer reveals distinct transcriptional programs associated with metastatic disease" Cancer Res. Aug. 1, 2002; 62(15):4499-506.
Lauffer "Targeted relaxation enhancement agents for MRI," Magn Reson Med. Dec. 1991; 22(2):339-42.
Laxman et al, "A First-Generation Mulitplex Biomarker Analysis of Urine for the Early Detection of Prostate Cancer." Cancer Res. Feb. 1, 2008; 68(3):645-9.
Laxman et al., "Noninvasive Detection of TMPRSS2:ERG Fusion Transcripts in the Urine of Men with Prostate Cancer," Neoplasia. Oct. 2006; 8(10):885-8.
Li et al, "A neoplastic gene fusion mimics trans-splicing of RNAs in normal human cells," Science. Sep. 5, 2008; 321(5894):1357-61.
Li et al., "PTEN, a putative protein tyrosine phosphatase gene mutated in human brain, breast, and prostate cancer." Science. Mar. 28, 1997; 275(5308):1943-7.
Li Shijun et al., "Application of genomic technologies to human prostate cancer" OMICS A Journal of Integrative Biology (Sep. 2006), 10(3):261-275.
Lin et al., "Prostate-localized and androgen-regulated expression of the membrane-bound serine protease TMPRSS2." Cancer Res. Sep. 1, 1999;59(17):4180-4.

Communi et al., "Cotranscription and intergenic splicing of human P2Y11 and SSF1 genes." J Biol Chem. May 11, 2001;276(19):16561-6.
Cruz et al., "Absence of BRAF and NRAS Mutations in Uveal Melanoma." Cancer Research Oct. 1, 2003, 63:5761-5766.
Database EMBL (Online) Mar. 2, 2007 "140298_1373_0575 3' ESTs from HeLa cell *Homo sapiens* Cdna 3', mRNA sequence." XP002597931 retrieved from EBI accession No. EMBL:EH3299833 Nucleotides 2-11 (X).
Database Entrez Nucleotide (Online) Sep. 21, 2008, "*Homo sapiens* solute carrier family 45, member 3 (SLC45A3), mRNA; version NM_033102.2 GI: 93277086" Accession No. NM033102 nucleotides 1525-1563 (A).
Davies et al, "Mutations of the BRAF gene in human cancer." Nature. Jun. 27, 2002;417(6892):949-54.
De Kok et al., "DD3(PCA3), a very sensitive and specific marker to detect prostate tumors." Cancer Res. May 1, 2002; 62(9):2695-8.
Deininger et al., "The development of imatinib as a therapeutic agent for chronic myeloid leukemia." Blood. Apr. 1, 2005; 105(7):2640-53.
deKlein et al., "A cellular oncogene is translocated to the Philadelphia chromosome in chronic myelocytic leukaemia." Nature. Dec. 23, 1982; 300(5894):765-7.
DeLong et al., "Comparing the Areas Under Two or More Correlated Receiver Operating Characteristic Curves: A Nonparametric Approach." Biometrics (1988) 44:837-45.
Demetri et al., "Efficacy and safety of imatinib mesylate in advanced gastrointestinal stromal tumors." N Engl J Med. Aug. 15, 2002; 347(7):472-80.
Demichelis et al., "TMPRSS2:ERG gene fusion associated with lethal prostate cancer in a watchful waiting cohort." Oncogene. Jul. 5, 2007; 26(31):4596-9.
Der et al, "Transforming genes of human bladder and lung carcinoma cell lines are homologous to the ras genes of Harvey and Kirsten sarcoma viruses." Proc Natl Acad Sci U S A. Jun. 1982; 79(11):3637-40.
Dessars et al., "Chromosomal translocations as a mechanism of BRAF activation in two cases of large congenital melanocytic nevi." J Invest Dermatol. Jun. 2007; 127(6):1468-70.
Dhanasekaran et al., "Delineation of prognostic biomarkers in prostate cancer." Nature 2001, 412:822-6.
Dhanasekaran et al., "Molecular profiling of human prostate tissues: insights into gene expression patterns of prostate development during puberty." FASEB J. Feb. 2005; 19(2):243-5.
Di Cristofano et al., "Pten and p27KIP1 cooperate in prostate cancer tumor suppression in the mouse." Nat Genet. Feb. 2001; 27(2):222-4.
Downward, "Targeting RAS signalling pathways in cancer therapy." Nat Rev Cancer. Jan. 2003; 3(1):11-22.
Druker et al., "Five-year follow-up of patients receiving imatinib for chronic myeloid leukemia." N Engl J Med. Dec. 7, 2006; 355(23):2408-17.
Eisen et al., Cluster analysis and display of genome-wide expression patterns. Proc Natl Acad Sci USA. Dec. 8, 1998; 95(25):14863-8.
Eisenberg & Levanon, "Human housekeeping genes are compact." Trends Genet. Jul. 2003; 19(7):362-5.
EP Search Report dated Jul. 8, 2011; Application No. 06814528.3.
Esgueva, R. et al., "Prevalence of TMPRSS2-ERG and SLC45A3-ERG gene fusions in a large prostatectomy cohort." Modern Pathology 2010 23(4):539-546.
European Office Action dated Jun. 27, 2011, Application No. 07864115.6, 6 Pages.
European Office Action dated Jun. 28, 2011, Application No. 08772418.3, 4 Pages.
European Office Action dated Aug. 17, 2010 (Aug. 17, 2010); Application No. 07864115.6; Filing Date: Nov. 8, 2007 (Nov. 8, 2007) Publication No. 2079851 (9 Pages).
European Office Action dated May 5, 2010 (May 5, 2010), Application No. 08826146.6; Filing Date: Jul. 3, 2008 (Jul. 3, 2008); Publication No. 2171094 (23 Pages).
Faith et al., "Trefoil Factor 3 Overexpression in Prostate Carcinoma: Prognostic Importance Using Tissue Microarrays." Prostate (2004) 61:215-27.

(56) References Cited

OTHER PUBLICATIONS

Ferrando et al., "Gene expression signatures define novel oncogenic pathways in T cell acute lymphoblastic leukemia." Cancer Cell. Feb. 2002; 1(1):75-87.
Ferreira et al, "Array CGH and gene-expression profiling reveals distinct genomic instability patterns associated with DNA repair and cell-cycle checkpoint pathways in Ewing's sarcoma." Oncogene. Mar. 27, 2008; 27(14):2084-90.
Fingleon "Matrix metalloproteinases: roles in cancer and metastasis." Front Biosci. Jan. 1, 2006; 11:479-91.
Fonseca et al., "Genetics and cytogenetics of multiple myeloma: a workshop report."Cancer Res. Feb. 15, 2004; 64(4):1546-58.
Fradet et al., "APTIMA® PCA3 Molecular Urine Test: Development of a Method to aid in the diagnosis of Prostate Cancer" European Urology Supplements 2006, 5(2): 275.
Fradet et al., "UPM3, A new molecular urine test for the detection of Prostate Cancer." Urology 2004, 64:311-6.
Fukayama et al., "immunohistochemical localization of pancreatic secretory trypsin inhibitor in fetal and adult pancreatic and extrapancreatic tissues." J Histochemistry and Cytochemistry. 1986 34(2): 227-235.
Futreal et al., "A census of human cancer genes." Nat Rev Cancer. Mar. 2004; 4(3):177-83.
Garraway et al., "Trefoil Factor 3 is Overexpressed in Human Prostate Cancer." Prostate 2004 61:209-14.
Garraway et al., "Integrative genomic analyses identify MITF as a lineage survival oncogene amplified in malignant melanoma." Nature. Jul. 7, 2005; 436(7047):117-22.
Garte et al., "Inhibition of H-ras oncogene transformation of NIH3T3 cells by protease inhibitors." Cancer Res. Jun. 15, 1987; 47(12):3159-62.
Genbank Accession M17254.1, Human erg2 gene encoding erg2 protein, complete cds, 2 pages, Nov. 8, 1994.
Genbank Accession NM_004449.4, *Homo sapiens* v-ets erythroblastosis virus E26 oncogne homolog (avian) (ERG), transcript variant 2, mRNA, 6 pages, Mar. 24, 2013.
Genbank Accession NM_014685.3, *Homo sapiens* homocysteine-inducible, endoplasmic reticulum stress-inducible, ubiquitin-like domain member 1 (HERPUD1), transcript variant 1, mRNA, 4 pages, Sep. 1, 2013.
Genbank Accession No. NC_000007.11, *Homo sapiens* chromosome 7, complete sequence, 1 page, Oct. 25, 2004.
Genbank Accession No. NM_001986.2, *Homo sapiens* ets variant 4 (ETV4), transcript variant 1, mRNA, 4 pages, Mar. 17, 2013.
Genbank Accession No. NM_004956.4, *Homo sapiens* ets variant 1 (ETV1), transcript variant 1, mRNA, 6 pages, Mar. 24, 2013.
Genbank Accession No. NP_004947.2, ETS translocation variant 1 isoform a [*Homo sapiens*], 5 pages, Mar. 24, 2013.
Genbank Accession No. NT_007819.15, Homo sapiens chromosome 7 genomic contig, 4 pages, Aug. 20, 2004.
Genbank Accession No. NT_086880.1, 3 pages, Aug. 20, 2004.
Genbank Accession No. NT_010783.14, *Homo sapiens* chromosome 17 genomic contig, reference assembly, 3 pages, Feb. 29, 2008.
GenBank: AAC51784.1, serine protease [*Homo sapiens*], 2 pages, Oct. 10, 1997.
GenBank: DQ204772.1, *Homo sapiens* TMPRSS2/ERGa fusion transcript, 1 page, Nov. 2, 2005.
Wang et al., "Identification and characterization of AGTRAP, a human homolog of murine Angiotensin II Receptor-Associated Protein (Agtrap)" Intl. J Biochem. & Cell Biology 2002, 34:93-102.
Wang, et al., "Gene-expression profiles to predict distant metastasis of lymph-node-negative primary breast cancer", The Lancet, vol. 365, No. 9460, Feb. 19-25, 2005, pp. 671-679.
Wang, et al. "Expression of Variant TMPRSS2/ERG Fusion Messenger RNAs is Associated with Aggressive Prostate Cancer," Cancer Res. (2006) pp. 8347-8351, vol. 66: 17.
Wang-Johanning, Feng, et al., "Quantitation of HERV-K env gene expression and splicing in human breast", Onogene(2003)22,pp. 1528-1535.

Ward et al., "Rapid prenatal diagnosis of chromosomal aneuploidies by fluorescence in situ hybridization: clinical experience with 4,500 specimens." Am. J. Hum. Gen. 1993, 52:854-865.
Warzecha et al., "ESRP1 and ESRP2 are epithelial cell-type-specific regulators of FGFR2 splicing." Mol Cell. Mar. 13, 2009; 33(5):591-601.
Watson, Spencer K., et al., "Cytogenetically balanced translocations are associated with focal copy number alterations", Hum Genet (2007); 120:795-805.
Weigle, Bernd, et al., "D-PCa-2: A Novel Transript Highly Overexpressed in Human prostate and Prostate Cancer", International Journal of Cancer, 2004, 109:882-892.
Weir et al., "Characterizing the cancer genome in lung adenocarcinoma." Nature. Dec. 6, 2007;450(7171):893-8.
Weiss, (1991), "Hot prospect for new gene amplifier," Science 254: 1292-1293.
Welsh, et al., "Analysis of gene expression identifies candidate markers and pharmacological targets in prostate cancer", Cancer Research, vol. 61, Aug. 15, 2001, pp. 5974-5978.
Wennerberg et al., 2005, "The Ras superfamily at a glance," J. Cell Sci, 118 (Pt 5): 843-6.
Whitehead et al., "Variation in tissue-specific gene expression among natural populations." Genome Biology 2005, 6(2): R13.
Wieser, "Rearrangements of Chromosome Band 3q21 in Myeloid Leukemia." Leukemia & Lymphoma Jan. 2002, 43(1): 59-65.
Wigle, et al., "Molecular profiling of non-small cell lung cancer and correlation with disease-free survival", Cancer Research, vol. 62, Jun. 1, 2002, pp. 3005-3008.
Wilhelm et al., "Preclinical overview of sorafenib, a multikinase inhibitor that targets both Raf and VEGF and PDGF receptor tyrosine kinase signaling." Mol Cancer Ther. Oct. 2008; 7(10):3129-40.
Williams, Steven, et al., "CpG-island fragments from the HNRPA2B1/CBX3 genomic locus reduce silencing and enhance transgene expression from the hCMV promoter/enhancer in mammalian cells", BMC Biotechnology, 2005, 5:17,9 pages.
Wilson et al., "The membrane-anchored serine protease, TMPRSS2, activates PAR-2 in prostate cancer cells" Biochem. J. (2005) 388: 967-972.
Wong et al., "A rapid chemical method of labeling human plasma proteins with 99mTc-pertechnetate at pH 7.4." Int J Appl Radiat Isot. May 1978; 29(4-5):251-3.
Wong et al., "Imaging endocarditis with Tc-99m-labeled antibody—an experimental study: concise communication." J Nucl Med. Mar. 1982;23(3):229-34.
Wood et al., "The genomic landscapes of human breast and colorectal cancers." Science. Nov. 16, 2007;318(5853):1108-13.
Wu et al., "Regulation of the ETS transcription factor ER81 by the 90-kDa ribosomal S6 kinase 1 and protein kinase A." J Biology Chem. 2002, 277(45): 42669-42679.
Xing, "BRAF mutation in thyroid cancer." Endocr Relat Cancer. Jun. 2005; 12(2):245-62.
Xu et al, "MAPKAPK2 and HSP27 are downstream effectors of p38 MAP kinase-mediated matrix metalloproteinase type 2 activation and cell invasion in human prostate cancer," ONCOGENE 2006; 25:2987-2998 (2006).
Xu et al., "Identification and Characterization of Prostein, a Novel Prostate-specific Protein" Cancer Research Feb. 15, 2001, 61:1563-1568.
Yang et al., "EWS-Fli-1 Fusion Protein Interacts with Hyperphosphorylated RNA Polymerase II and Interferes with Serine-Arginine Protein-mediated RNA Splicing." J Biol. Chem. 2000, 275(48):37612-37618.
Yoshimoto, et al., "Three-color FISH analysis of TMPRRSS2/ERG fusions in prostate cancer indicates that genomic microdeletion of chromosome 21 is associated with rearrangement", Neoplasia Jun. 2006, 8(6):465-469.
Yu et al., "Gene expression Alterations in Prostate Cancer Predicting Tumor Aggression and Preceding Development of Malignancy." J Clin Onc (Jul. 2004) 22(14):2790-2799.
Yu et al., "Integrative genomics analysis reveals silencing of beta-adrenergic signaling by polycomb in prostate cancer." Cancer Cell. Nov. 2007; 12(5):419-31.

(56) References Cited

OTHER PUBLICATIONS

Zervos et al, "Mxi1, a protein that specifically interacts with Max to bind Myc-Max recognition sites," CELL 1993; 72: 223-232.
Zhan, et al., "Global gene expression profiling of multiple myeloma, monoclonal gammopathy of undetermined significance, and normal bone marrow plasma cells" Blood Mar. 1, 2002, 99(5):1745-1757.
Zhu et al, "Transformation potential of Ras isoforms correlates with activation of phosphatidylinositol 3-kinase but not ERK," J Biol Chem 2004; 279:37398-37406.
Zou et al., "The Oncogenic TLS-ERG Fusion Protein Exerts Different Effects in Hematopoietic Cells and Fibroblasts." Molecular and Cellular Biology 2005, 25(14): 6235-6246.
Zucman et al., "Combinatorial generation of variable fusion proteins in the Ewing family of tumours." EMBO Journal 1993, 12(12): 4481-4487.
Abdulkadir, Sarki A., "Conditional Loss of Nkx3.1 in Adult Mice Induces Prostatic Intraepithelial Neoplasia," Molecular and Cellular Biology, Mar. 2002, 22(5):1495-1503.
Afar, et al., "Catalytic cleavage of the Androgen-regulated TMPRSS2 Protease Results in Its Secretion by Prostate and Prostate Cancer Epithelia," Cancer Research 2001, 61:1686-1692.
Affymetrix HG_U95Av2 array showing ERG https://www.affymetrix.com/analysis/netaffx/fullrecord.affx?pk=HG-U95AV2:36383_AT accesses online Jun. 1, 2012.
Affymetrix NETAFFX Details for MG-U7AV2 Microarray Specifically Showing that ERG is present on the array accessed from www.affymetrix.com on May 1, 2009.
Affymetrix NETAFFX Details for MG-U7AV2 Microarray Specifically Showing that ETV1 is present on the array accessed from www.affymetrix.com on May 1, 2009.
Ahlers & Figg. "ETS-TMPRSS2 fusion gene products in prostate cancer." Cancer Biol Ther. Mar. 2006; 5(3):254-5.
Andren et al., "How Well Does the Gleason Score Predict Prostate Cancer Death? A 20-Year Follow up of a Population Based Cohort in Sweden." J Urol 2006 175:1337-40.
Antoniou et al., "Transgenes encompassing dual-promoter CpG islands from the human TBP and HNRPA2B1 loci are resistant to heterochromatin-mediated silencing", Genomics 2003, 82:269-279.
Asatiani E. et al., "Deletion, methylation, and expression of the NKX3.1 suppressor gene in primary human prostate cancer." Cancer Res. Feb. 15, 2005; 65(4):1164-73.
Attard et al.,Duplication of the fusion of TMPRSS2 to ERG sequences identifies fatal human prostate cancer. Oncogene. Jan. 10, 2008;27(3):253-63.
AU Office Action dated Jul. 5, 2011; Application No. 2009316693; 3 pages.
Australian Further Office Action dated Jan. 18, 2011 (Jan. 18, 2011), Application No. 142006291054; Filing Date: Sep. 12, 2006 (Sep. 12, 2006) 2 Pages.
Australian Office Action dated Jun. 27, 2011 Application No. 2008275304, 2 Pages.
Australian Office Action dated Dec. 23, 2009 (Dec. 23, 2009), Application No. 2006291054; Filing Date: Sep. 12, 2006 (Sep. 12, 2006) 3 Pages.
Australian Office Action dated Nov. 5, 2010 (Nov. 5, 2010); Application No. 2007317306; Filing Date: Nov. 8, 2007 (Nov. 18, 2007) 2 Pages.
Barber et al., "Somatic mutations of EGFR in colorectal cancers and glioblastomas." N Engl J Med. Dec. 30, 2004;351(27):2883.
Barlund et al., "Cloning of BCAS3 (17q23) and BCAS4 (20q13) genes that undergo amplification, overexpression, and fusion in breast cancer." Genes Chromosomes Cancer. Dec. 2002; 35(4):311-7.
Barr et al., "In vivo amplification of the PAX3-FKHR and PAX7-FKHR fusion genes in alveolar rhabdomyosarcoma." Hum Mol Genet. Jan. 1996; 5(1):15-21.
Bartel et al, "Elimination of false positives that arise in using the two-hybrid system," Biotechniques. Jun. 1983; 14(6):920-4.

Bashir et al., "Evaluation of paired-end sequencing strategies for detection of genome rearrangements in cancer." PLoS Comput Biol. Apr. 25, 2008;4(4):e1000051.
Beheshti, B., et al., Identification of a high frequency of chromosomal rearrangements in the centromeric regions of prostate cancer cell lines by sequential giemsa banding and spectral karyotyping Mol Diagn. Mar. 2000; 5(1):23-32.
Beheshti et al., "Evidence of chromosomal instability in prostate cancer determined by spectral karyotyping (SKY) and interphase fish analysis." Neoplasia. Jan.-Feb. 2001;3(1):62-9.
Benner et al., "Evolution, language and analogy in functional genomics." Trends Genet. Jul. 2001; 17(7):414-8.
Bittner et al, "Molecular classification of cutaneous malignant melanoma by gene expression profiling," Nature Aug. 2000, 406:536-540.
Bittner, "A window on the dynamics of biological switches." Nat Biotechnol. Feb. 2005; 23(2):183-4.
Bjartell et al. "Tumor-Associated Trypsin Inhibitor (TATI, PSTI, SPINK1) Expression in Prostate Cancer is Related to Tumor Grade." European Urology Supplements 5.14 (2006): 791.
Block et al., "Use of targeted glycoroteomics to identify serum glycoproteins that correlate with liver cancer in woodchucks and humans." Proc Natl Acad Sci USA (2005) 102:779-784.
Bodmer et al., "Disruption of a novel MFS transporter gene, DIRC2, by a familial renal cell carcinoma-associated t (2;3)(q35;q21)." Hum Mol Genet. Mar. 15, 2002;11(6):641-9.
Bos, "ras Oncogenes in Human Cancer: A Review." Cancer Res 1989; 49:4682-4689.
Brahmajothi et al., "Regional localization of ERG, the channel protein responsible for the rapid component of the delayed rectifier, K+ current in the ferret heart." Circulation Research 1997, 81(1):128-135.
Burns Ed., Immunochemical Protocols, 3rd Ed., Humana Press, 2005.
Bussemakers et al., "DD3:A new Prostate-specific Gene, Highly Overexpressed in Prostate Cancer," Cancer Res. (1999) 59:5975-5979.
Bussemakers, "Changes in Gene Expression and Targets for Therapy." Eur. Urol. (1999) 35:408-412.
CA Office Action dated Mar. 29, 2011 (Application No. 2692441).
Cai et al., "ETV1 is a Novel Androgen Receptor-Regulated Gene that Mediates Prostate Cancer Cell Invasion", Molecular Endocrinology May 15, 2007, 21(8):835-1846.
Campbell et al., "Identification of somatically acquired rearrangements in cancer using genome-wide massively parallel paired-end sequencing." Nat Genet. Jun. 2008;40(6):722-9.
Canadian Office Action dated Nov. 16, 2010 (Nov. 16, 2010), Application No. 2,662,295; Filing Date: Sep. 12, 2006 (Sep. 12, 2006) 11 Pages.
Canadian Office Action dated Jan. 6, 2011 (Jan. 6, 2011); Application No. 2,668,961; Filing Date: Nov. 8, 2007 (Nov. 8, 2007) 5 Pages.
Cerveira, et al. "TMPRSS2-ERG Gene Fusion Causing ERG Overexpression Precedes Chromosome Copy Number Changes in Prostate Carcinomas and Paired HGPIN Lesions." Neoplasia 2006; 8(10):826-832.
Chen, et al., "Variation in gene expression patterns in human gastric cancers" Mol Biol Cell. Aug. 2003; 14(8):3208-15.
Cheok et al., "Treatment-specific changes in gene expression discriminate in vivo drug response in human leukemia cells." Nat Genet. May 2003; 34(1):85-90.
Cheung et al., "Integration of cytogenetic landmarks into the draft sequence of the human genome." Nature 2001, 409:953-958.
Chinese Office Action dated Dec. 31, 2010 (Dec. 31, 2010), Application No. 200680041826.6; Filing Date: Sep. 12, 2006 (Sep. 12, 2006) Publication No. 101341256 (8 Pages).
Cho et al., "BRAF and KRAS mutations in prostatic adenocarcinoma." Int J Cancer. Oct. 15, 2006;119(8):1858-62.
Choi et al., "Identification of novel isoforms of the EML4-ALK transforming gene in non-small cell lung cancer." Cancer Res. Jul. 1, 2008;68(13):4971-6.

(56) References Cited

OTHER PUBLICATIONS

Ciampi, "Oncogenic AKAP9-BRAF fusion is a novel mechanism of MAPK pathway activation in thyroid cancer." J Clin Invest. Jan. 2005; 115(1):94-101.
Ciampi et al., "BRAF kinase activation via chromosomal rearrangment in radiation-induced and sporadic thyroid cancer." Cell Cycle 2005 4(4): 547-548.
Cohen et al, "BRAF mutation in papillary thyroid carcinoma." J Natl Cancer Inst. Apr. 16, 2003; 95(8):625-7.
Lin et al., "Prostate-localized and Androgen-regulated Expression of the Membrane-bound Serine Protease TMPRSS21" Cancer Res. Sep. 1, 1999; 59(17):4180-4.
Liu et al., "Lineage relationship between LNCaP and LNCaP-derived prostate cancer cell lines." Prostate. Jul. 1, 2004; 60(2):98-108.
Lizardi et al, "Exponential Amplification of Recombinant-RNA Hybridization Probes," Biotechnology Oct. 1988; 6:1197-1202.
Lukkonen et al., "Tumor-associated trypsin inhibitor in normal and malignant renal tissue and in serum of renal-cell carcinoma patients." International J of Cancer 1999, 83(4):486-490.
Lynch et al., "Activating mutations in the epidermal growth factor receptor underlying responsiveness of non-small-cell lung cancer to gefitinib." N Engl J Med. May 20, 2004; 350(21):2129-39.
MacConaill et al., "Profiling critical cancer gene mutations in clinical tumor samples." PLoS One. Nov. 18, 2009; 4(11):e7887.
Madura et al, "N-recognin/Ubc2 interactions in the N-end rule pathway," J Biol Chem 1993, 268:12046-12054.
Maher et al., "Chmimeric transcript discovery by paird-end transcriptome sequencing" Proceedings of the National Academy of Sciences of the United States of America (Jul. 2009) 106(30):12353-12358.
Maher et al., "Transciptome sequencing to detect gene fusions in cancer." Nature (Mar. 2009) 458(7234):97-101.
Makkonen et al., "Identification of ETS-like transcriptome factor 4 as a novel androgen receptor target in prostate cancer cells." Oncogene May 12, 2008, 27(36): 4865-4876.
Mark et al, (Apr. 1984), "Primary structure of v-raf: relatedness to the src family of oncogenes," Science 224(4646) 285-9.
Marks et al., "PCA3 Molecular Urine Assay for Prostate Cancer in Men Undergoing Repeat Biopsy." Urology (2007) 69:532-5.
McConnell et al., "The cytosensor microphysiometer: biological applications of silicon technology." Science. Sep. 25, 1992;257(5078):1906-12.
Mehra et al., "Comprehensive assessment of TMPRSS2 and ETS family gene aberrations in clinically localized prostate cancer." Mod Pathol. May 2007; 20(5):538-44.
Mirosevich et al., "Expression and role of Foxa proteins in Prostate Cancer" Prostate. Jul. 1, 2006; 66(10):1013-28.
Mirosevich et al., "Expression of Foxa Transcription Factors in the Developing and Adult Murine Prostate", Prostate. Mar. 1, 2005; 62(4):339-52.
Mitelman et al., "Fusion genes and rearranged genes as a linear function of chromosome aberrations in cancer." Nat Genet. Apr. 2004;36(4):331-4.
Mitelman et al., "Prevalence estimates of recurrent balanced cytogenetic aberrations and gene fusions in unselected patients with neoplastic disorders." Genes Chromosomes Cancer. Aug. 2005;43(4):350-66.
Mitelman "Recurrent chromosome aberrations in cancer", Mutat Res. Apr. 2000; 462(2-3):247-53.
Montagut et al., "Targeting the RAF-MEK-ERK pathway in cancer therapy." Cancer Letters Feb. 2009, 283(2):125-134.
Morris et al., "The discovery and application of gene fusions in prostate cancer." BJU Int. Aug. 2008; 102(3):276-82.
Mosquera, et al. "Morphological Features of TMPRSS2-ERG gene fusion prostate cancer." J Pathol. May 2007; 212(1):91-101.

Moul et al, "Infrequent RAS oncogene mutations in human prostate cancer," Prostate. 1992; 20(4):327-38.
Moynihan et al, "Fine-mapping, genomic organization, and transcript analysis of the human ubiquitin-conjugating enzyme gene UBE2L3," Genomics. Jul. 1, 1998; 51(1):124-7.
Mullighan et al, "BCR-ABL1 lymphoblastic leukaemia is characterized by the deletion of Ikaros," NATURE 453, 110-114 (2008).
Mullis et al., "Specific synthesis of DNA in vitro via a polymerase-catalyzed chain reaction," Methods Enzymol. 1987; 155:335-50.
Munemitsu et al., "Molecular cloning and expression of a G25K cDNA, the human homolog of the yeast cell cycle gene CDC42." Mol Cell Biol. Nov. 1990; 10(11):5977-82.
Murakawa et al., "Direct detection of HIV-1 RNA from AIDS and ARC patient samples," DNA. May 1988; 7(4):287-95.
Murillo et al., "Prostate Cancer Cells use Genetic an Epigenetic mechanisms for Progression to Androgen Independence", Genes, Chromosomes & Cancer, 2006, pp. 702-716.
Nam Robert K et al., "Expression of TMPRSS2: ERG gene fusion in prostate cancer cells is an important prognostic factor for cancer progression," Cancer Biology & Therapy Jan. 2007; 6:40-45.
NC_000003.10, *Homo sapiens* chromosome 3, reference assembly, complete sequence, 1 page, Mar. 3, 2008.
Nelson, Norman C., et al., (1995) "Detection of Acridinium Esters by Chemiluminescence" Nonisotopic Probing, Blotting, and Sequencing, 2nd Edition, edited by Larry J. Kricka, Ch. 17, pp. 391-428.
Neve et al., "A collection of breast cancer cell lines for the study of functionally distinct cancer subtypes." Cancer Cell. Dec. 2006; 10(6):515-27.
NM_004454.2, *Homo sapiens* ets variant 5 (ETV5), mRNA, 5 pages, Mar. 31, 2013.
Oettgen, et al. "PDEF, a Novel Prostate Epithelium-specific Ets Transcription Factor, Interacts with the Androgen Receptor and Activates Prostate-specific Antigen Gene Expression." Journal of Biological Chemistry 2000, 275(2):1216-1225.
Oikawa T. et al., "Molecular biology of the ETS family of transcription factors." Gene 2003, 303(16):11-34.
Olive, "Quantitative methods for the analysis of protein phosphorylation in drug development." Expert Rev Proteomics Oct. 2004; 1(3):327-41.
Ono et al., "Stimulation of Expression of the Human Endogenous retrovirus Genome by Female Steroid Hormones in Human Breast Cancer Cell Line T47D", Journal of Virology, Jun. 1987, pp. 2059-2062.
Ota et al., "Complete sequencing and characterization of 21,243 full-length human cDNAs." Nat Genet. Jan. 2004;36(1):40-5.
Owczarek et al. "Detailed mapping of the ERG-ETS2 interval of human chromosome 21 and comparison with the region of conserved synteny on mouse chromosome 16." Gene 2004; 324:65-77.
Paju et al., "Biochemistry and Clinical Role of Trypsinogens and Pancreatic Secretory Trypsin Inhibitor." Crit. Rev. Clin. Lab Sci. (2006) 43:103-42.
Paju et al., "Increased Expression of Tumor-Associated Trypsin Inhibitor, TATI, in Prostate Cancer and in Androgen-Independent 22Rv1 Cells." Eur Urol (2007) 52:1670-1681.
Palanisamy, N. "Rearrangements of the RAF kinase pathway in prostate cancer, gastric cancer and melanoma." Nature Medicine 2010 16(7):793-798.
Pang et al., "Cytogenetic and Expression profiles Associated with Transformation to Androgen-Resistant Prostate Cancer", the Prostate 2006; 66: 157-172.
Paoloni-Giacobino et al., "Cloning of the TMPRSS2 gene, which encodes a novel serine protease with transmembrane, LDLRA, and SRCR domains and maps to 21q22.3", Genomics Sep. 15, 1997; 44(3):309-320.
Paris et al., "Whole genome scanning identifies genotypes associated with recurrence and metastasis in prostate tumors" Human Molecular Genetics 2004, 13(13):1303-1313.
Park et al., "Antibody-Based Detection of ERG Rearrangement-Positive Prostate Cancer." Neoplasia Jul. 2010, 12(7):590-598.
Parsons et al., "An integrated genomic analysis of human glioblastoma multiforme." Science. Sep. 26, 2008;321(5897):1807-12.

(56) References Cited

OTHER PUBLICATIONS

Patience et al., "Human Endogenous Retrovirus Expression and Reverse Transcriptase Activity in the T47D Mammary Carcinoma Cell Line", Journal of Virology, Apr. 1996, 70(4):2654-2657.
Perner et al., "EML4-ALK fusion lung cancer: a rare acquired event." Neoplasia. Mar. 2008; 10(3):298-302.
Affymetrix HG_U95Av2 array showing SPINK1 https://www.affymetrix.com/analysis/netaffx/fullrecord.affx?pk=HG-U95AV2:38582_AT accesses online Jun. 1, 2012.
Affymetrix NETAFFX Details for MG-U74AV2 Accessed from www.affymetrix.com on Aug. 18, 2008.
Edwards et al., "Expression analysis onto microarrays of randomly selected cDNA clones highlights HOXB13 as a marker of human prostate cancer." Br J Cancer. Jan. 31, 2005;92(2):376-81.
Einhauer et al., "The FLAG peptide, a versatile fusion tag for the purification of recombinant proteins." J Biochem Biophys Methods. Oct. 30, 2001;49(1-3):455-65.
He, et al., "Profile of ETS gene expression in human breast carcinoma." Cancer Biol Ther. Jan. 2007;6(1):76-82.
NEB Catalog, 1998/99, pp. 121 and 284.
Forrest (1999) "Detection of MLL gene self-fusions by RT-PCR and automated fluorescent DNA-fragment analysis" Cancer Genet Cytogenet 112(2): 181-3.
Pfluger, D. Towards Understanding of Prostate Cancer Heterogenity. Master Thesis. Universitat Ulm and Weill Cornell Medical College. 2008. 58 pages.
Fischer et al., "B- and C-RAF display essential differences in their binding to Ras: the isotype-specific N terminus of B-RAF facilitates Ras binding." J Biol Chem. Sep. 7, 2007;282(36):26503-16.
Ichikawa et al., "Dual transforming activities of the FUS (TLS)-ERG leukemia fusion protein conferred by two N-terminal domains of FUS (TLS)." Mol Cell Biol. Nov. 1999;19(11):7639-50.
He Jintang et al., "Antibody-independent targeted quantification of TMPRSS2-ERG fusion protein products in prostate cancer." Mol Oncol. Oct. 2014;8(7):1169-80.
Tackels-Horne et al., "Identification of differentially expressed genes in hepatocellular carcinoma and metastatic liver tumors by oligonucleotide expression profiling." Cancer Jul. 15, 2001;92(2):395-405.
Zucman "EWS and ATF-1 gene fusion induced by t(12;22) translocation in malignant melanoma of soft parts" Nature Genetics 4: 341-344 (1993).

* cited by examiner

Figure 1
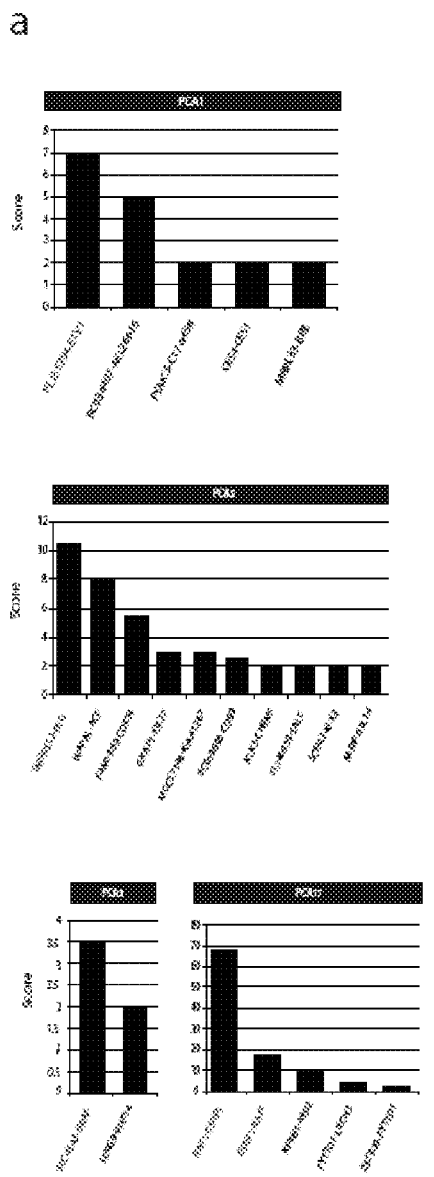
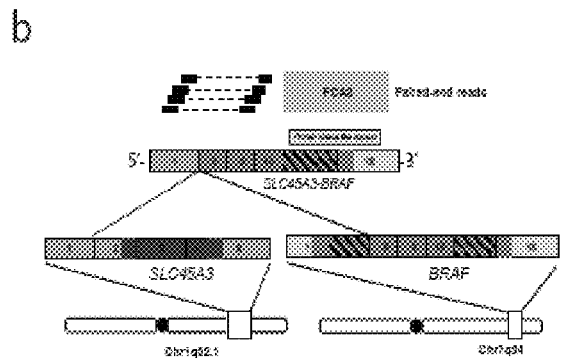
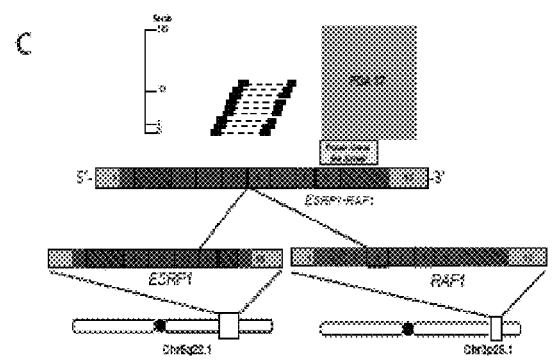
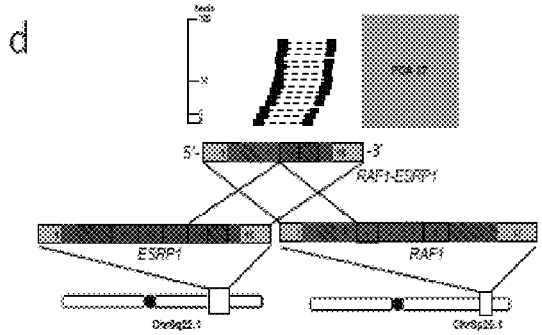

Figure 5
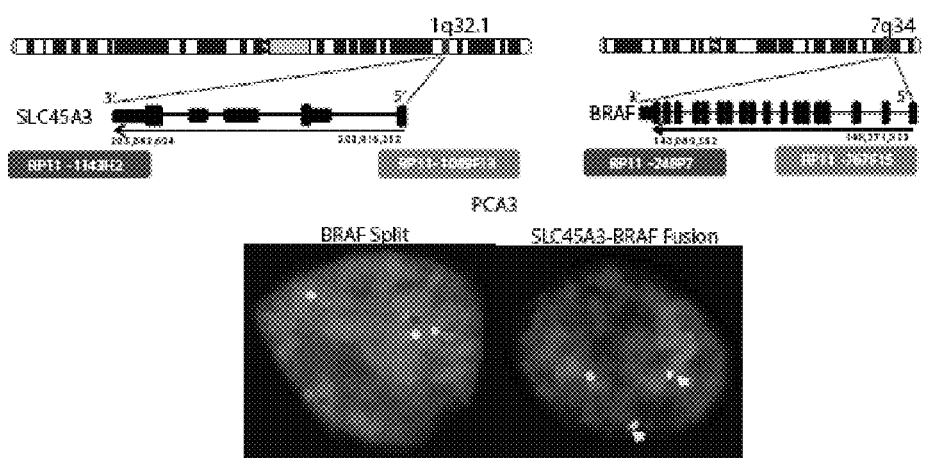
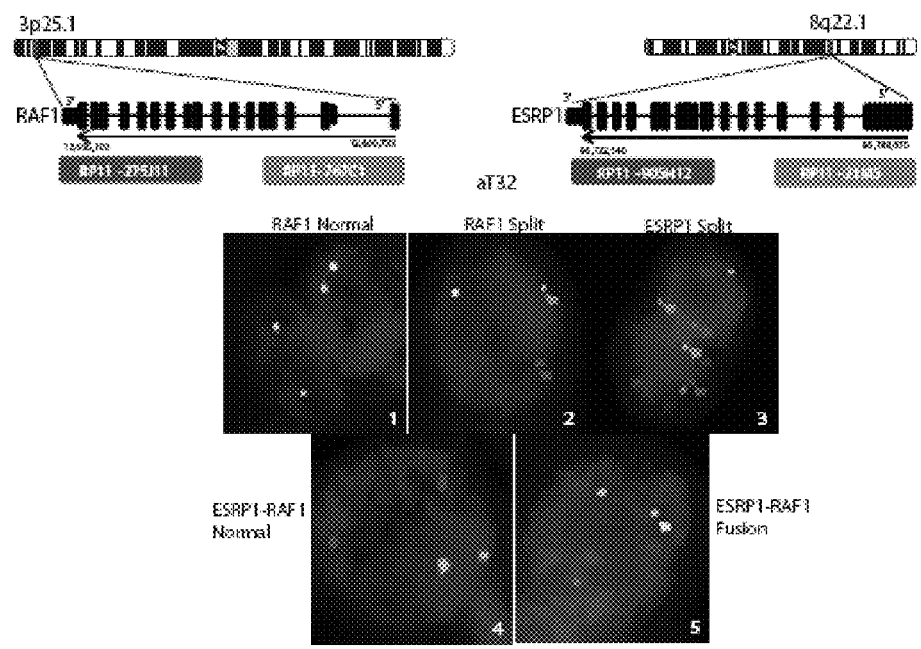

Figure 6
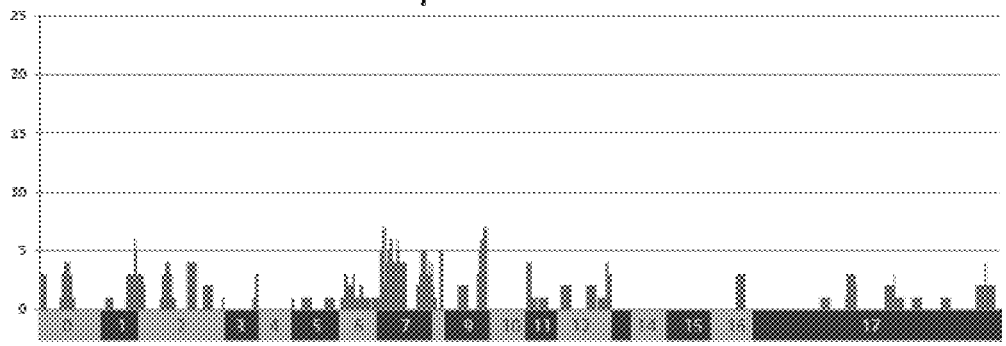
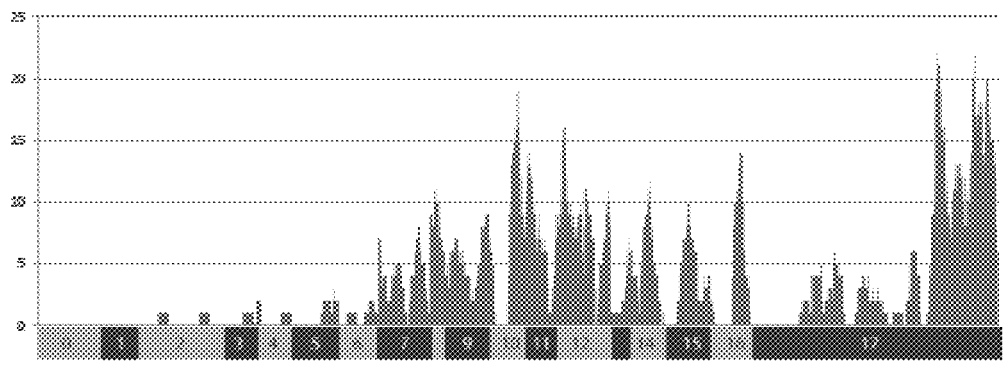

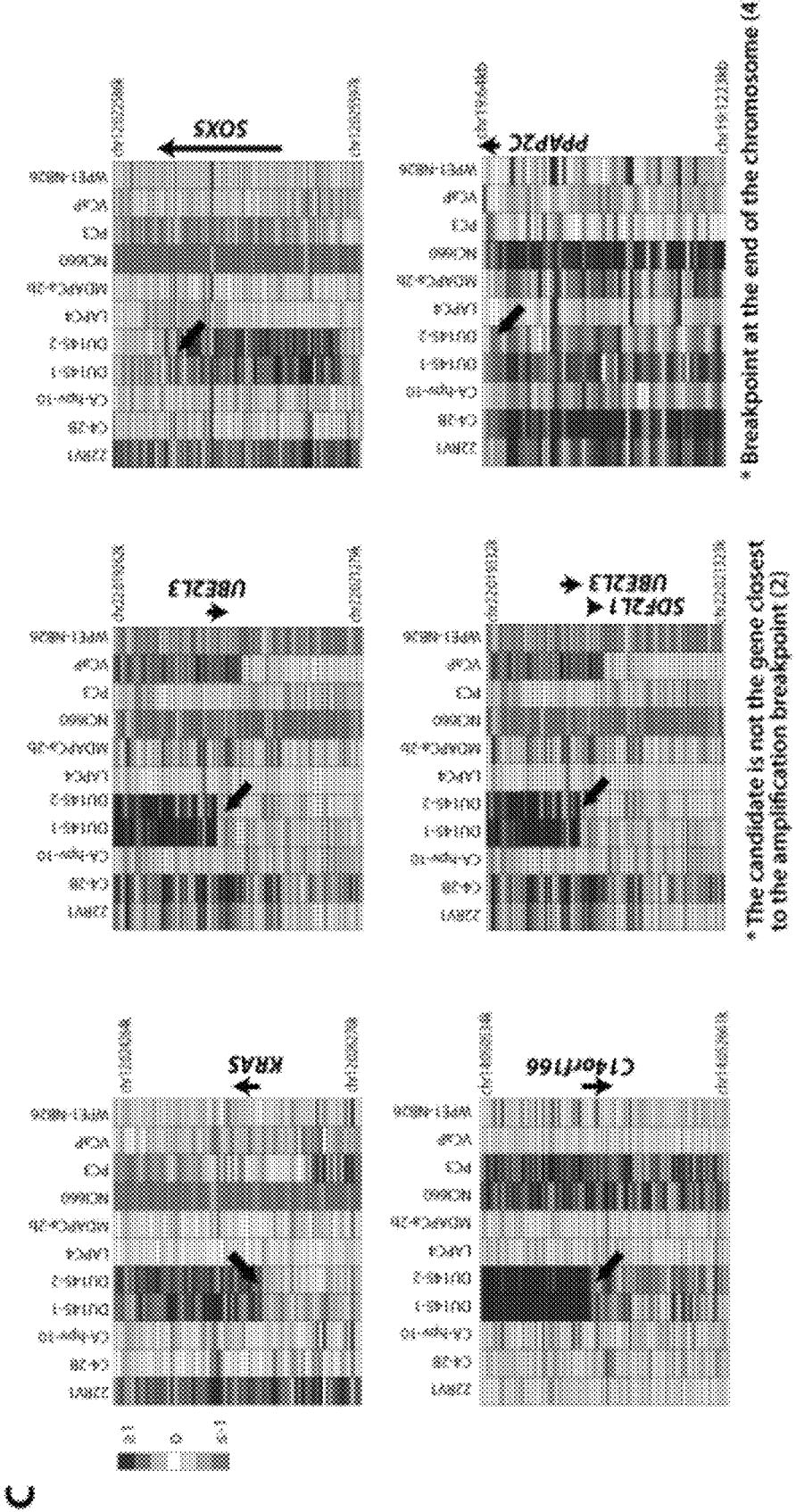

RECURRENT GENE FUSIONS IN PROSTATE CANCER

This application is a divisional of U.S. patent application Ser. No. 12/882,533, filed Sep. 15, 2010, which claims priority to U.S. provisional patent application Ser. No. 61/243,226, filed Sep. 17, 2009, each of which are incorporated herein by reference in its entirety.

GOVERNMENT SUPPORT

This invention was made with government support under CA069568, CA111275 and CA132874 awarded by the National Institutes of Health. The government has certain rights in the invention.

FIELD OF THE INVENTION

The present invention relates to compositions and methods for cancer diagnosis, research and therapy, including but not limited to, cancer markers. In particular, the present invention relates to recurrent gene fusions as diagnostic markers and clinical targets for prostate cancer.

BACKGROUND OF THE INVENTION

A central aim in cancer research is to identify altered genes that are causally implicated in oncogenesis. Several types of somatic mutations have been identified including base substitutions, insertions, deletions, translocations, and chromosomal gains and losses, all of which result in altered activity of an oncogene or tumor suppressor gene. First hypothesized in the early 1900's, there is now compelling evidence for a causal role for chromosomal rearrangements in cancer (Rowley, *Nat Rev Cancer* 1: 245 (2001)). Recurrent chromosomal aberrations were thought to be primarily characteristic of leukemias, lymphomas, and sarcomas. Epithelial tumors (carcinomas), which are much more common and contribute to a relatively large fraction of the morbidity and mortality associated with human cancer, comprise less than 1% of the known, disease-specific chromosomal rearrangements (Mitelman, *Mutat Res* 462: 247 (2000)). While hematological malignancies are often characterized by balanced, disease-specific chromosomal rearrangements, most solid tumors have a plethora of non-specific chromosomal aberrations. It is thought that the karyotypic complexity of solid tumors is due to secondary alterations acquired through cancer evolution or progression.

Two primary mechanisms of chromosomal rearrangements have been described. In one mechanism, promoter/enhancer elements of one gene are rearranged adjacent to a proto-oncogene, thus causing altered expression of an oncogenic protein. This type of translocation is exemplified by the apposition of immunoglobulin (IG) and T-cell receptor (TCR) genes to MYC leading to activation of this oncogene in B- and T-cell malignancies, respectively (Rabbitts, *Nature* 372: 143 (1994)). In the second mechanism, rearrangement results in the fusion of two genes, which produces a fusion protein that may have a new function or altered activity. The prototypic example of this translocation is the BCR-ABL gene fusion in chronic myelogenous leukemia (CML) (Rowley, *Nature* 243: 290 (1973); de Klein et al., *Nature* 300: 765 (1982)). Importantly, this finding led to the rational development of imatinib mesylate (Gleevec), which successfully targets the BCR-ABL kinase (Deininger et al., *Blood* 105: 2640 (2005)). Thus, identifying recurrent gene rearrangements in common epithelial tumors may have profound implications for cancer drug discovery efforts as well as patient treatment.

SUMMARY OF THE INVENTION

The present invention relates to compositions and methods for cancer diagnosis, research and therapy, including but not limited to, cancer markers. In particular, the present invention relates to recurrent gene fusions as diagnostic markers and clinical targets for prostate cancer.

For example, in some embodiments, the present invention provides a method for identifying prostate cancer in a patient comprising: providing a sample from the patient; and detecting the presence or absence in the sample of a gene fusion having a 5' portion from a transcriptional regulatory region of an SLC45A3 gene and a 3' portion from a RAF family gene (e.g., RAF1 or BRAF), wherein detecting the presence in the sample of the gene fusion identifies prostate cancer in the patient. In some embodiments, the transcriptional regulatory region of the SLC45A3 gene comprises a promoter region of the SLC45A3 gene. In some embodiments, the detecting step comprises detecting chromosomal rearrangements of genomic DNA having a 5' DNA portion from the transcriptional regulatory region of the SLC45A3 gene and a 3' DNA portion from the RAF family gene. In some embodiments, the detecting step comprises detecting chimeric mRNA transcripts having a 5' RNA portion transcribed from the transcriptional regulatory region of the SLC45A3 gene and a 3' RNA portion transcribed from a RAF family gene. In some embodiments, the sample is tissue, blood, plasma, serum, urine, urine supernatant, urine cell pellet, semen, prostatic secretions or prostate cells.

Further embodiments of the present invention provide a method for identifying prostate cancer in a patient comprising: providing a sample from the patient; and detecting the presence or absence in the sample of a gene fusion having a 5' portion from a transcriptional regulatory region of a UBE2L3 gene and a 3' portion from a RAS family gene (e.g., KRAS), wherein detecting the presence in the sample of the gene fusion identifies prostate cancer in the patient. In some embodiments, the transcriptional regulatory region of the UBE2L3 gene comprises a promoter region of the UBE2L3 gene. In some embodiments, the detecting step comprises detecting chromosomal rearrangements of genomic DNA having a 5' DNA portion from the transcriptional regulatory region of the UBE2L3 gene and a 3' DNA portion from the RAS family gene. In some embodiments, the detecting step comprises detecting chimeric mRNA transcripts having a 5' RNA portion transcribed from the transcriptional regulatory region of the UBE2L3 gene and a 3' RNA portion transcribed from a RAS family gene. In some embodiments, the sample is tissue, blood, plasma, serum, urine, urine supernatant, urine cell pellet, semen, prostatic secretions or prostate cells.

In further embodiments, the present invention provides a composition comprising at least one of the following: (a) an oligonucleotide probe comprising a sequence that hybridizes to a junction of a chimeric genomic DNA or chimeric mRNA in which a 5' portion of the chimeric genomic DNA or chimeric mRNA is from a transcriptional regulatory region of an SLC45A3 gene and a 3' portion of the chimeric genomic DNA or chimeric mRNA is from a RAF family member gene; (b) a first oligonucleotide probe comprising a sequence that hybridizes to a 5' portion of a chimeric genomic DNA or chimeric mRNA from a transcriptional regulatory region of an SLC45A3 gene and a second oligonucleotide probe comprising a sequence that hybridizes to a 3' portion of the chimeric genomic DNA or chimeric mRNA from a RAF family member gene; (c) a first amplification oligonucleotide comprising a sequence that hybridizes to a 5' portion of a chimeric genomic DNA or chimeric mRNA from a transcriptional regulatory region of an SLC45A3 gene and a second amplification oligonucleotide comprising a sequence that hybridizes to a 3' portion of the chimeric genomic DNA or chimeric mRNA from a RAF family member gene; (d) an oligonucleotide probe comprising a sequence that hybridizes to a junction of a chimeric genomic DNA or chimeric mRNA in which a 5' portion of the chimeric genomic DNA or chimeric mRNA is from a transcriptional regulatory region of an UBE2L3 gene and a 3' portion of the chimeric genomic DNA or chimeric mRNA is from a RAS family member gene; (e) a first oligonucleotide probe comprising a sequence that hybridizes to a 5' portion of a chimeric genomic DNA or chimeric mRNA from a transcriptional regulatory region of an UBE2L3 gene and a second oligonucleotide probe comprising a sequence that hybridizes to a 3' portion of the chimeric genomic DNA or chimeric mRNA from a RAS family member gene; (f) a first amplification oligonucleotide comprising a sequence that hybridizes to a 5' portion of a chimeric genomic DNA or chimeric mRNA from a transcriptional regulatory region of an UBE2L3 gene and a second amplification oligonucleotide comprising a sequence that hybridizes to a 3' portion of the chimeric genomic DNA or chimeric mRNA from a RAS family member gene; and (g) an antibody to a chimeric protein having an animo-terminal portion encoded by the UBE2L3 gene and a carboxy-terminal portion encoded by a RAS family member gene. In some embodiments, the RAF family member gene is BRAF or RAF1. In some embodiments, the RAS family member gene is KRAS.

Additional embodiments of the present invention are provided in the description and examples below.

DESCRIPTION OF THE FIGURES

FIG. 1 shows the discovery of SLC45A3-BRAF and ESRP1-RAF1 and RAF1-ESRP1 gene fusions in ETS negative prostate cancer. (a) Histogram of gene fusion nomination scores in clinically localized prostate tumor samples PCA1, PCA2, PCA3 and PCA17 harboring FLJ35294-ETV1 (top), TMPRSS2-ERG (middle), SLC45A3-BRAF (bottom left) and ESRP1-RAF1 and RAF1-ESRP1 (bottom right), respectively. (b) Schematic representation of paired-end reads supporting the inter-chromosomal gene fusion between SLC45A3 and BRAF. (c &d) Schematic representation of paired-end reads supporting inter chromosomal gene fusions between ESRP1 and RAF1 resulting in reciprocal fusion genes ESRP1-RAF1 and RAF1-ESRP1.

FIG. 5 shows genomic organization and FISH validation of BRAF and RAF1 gene rearrangement. Schematic diagrams in the top panel of (a) and (b) showing the genomic location of SLC45A3 and BRAF and ESRP1 and RAF1 genes respectively.

FIG. 6 shows RNA-seq exon coverage of BRAF in normal sample (NOR9) and index case (PCA3).

DEFINITIONS

Figure 2:
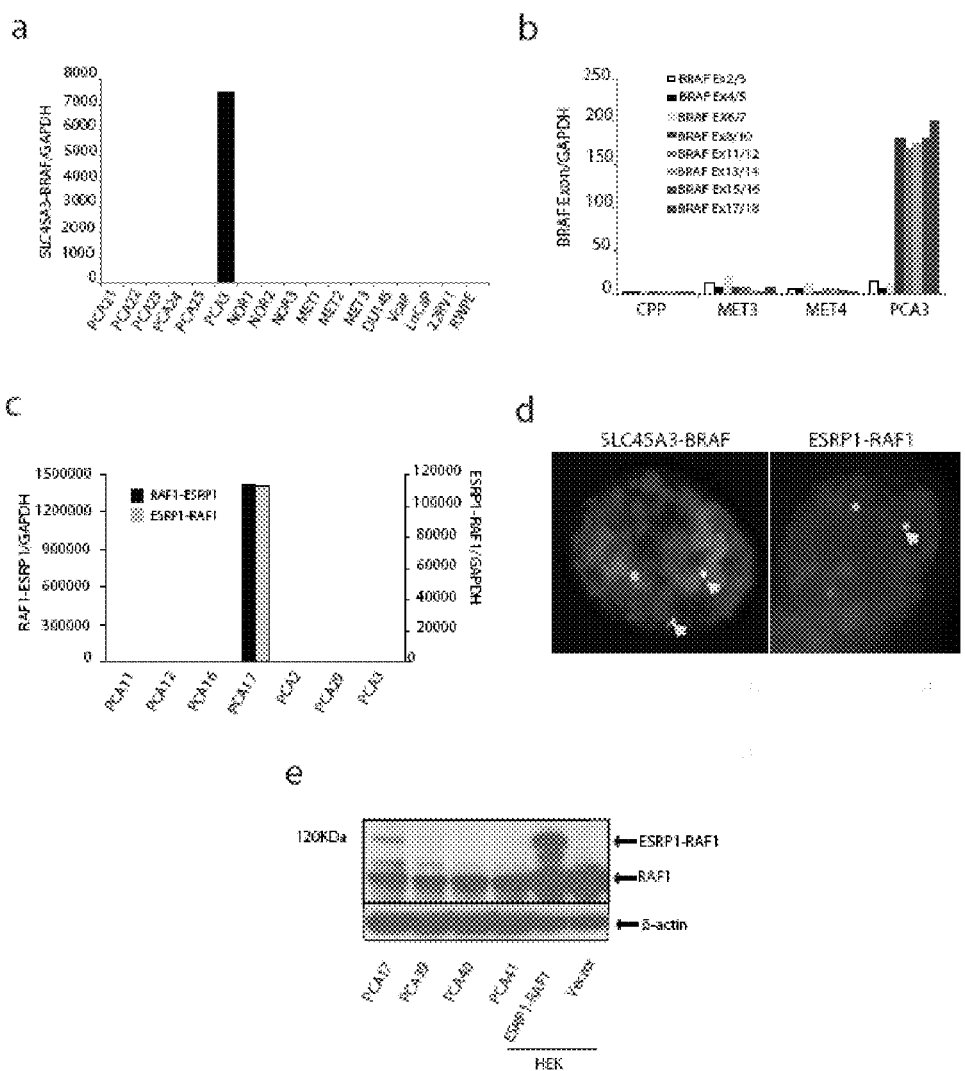
FIG. 2 shows validation of expression of SLC45A3-BRAF, ESRP1-RAF1 and RAF1-ESRP gene fusions. (a) qRT-PCR validation of SLC45A3-BRAF gene fusion in PCA3 and (b) exon specific PCR using exons spanning primers showing the high level expression of BRAF exons 8-18 relative to the exons 1-7. (c) qRT-PCR validation of ESRP1-RAF1 and RAF1-ESRP1 reciprocal gene fusions in PCA17. (d) FISH validation of SLC45A3-BRAF (left) and ESRP1-RAF1 (right) gene fusion in PCA3 and PCA17 respectively. (e) Western blot analysis showing the expression of 120 kDa ESRP1-RAF1 fusion protein in PCA17 and in HEK293 cells transfected with ESRP1-RAF1 full length fusion construct cloned from PCA17.

To facilitate an understanding of the present invention, a number of terms and phrases are defined below:

As used herein, the term "gene fusion" refers to a chimeric genomic DNA, a chimeric messenger RNA, a truncated protein or a chimeric protein resulting from the fusion of at least a portion of a first gene to at least a portion of a second gene. The gene fusion need not include entire genes or exons of genes.

As used herein, the term "gene upregulated in cancer" refers to a gene that is expressed (e.g., mRNA or protein expression) at a higher level in cancer (e.g., prostate cancer) relative to the level in other tissues. In some embodiments, genes upregulated in cancer are expressed at a level at least 10%, preferably at least 25%, even more preferably at least 50%, still more preferably at least 100%, yet more preferably at least 200%, and most preferably at least 300% higher than the level of expression in other tissues. In some embodiments, genes upregulated in prostate cancer are "androgen regulated genes."

As used herein, the term "gene upregulated in prostate tissue" refers to a gene that is expressed (e.g., mRNA or protein expression) at a higher level in prostate tissue relative to the level in other tissue. In some embodiments, genes upregulated in prostate tissue are expressed at a level at least 10%, preferably at least 25%, even more preferably at least 50%, still more preferably at least 100%, yet more preferably at least 200%, and most preferably at least 300% higher than the level of expression in other tissues. In some embodiments, genes upregulated in prostate tissue are exclusively expressed in prostate tissue.

As used herein, the term "transcriptional regulatory region" refers to the region of a gene comprising sequences that modulate (e.g., upregulate or downregulate) expression of the gene. In some embodiments, the transcriptional regulatory region of a gene comprises non-coding upstream sequence of a gene, also called the 5' untranslated region (5'UTR). In other embodiments, the transcriptional regulatory region contains sequences located within the coding region of a gene or within an intron (e.g., enhancers).

As used herein, the term "androgen regulated gene" refers to a gene or portion of a gene whose expression is induced or repressed by an androgen (e.g., testosterone). The promoter region of an androgen regulated gene may contain an "androgen response element" that interacts with androgens or androgen signaling molecules (e.g., downstream signaling molecules).

As used herein, the terms "detect", "detecting" or "detection" may describe either the general act of discovering or discerning or the specific observation of a detectably labeled composition.

As used herein, the term "stage of cancer" refers to a qualitative or quantitative assessment of the level of advancement of a cancer. Criteria used to determine the stage of a cancer include, but are not limited to, the size of the tumor and the extent of metastases (e.g., localized or distant).

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N-6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N-6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to at least a portion of another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

DETAILED DESCRIPTION OF THE INVENTION

The present invention is based on the discovery of recurrent gene fusions in prostate cancer. The present invention provides diagnostic, research, and therapeutic methods that either directly or indirectly detect or target the gene fusions. The present invention also provides compositions for diagnostic, research, and therapeutic purposes.

I. Gene Fusions

The present invention identifies recurrent gene fusions indicative of prostate cancer. In some embodiments, the gene fusions are the result of a chromosomal rearrangement of an transcriptional regulatory region of a first gene (e.g., an androgen regulated gene or other gene) and an RAS or RAF family member gene. The gene fusions typically comprise a 5' portion from a transcriptional regulatory region of first gene (e.g., UBE2L3 or an androgen regulated gene such as SLC45A3) and a 3' portion from an ETS family member gene. The recurrent gene fusions have use as diagnostic markers and clinical targets for prostate cancer.

A. Androgen Regulated Genes

Genes regulated by androgenic hormones are of critical importance for the normal physiological function of the human prostate gland. They also contribute to the development and progression of prostate carcinoma. Recognized ARGs include, but are not limited to: TMPRSS2; SLC45A3; HERV-K_22q11.23; C15ORF21; FLJ35294; CANT1; PSA; PSMA; KLK2; SNRK; Seladin-1; and, FKBP51 (Paoloni-Giacobino et al., *Genomics* 44: 309 (1997); Velasco et al., *Endocrinology* 145(8): 3913 (2004)).

TMPRSS2 (NM_005656) has been demonstrated to be highly expressed in prostate epithelium relative to other normal human tissues (Lin et al., *Cancer Research* 59: 4180 (1999)). The TMPRSS2 gene is located on chromosome 21. This gene is located at 41,750,797-41,801,948 bp from the pter (51,151 total bp; minus strand orientation). The human TMPRSS2 protein sequence may be found at GenBank accession no. AAC51784 (Swiss Protein accession no. O15393) and the corresponding cDNA at GenBank accession no. U75329 (see also, Paoloni-Giacobino, et al., *Genomics* 44: 309 (1997)).

SLC45A3, also known as prostein or P501 S, has been shown to be exclusively expressed in normal prostate and prostate cancer at both the transcript and protein level (Kalos et al., Prostate 60, 246-56 (2004); Xu et al., Cancer Res 61, 1563-8 (2001)).

HERV-K_22q11.23, by EST analysis and massively parallel sequencing, was found to be the second most strongly expressed member of the HERV-K family of human endogenous retroviral elements and was most highly expressed in the prostate compared to other normal tissues (Stauffer et al., Cancer Immun 4, 2 (2004)). While androgen regulation of HERV-K elements has not been described, endogenous retroviral elements have been shown to confer androgen responsiveness to the mouse sex-linked protein gene C4A (Stavenhagen et al., Cell 55, 247-54 (1988)). Other HERV-K family members have been shown to be both highly expressed and estrogen-regulated in breast cancer and breast cancer cell lines (Ono et al., J Virol 61, 2059-62 (1987); Patience et al., J Virol 70, 2654-7 (1996); Wang-Johanning et al., Oncogene 22, 1528-35 (2003)), and sequence from a HERV-K3 element on chromosome 19 was fused to FGFR1 in a case of stem cell myeloproliferative disorder with t(8; 19)(p12; q13.3) (Guasch et al., Blood 101, 286-8 (2003)).

C15ORF21, also known as D-PCA-2, was originally isolated based on its exclusive over-expression in normal prostate and prostate cancer (Weigle et al., Int J Cancer 109, 882-92 (2004)).

FLJ35294 was identified as a member of the "full-length long Japan" (FLJ) collection of sequenced human cDNAs (Nat. Genet. 2004 January; 36(1):40-5. Epub 2003 December 21).

CANT1, also known as sSCAN1, is a soluble calcium-activated nucleotidase (Arch Biochem Biophys. 2002 Oct. 1; 406(1):105-15). CANT1 is a 371-amino acid protein. A cleavable signal peptide generates a secreted protein of 333 residues with a predicted core molecular mass of 37,193 Da. Northern analysis identified the transcript in a range of human tissues, including testis, placenta, prostate, and lung. No traditional apyrase-conserved regions or nucleotide-binding domains were identified in this human enzyme, indicating membership in a new family of extracellular nucleotidases.

In some embodiments, gene fusions of the present invention comprise transcriptional regulatory regions of an ARG. The transcriptional regulatory region of an ARG may contain coding or non-coding regions of the ARG, including the promoter region. The promoter region may further comprise an androgen response element (ARE) of the ARG.

B. Ubiquitin Conjugating Enzymes

Ubiquitin-conjugating enzymes, also known as E2 enzymes, perform the second step in the ubiquitination reaction that targets a protein for degradation via the proteasome. The ubiquitination process covalently attaches ubiquitin, a short protein of 76 amino acids, to a lysine residue on the target protein. Once a protein has been tagged with one ubiquitin molecule, additional rounds of ubiquitination form a polyubiquitin chain that is recognized by the proteasome's 19S regulatory particle, triggering the ATP-dependent unfolding of the target protein that allows passage into the proteasome's 20S core particle, where proteases degrade the target into short peptide fragments for recycling by the cell.

UBE2L3 is one example of a human E2 enzyme. The mRNA sequence of UBE2L3 is described by Genbank Accession number NR_028437.

C. RAS/RAF Families

Ras is a family of genes encoding small GTPases that are involved in cellular signal transduction. Activation of Ras signalling causes cell growth, differentiation and survival. Ras is the prototypical member of the Ras superfamily of proteins which are all related in structure and regulate diverse cell behaviours. Ras proteins function as binary molecular switches that control intracellular signaling networks. Ras-regulated signal pathways control such processes as actin cytoskeletal integrity, proliferation, differentiation, cell adhesion, apoptosis, and cell migration. Ras and ras-related proteins are often deregulated in cancers, leading to increased invasion and metastasis, and decreased apoptosis.

Since Ras communicates signals from outside the cell to the nucleus, mutations in ras genes can permanently activate it and cause inappropriate transmission inside the cell even in the absence of extracellular signals. Because these signals result in cell growth and division, dysregulated Ras signaling can ultimately lead to oncogenesis and cancer (Goodsell D S (1999). Oncologist 4 (3): 263-4). Activating mutations in Ras are found in 20-25% of all human tumors and up to 90% in specific tumor types (Downward J (January 2003). *Nat. Rev. Cancer* 3 (1): 11-22).

There are more than a hundred proteins in the Ras superfamily (Wennerberg et al., (March 2005). *J. Cell. Sci.* 118 (Pt 5): 843-6). Based on structure, sequence and function, the Ras superfamily is divided into eight main families, each of which is further divided into subfamilies: Ras, Rho, Rab, Rap, Arf, Ran, Rheb, Rad and Rit.

Each subfamily shares the common core G domain, which provides essential GTPase and nucleotide exchange activity. The surrounding sequence helps determine the functional specificity of the small GTPase, for example the 'Insert Loop', common to the Rho subfamily, specifically contributes to binding to effector proteins such as IQGAP and WASP.

The Ras family is generally responsible for cell proliferation, Rho for cell morphology, nuclear transport for Ran and vesicle transport for Rab and Arf (Munemitsu et al., (1990). *Mol Cell Biol* 10 (11): 5977-82). V-raf murine sarcoma viral oncogene homolog B1, also known as BRAF, is a protein which in humans is encoded by the BRAF gene (Sithanandam et al., (December 1990) Oncogene 5 (12): 1775-80; Sithanandam et al., (April 1992). Oncogene 7 (4): 795-9).

Human KRAS DNA has the nucleotide sequence described by Genbank Accession No. NG_007524. Human KRAS mRNA has the nucleotide sequence described by Genbank Accession No. NM_004985.

The BRAF gene makes a protein called B-RAF, which is involved in sending signals in cells and in cell growth. This gene may be mutated (Davies et al., (2002). *Nature* 417 (6892): 949-54) in many types of cancer, which causes a change in the B-RAF protein. This can increase the growth and spread of cancer cells.

This gene encodes a protein belonging to the raf/mil family of serine/threonine protein kinases. This protein plays a role in regulating the MAP kinase/ERKs signaling pathway, which affects cell division, differentiation, and secretion.

Mutations in this gene are associated with cardiofaciocutaneous syndrome, a disease characterized by heart defects, mental retardation and a distinctive facial appearance. Mutations in this gene have also been associated with various cancers, including non-Hodgkin lymphoma, colorectal cancer, malignant melanoma, thyroid carcinoma, non-small cell lung carcinoma, and adenocarcinoma of lung.

c-raf is gene that codes for a protein kinase called "Raf-1" here. The Raf-1 protein functions in the MAPK/ERK signal transduction pathway as part of a protein kinase cascade. Raf-1 is a serine/threonine-specific kinase. Raf-1 is a MAP kinase kinase kinase (MAP3K) which functions downstream of the Ras family of membrane associated GTPases to which it binds directly. Once activated Raf-1 can phosphorylate to activate the dual specificity protein kinases MEK1 and MEK2 which in turn phosphorylate to activate the serine/threonine specific protein kinases ERK1 and ERK2. Activated ERKs are pleiotropic effectors of cell physiology and play an important role in the control of gene expression involved in the cell division cycle, apoptosis, cell differentiation and cell migration.

The first raf gene that was found was the oncogene v-raf (Mark et al., (April 1984). *Science* 224 (4646): 285-9). Normal (non-oncogenic) cellular homologs of v-raf were soon found to be conserved components of eukaryotic genomes and it was shown that they could mutate and become oncogenes (Shimizu et al., (1986). *Int. Symp. Princess Takamatsu Cancer Res. Fund* 17: 85-91). A-Raf and B-Raf are two protein kinases with similar sequences to Raf-1. Mutations in B-Raf genes are found in several types of cancer. The Raf kinases are targets for anticancer drug development (Sridhar et al., (April 2005). *Mol. Cancer. Ther.* 4 (4): 677-85). There are several quantitative immunochemical methods available to detect Raf kinase inhibiting drugs (Olive (October 2004). Expert Rev Proteomics 1 (3): 327-41).

Human BRAF DNA has the nucleotide sequence described by Genbank Accession No. NG_007873. Human BRAF mRNA has the nucleotide sequence described by Genbank Accession No. NM_004333.

Human RAF1 DNA has the nucleotide sequence described by Genbank Accession No. NG_007467. Human RAF1 mRNA has the nucleotide sequence described by Genbank Accession No. NM_002880.

II. Antibodies

The gene fusion proteins of the present invention, including fragments, derivatives and analogs thereof, may be used as immunogens to produce antibodies having use in the diagnostic, research, and therapeutic methods described below. The antibodies may be polyclonal or monoclonal, chimeric, humanized, single chain or Fab fragments. Various procedures known to those of ordinary skill in the art may be used for the production and labeling of such antibodies and fragments. See, e.g., Burns, ed., *Immunochemical Protocols*, 3$^{rd}$ ed., Humana Press (2005); Harlow and Lane, *Antibodies: A Laboratory Manual*, Cold Spring Harbor Laboratory (1988); Kozbor et al., *Immunology Today* 4: 72 (1983); Köhler and Milstein, *Nature* 256: 495 (1975). Antibodies or fragments exploiting the differences between the truncated ETS family member protein or chimeric protein and their respective native proteins are particularly preferred.

III. Diagnostic Applications

The gene fusions described herein are detectable as DNA, RNA or protein. Initially, the gene fusion is detectable as a chromosomal rearrangement of genomic DNA having a 5' portion from a first gene and a 3' portion from a RAS or RAF family member gene. Once transcribed, the gene fusion is detectable as a chimeric mRNA having a 5' portion from a first gene and a 3' portion from a RAS or RAF family member gene. Once translated, the gene fusion is detectable as fusion of a 5' portion from a first protein and a 3' portion from a RAS or RAF family member protein or a truncated version of a first protein or a RAS or RAF family member. The truncated or fusion proteins may differ from their respective native proteins in amino acid sequence, post-translational processing and/or secondary, tertiary or quaternary structure. Such differences, if present, can be used to identify the presence of the gene fusion. Specific methods of detection are described in more detail below.

The present invention provides DNA, RNA and protein based diagnostic methods that either directly or indirectly detect the gene fusions. The present invention also provides compositions and kits for diagnostic purposes.

The diagnostic methods of the present invention may be qualitative or quantitative. Quantitative diagnostic methods may be used, for example, to discriminate between indolent and aggressive cancers via a cutoff or threshold level. Where applicable, qualitative or quantitative diagnostic methods may also include amplification of target, signal or intermediary (e.g., a universal primer).

An initial assay may confirm the presence of a gene fusion but not identify the specific fusion. A secondary assay is then performed to determine the identity of the particular fusion, if desired. The second assay may use a different detection technology than the initial assay.

The gene fusions of the present invention may be detected along with other markers in a multiplex or panel format. Markers are selected for their predictive value alone or in combination with the gene fusions. Exemplary prostate cancer markers include, but are not limited to: AMACR/P504S (U.S. Pat. No. 6,262,245); PCA3 (U.S. Pat. No. 7,008,765); PCGEM1 (U.S. Pat. No. 6,828,429); prostein/P501S, P503S, P504S, P509S, P510S, prostase/P703P, P710P (U.S. Publication No. 20030185830); and, those disclosed in U.S. Pat. Nos. 5,854,206 and 6,034,218, and U.S. Publication No. 20030175736, each of which is herein incorporated by reference in its entirety. Markers for other cancers, diseases, infections, and metabolic conditions are also contemplated for inclusion in a multiplex or panel format.

The diagnostic methods of the present invention may also be modified with reference to data correlating particular gene fusions with the stage, aggressiveness or progression of the disease or the presence or risk of metastasis. Ultimately, the information provided by the methods of the present invention will assist a physician in choosing the best course of treatment for a particular patient.

A. Sample

Any patient sample suspected of containing the gene fusions may be tested according to the methods of the present invention. By way of non-limiting examples, the sample may be tissue (e.g., a prostate biopsy sample or a tissue sample obtained by prostatectomy), blood, urine, semen, prostatic secretions or a fraction thereof (e.g., plasma, serum, urine supernatant, urine cell pellet or prostate cells). A urine sample is preferably collected immediately following an attentive digital rectal examination (DRE), which causes prostate cells from the prostate gland to shed into the urinary tract.

The patient sample typically requires preliminary processing designed to isolate or enrich the sample for the gene fusions or cells that contain the gene fusions. A variety of techniques known to those of ordinary skill in the art may be used for this purpose, including but not limited to: centrifugation; immunocapture; cell lysis; and, nucleic acid target capture (See, e.g., EP Pat. No. 1 409 727, herein incorporated by reference in its entirety).

B. DNA and RNA Detection

The gene fusions of the present invention may be detected as chromosomal rearrangements of genomic DNA or chimeric mRNA using a variety of nucleic acid techniques known to those of ordinary skill in the art, including but not limited to: nucleic acid sequencing; nucleic acid hybridization; and, nucleic acid amplification.

1. Sequencing

Illustrative non-limiting examples of nucleic acid sequencing techniques include, but are not limited to, chain terminator (Sanger) sequencing and dye terminator sequencing. Those of ordinary skill in the art will recognize that because RNA is less stable in the cell and more prone to nuclease attack experimentally RNA is usually reverse transcribed to DNA before sequencing.

Chain terminator sequencing uses sequence-specific termination of a DNA synthesis reaction using modified nucleotide substrates. Extension is initiated at a specific site on the template DNA by using a short radioactive, or other labeled, oligonucleotide primer complementary to the template at that region. The oligonucleotide primer is extended using a DNA polymerase, standard four deoxynucleotide bases, and a low concentration of one chain terminating nucleotide, most commonly a di-deoxynucleotide. This reaction is repeated in four separate tubes with each of the bases taking turns as the di-deoxynucleotide. Limited incorporation of the chain terminating nucleotide by the DNA polymerase results in a series of related DNA fragments that are terminated only at positions where that particular di-deoxynucleotide is used. For each reaction tube, the fragments are size-separated by electrophoresis in a slab polyacrylamide gel or a capillary tube filled with a viscous polymer. The sequence is determined by reading which lane produces a visualized mark from the labeled primer as you scan from the top of the gel to the bottom.

Dye terminator sequencing alternatively labels the terminators. Complete sequencing can be performed in a single reaction by labeling each of the di-deoxynucleotide chain-terminators with a separate fluorescent dye, which fluoresces at a different wavelength.

2. Hybridization

Illustrative non-limiting examples of nucleic acid hybridization techniques include, but are not limited to, in situ hybridization (ISH), microarray, and Southern or Northern blot.

In situ hybridization (ISH) is a type of hybridization that uses a labeled complementary DNA or RNA strand as a probe to localize a specific DNA or RNA sequence in a portion or section of tissue (in situ), or, if the tissue is small enough, the entire tissue (whole mount ISH). DNA ISH can be used to determine the structure of chromosomes. RNA ISH is used to measure and localize mRNAs and other transcripts within tissue sections or whole mounts. Sample cells and tissues are usually treated to fix the target transcripts in place and to increase access of the probe. The probe hybridizes to the target sequence at elevated temperature, and then the excess probe is washed away. The probe that was labeled with either radio-, fluorescent- or antigen-labeled bases is localized and quantitated in the tissue using either autoradiography, fluorescence microscopy or immunohistochemistry, respectively. ISH can also use two or more probes, labeled with radioactivity or the other non-radioactive labels, to simultaneously detect two or more transcripts.

a. Fish

In some embodiments, fusion sequences are detected using fluorescence in situ hybridization (FISH). The preferred FISH assays for the present invention utilize bacterial artificial chromosomes (BACs). These have been used extensively in the human genome sequencing project (see *Nature* 409: 953-958 (2001)) and clones containing specific BACs are available through distributors that can be located through many sources, e.g., NCBI. Each BAC clone from the human genome has been given a reference name that unambiguously identifies it. These names can be used to find a corresponding GenBank sequence and to order copies of the clone from a distributor.

The present invention further provides a method of performing a FISH assay on human prostate cells, human prostate tissue or on the fluid surrounding said human prostate cells or human prostate tissue.

b. Microarrays

Different kinds of biological assays are called microarrays including, but not limited to: DNA microarrays (e.g., cDNA microarrays and oligonucleotide microarrays); protein microarrays; tissue microarrays; transfection or cell microarrays; chemical compound microarrays; and, antibody microarrays. A DNA microarray, commonly known as gene chip, DNA chip, or biochip, is a collection of microscopic DNA spots attached to a solid surface (e.g., glass, plastic or silicon chip) forming an array for the purpose of expression profiling or monitoring expression levels for thousands of genes simultaneously. The affixed DNA segments are known as probes, thousands of which can be used in a single DNA microarray. Microarrays can be used to identify disease genes by comparing gene expression in disease and normal cells. Microarrays can be fabricated using a variety of technologies, including but not limiting: printing with fine-pointed pins onto glass slides; photolithography using pre-made masks; photolithography using dynamic micromirror devices; ink-jet printing; or, electrochemistry on microelectrode arrays.

Southern and Northern blotting is used to detect specific DNA or RNA sequences, respectively. DNA or RNA extracted from a sample is fragmented, electrophoretically separated on a matrix gel, and transferred to a membrane filter. The filter bound DNA or RNA is subject to hybridization with a labeled probe complementary to the sequence of interest. Hybridized probe bound to the filter is detected. A variant of the procedure is the reverse Northern blot, in which the substrate nucleic acid that is affixed to the membrane is a collection of isolated DNA fragments and the probe is RNA extracted from a tissue and labeled.

3. Amplification

Chromosomal rearrangements of genomic DNA and chimeric mRNA may be amplified prior to or simultaneous with detection. Illustrative non-limiting examples of nucleic acid amplification techniques include, but are not limited to, polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA). Those of ordinary skill in the art will recognize that certain amplification techniques (e.g., PCR) require that RNA be reversed transcribed to DNA prior to amplification (e.g., RT-PCR), whereas other amplification techniques directly amplify RNA (e.g., TMA and NASBA).

The polymerase chain reaction (U.S. Pat. Nos. 4,683,195, 4,683,202, 4,800,159 and 4,965,188, each of which is herein incorporated by reference in its entirety), commonly referred to as PCR, uses multiple cycles of denaturation, annealing of primer pairs to opposite strands, and primer extension to exponentially increase copy numbers of a target nucleic acid sequence. In a variation called RT-PCR, reverse transcriptase (RT) is used to make a complementary DNA (cDNA) from mRNA, and the cDNA is then amplified by PCR to produce multiple copies of DNA. For other various permutations of PCR see, e.g., U.S. Pat. Nos. 4,683,195, 4,683,202 and 4,800,159; Mullis et al., *Meth. Enzymol.* 155: 335 (1987); and, Murakawa et al., *DNA* 7: 287 (1988), each of which is herein incorporated by reference in its entirety.

Transcription mediated amplification (U.S. Pat. Nos. 5,480,784 and 5,399,491, each of which is herein incorporated by reference in its entirety), commonly referred to as TMA, synthesizes multiple copies of a target nucleic acid sequence autocatalytically under conditions of substantially constant temperature, ionic strength, and pH in which multiple RNA copies of the target sequence autocatalytically generate additional copies. See, e.g., U.S. Pat. Nos. 5,399, 491 and 5,824,518, each of which is herein incorporated by reference in its entirety. In a variation described in U.S. Publ. No. 20060046265 (herein incorporated by reference in its entirety), TMA optionally incorporates the use of blocking moieties, terminating moieties, and other modifying moieties to improve TMA process sensitivity and accuracy.

The ligase chain reaction (Weiss, R., *Science* 254: 1292 (1991), herein incorporated by reference in its entirety), commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Strand displacement amplification (Walker, G. et al., *Proc. Natl. Acad. Sci. USA* 89: 392-396 (1992); U.S. Pat. Nos. 5,270,184 and 5,455,166, each of which is herein incorporated by reference in its entirety), commonly referred to as SDA, uses cycles of annealing pairs of primer sequences to opposite strands of a target sequence, primer extension in the presence of a dNTPαS to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (EP Pat. No. 0 684 315).

Other amplification methods include, for example: nucleic acid sequence based amplification (U.S. Pat. No. 5,130,238, herein incorporated by reference in its entirety), commonly referred to as NASBA; one that uses an RNA replicase to amplify the probe molecule itself (Lizardi et al., *BioTechnol.* 6: 1197 (1988), herein incorporated by reference in its entirety), commonly referred to as Qβ replicase; a transcription based amplification method (Kwoh et al., *Proc. Natl. Acad. Sci. USA* 86:1173 (1989)); and, self-sustained sequence replication (Guatelli et al., *Proc. Natl. Acad. Sci. USA* 87: 1874 (1990), each of which is herein incorporated by reference in its entirety). For further discussion of known amplification methods see Persing, David H., "In Vitro Nucleic Acid Amplification Techniques" in *Diagnostic Medical Microbiology: Principles and Applications* (Persing et al., Eds.), pp. 51-87 (American Society for Microbiology, Washington, D.C. (1993)).

4. Detection Methods

Non-amplified or amplified gene fusion nucleic acids can be detected by any conventional means. For example, the gene fusions can be detected by hybridization with a detectably labeled probe and measurement of the resulting hybrids. Illustrative non-limiting examples of detection methods are described below.

One illustrative detection method, the Hybridization Protection Assay (HPA) involves hybridizing a chemiluminescent oligonucleotide probe (e.g., an acridinium ester-labeled (AE) probe) to the target sequence, selectively hydrolyzing the chemiluminescent label present on unhybridized probe, and measuring the chemiluminescence produced from the remaining probe in a luminometer. See, e.g., U.S. Pat. No. 5,283,174 and Norman C. Nelson et al., Nonisotopic Probing, Blotting, and Sequencing, ch. 17 (Larry J. Kricka ed., 2d ed. 1995, each of which is herein incorporated by reference in its entirety).

Another illustrative detection method provides for quantitative evaluation of the amplification process in real-time. Evaluation of an amplification process in "real-time" involves determining the amount of amplicon in the reaction mixture either continuously or periodically during the amplification reaction, and using the determined values to calculate the amount of target sequence initially present in the sample. A variety of methods for determining the amount of initial target sequence present in a sample based on real-time amplification are well known in the art. These include methods disclosed in U.S. Pat. Nos. 6,303,305 and 6,541,205, each of which is herein incorporated by reference in its entirety. Another method for determining the quantity of target sequence initially present in a sample, but which is not based on a real-time amplification, is disclosed in U.S. Pat. No. 5,710,029, herein incorporated by reference in its entirety.

Amplification products may be detected in real-time through the use of various self-hybridizing probes, most of which have a stem-loop structure. Such self-hybridizing probes are labeled so that they emit differently detectable signals, depending on whether the probes are in a self-hybridized state or an altered state through hybridization to a target sequence. By way of non-limiting example, "molecular torches" are a type of self-hybridizing probe that includes distinct regions of self-complementarity (referred to as "the target binding domain" and "the target closing domain") which are connected by a joining region (e.g., non-nucleotide linker) and which hybridize to each other under predetermined hybridization assay conditions. In a preferred embodiment, molecular torches contain single-stranded base regions in the target binding domain that are from 1 to about 20 bases in length and are accessible for hybridization to a target sequence present in an amplification reaction under strand displacement conditions. Under strand displacement conditions, hybridization of the two complementary regions, which may be fully or partially complementary, of the molecular torch is favored, except in the presence of the target sequence, which will bind to the single-stranded region present in the target binding domain and displace all or a portion of the target closing domain. The target binding domain and the target closing domain of a molecular torch include a detectable label or a pair of interacting labels (e.g., luminescent/quencher) positioned so that a different signal is produced when the molecular torch is self-hybridized than when the molecular torch is hybridized to the target sequence, thereby permitting detection of probe:target duplexes in a test sample in the presence of unhybridized molecular torches. Molecular torches and a variety of types of interacting label pairs are disclosed in U.S. Pat. No. 6,534,274, herein incorporated by reference in its entirety.

Another example of a detection probe having self-complementarity is a "molecular beacon." Molecular beacons include nucleic acid molecules having a target complementary sequence, an affinity pair (or nucleic acid arms) holding the probe in a closed conformation in the absence of a target sequence present in an amplification reaction, and a label pair that interacts when the probe is in a closed conformation. Hybridization of the target sequence and the target complementary sequence separates the members of the affinity pair, thereby shifting the probe to an open conformation. The shift to the open conformation is detectable due to reduced interaction of the label pair, which may be, for example, a fluorophore and a quencher (e.g., DAB-CYL and EDANS). Molecular beacons are disclosed in U.S. Pat. Nos. 5,925,517 and 6,150,097, herein incorporated by reference in its entirety.

Other self-hybridizing probes are well known to those of ordinary skill in the art. By way of non-limiting example, probe binding pairs having interacting labels, such as those disclosed in U.S. Pat. No. 5,928,862 (herein incorporated by reference in its entirety) might be adapted for use in the present invention. Probe systems used to detect single nucleotide polymorphisms (SNPs) might also be utilized in the present invention. Additional detection systems include "molecular switches," as disclosed in U.S. Publ. No. 20050042638, herein incorporated by reference in its entirety. Other probes, such as those comprising intercalating dyes and/or fluorochromes, are also useful for detection of amplification products in the present invention. See, e.g., U.S. Pat. No. 5,814,447 (herein incorporated by reference in its entirety).

C. Protein Detection

The gene fusions of the present invention may be detected as truncated or chimeric proteins using a variety of protein techniques known to those of ordinary skill in the art, including but not limited to: protein sequencing; and, immunoassays.

1. Sequencing

Illustrative non-limiting examples of protein sequencing techniques include, but are not limited to, mass spectrometry and Edman degradation.

Mass spectrometry can, in principle, sequence any size protein but becomes computationally more difficult as size increases. A protein is digested by an endoprotease, and the resulting solution is passed through a high pressure liquid chromatography column. At the end of this column, the solution is sprayed out of a narrow nozzle charged to a high positive potential into the mass spectrometer. The charge on the droplets causes them to fragment until only single ions remain. The peptides are then fragmented and the mass-charge ratios of the fragments measured. The mass spectrum is analyzed by computer and often compared against a database of previously sequenced proteins in order to determine the sequences of the fragments. The process is then repeated with a different digestion enzyme, and the overlaps in sequences are used to construct a sequence for the protein.

In the Edman degradation reaction, the peptide to be sequenced is adsorbed onto a solid surface (e.g., a glass fiber coated with polybrene). The Edman reagent, phenylisothiocyanate (PTC), is added to the adsorbed peptide, together with a mildly basic buffer solution of 12% trimethylamine, and reacts with the amine group of the N-terminal amino acid. The terminal amino acid derivative can then be selectively detached by the addition of anhydrous acid. The derivative isomerizes to give a substituted phenylthiohydantoin, which can be washed off and identified by chromatography, and the cycle can be repeated. The efficiency of each step is about 98%, which allows about 50 amino acids to be reliably determined.

2. Immunoassays

Illustrative non-limiting examples of immunoassays include, but are not limited to: immunoprecipitation; Western blot; ELISA; immunohistochemistry; immunocytochemistry; flow cytometry; and, immuno-PCR. Polyclonal or monoclonal antibodies detectably labeled using various techniques known to those of ordinary skill in the art (e.g., colorimetric, fluorescent, chemiluminescent or radioactive) are suitable for use in the immunoassays.

Immunoprecipitation is the technique of precipitating an antigen out of solution using an antibody specific to that antigen. The process can be used to identify protein complexes present in cell extracts by targeting a protein believed to be in the complex. The complexes are brought out of solution by insoluble antibody-binding proteins isolated initially from bacteria, such as Protein A and Protein G. The antibodies can also be coupled to sepharose beads that can easily be isolated out of solution. After washing, the precipitate can be analyzed using mass spectrometry, Western blotting, or any number of other methods for identifying constituents in the complex.

A Western blot, or immunoblot, is a method to detect protein in a given sample of tissue homogenate or extract. It uses gel electrophoresis to separate denatured proteins by mass. The proteins are then transferred out of the gel and onto a membrane, typically polyvinyldifluoride or nitrocellulose, where they are probed using antibodies specific to the protein of interest. As a result, researchers can examine the amount of protein in a given sample and compare levels between several groups.

An ELISA, short for Enzyme-Linked ImmunoSorbent Assay, is a biochemical technique to detect the presence of an antibody or an antigen in a sample. It utilizes a minimum of two antibodies, one of which is specific to the antigen and the other of which is coupled to an enzyme. The second antibody will cause a chromogenic or fluorogenic substrate to produce a signal. Variations of ELISA include sandwich ELISA, competitive ELISA, and ELISPOT. Because the ELISA can be performed to evaluate either the presence of antigen or the presence of antibody in a sample, it is a useful tool both for determining serum antibody concentrations and also for detecting the presence of antigen.

Immunohistochemistry and immunocytochemistry refer to the process of localizing proteins in a tissue section or cell, respectively, via the principle of antigens in tissue or cells binding to their respective antibodies. Visualization is enabled by tagging the antibody with color producing or fluorescent tags. Typical examples of color tags include, but are not limited to, horseradish peroxidase and alkaline phosphatase. Typical examples of fluorophore tags include, but are not limited to, fluorescein isothiocyanate (FITC) or phycoerythrin (PE).

Flow cytometry is a technique for counting, examining and sorting microscopic particles suspended in a stream of fluid. It allows simultaneous multiparametric analysis of the physical and/or chemical characteristics of single cells flowing through an optical/electronic detection apparatus. A beam of light (e.g., a laser) of a single frequency or color is directed onto a hydrodynamically focused stream of fluid. A number of detectors are aimed at the point where the stream passes through the light beam; one in line with the light beam (Forward Scatter or FSC) and several perpendicular to it (Side Scatter (SSC) and one or more fluorescent detectors). Each suspended particle passing through the beam scatters the light in some way, and fluorescent chemicals in the particle may be excited into emitting light at a lower frequency than the light source. The combination of scattered and fluorescent light is picked up by the detectors, and by analyzing fluctuations in brightness at each detector, one for each fluorescent emission peak, it is possible to deduce various facts about the physical and chemical structure of each individual particle. FSC correlates with the cell volume and SSC correlates with the density or inner complexity of the particle (e.g., shape of the nucleus, the amount and type of cytoplasmic granules or the membrane roughness).

Immuno-polymerase chain reaction (IPCR) utilizes nucleic acid amplification techniques to increase signal generation in antibody-based immunoassays. Because no protein equivalence of PCR exists, that is, proteins cannot be replicated in the same manner that nucleic acid is replicated during PCR, the only way to increase detection sensitivity is by signal amplification. The target proteins are bound to antibodies which are directly or indirectly conjugated to oligonucleotides. Unbound antibodies are washed away and the remaining bound antibodies have their oligonucleotides amplified. Protein detection occurs via detection of amplified oligonucleotides using standard nucleic acid detection methods, including real-time methods.

D. Data Analysis

In some embodiments, a computer-based analysis program is used to translate the raw data generated by the detection assay (e.g., the presence, absence, or amount of a given gene fusion or other markers) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression data), specific for the diagnostic or prognostic information desired for the subject.

The profile data is then prepared in a format suitable for interpretation by a treating clinician. For example, rather than providing raw expression data, the prepared format may represent a diagnosis or risk assessment (e.g., likelihood of cancer being present) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease.

E. In Vivo Imaging

The gene fusions of the present invention may also be detected using in vivo imaging techniques, including but not limited to: radionuclide imaging; positron emission tomography (PET); computerized axial tomography, X-ray or magnetic resonance imaging method, fluorescence detection, and chemiluminescent detection. In some embodiments, in vivo imaging techniques are used to visualize the presence of or expression of cancer markers in an animal (e.g., a human or non-human mammal). For example, in some embodiments, cancer marker mRNA or protein is labeled using a labeled antibody specific for the cancer marker. A specifically bound and labeled antibody can be detected in an individual using an in vivo imaging method, including, but not limited to, radionuclide imaging, positron emission tomography, computerized axial tomography, X-ray or magnetic resonance imaging method, fluorescence detection, and chemiluminescent detection. Methods for generating antibodies to the cancer markers of the present invention are described below.

The in vivo imaging methods of the present invention are useful in the diagnosis of cancers that express the cancer markers of the present invention (e.g., prostate cancer). In vivo imaging is used to visualize the presence of a marker indicative of the cancer. Such techniques allow for diagnosis without the use of an unpleasant biopsy. The in vivo imaging methods of the present invention are also useful for providing prognoses to cancer patients. For example, the presence of a marker indicative of cancers likely to metastasize can be detected. The in vivo imaging methods of the present invention can further be used to detect metastatic cancers in other parts of the body.

In some embodiments, reagents (e.g., antibodies) specific for the cancer markers of the present invention are fluorescently labeled. The labeled antibodies are introduced into a subject (e.g., orally or parenterally). Fluorescently labeled antibodies are detected using any suitable method (e.g., using the apparatus described in U.S. Pat. No. 6,198,107, herein incorporated by reference).

In other embodiments, antibodies are radioactively labeled. The use of antibodies for in vivo diagnosis is well known in the art. Sumerdon et al., (Nucl. Med. Biol 17:247-254 [1990] have described an optimized antibody-chelator for the radioimmunoscintographic imaging of tumors using Indium-111 as the label. Griffin et al., (J Clin One 9:631-640 [1991]) have described the use of this agent in detecting tumors in patients suspected of having recurrent colorectal cancer. The use of similar agents with paramagnetic ions as labels for magnetic resonance imaging is known in the art (Lauffer, Magnetic Resonance in Medicine 22:339-342 [1991]). The label used will depend on the imaging modality chosen. Radioactive labels such as Indium-111, Technetium-99m, or Iodine-131 can be used for planar scans or single photon emission computed tomography (SPECT). Positron emitting labels such as Fluorine-19 can also be used for positron emission tomography (PET). For MRI, paramagnetic ions such as Gadolinium (III) or Manganese (II) can be used.

Radioactive metals with half-lives ranging from 1 hour to 3.5 days are available for conjugation to antibodies, such as scandium-47 (3.5 days) gallium-67 (2.8 days), gallium-68 (68 minutes), technetiium-99m (6 hours), and indium-111 (3.2 days), of which gallium-67, technetium-99m, and indium-111 are preferable for gamma camera imaging, gallium-68 is preferable for positron emission tomography.

A useful method of labeling antibodies with such radiometals is by means of a bifunctional chelating agent, such as diethylenetriaminepentaacetic acid (DTPA), as described, for example, by Khaw et al. (Science 209:295 [1980]) for In-111 and Tc-99m, and by Scheinberg et al. (Science 215:1511 [1982]). Other chelating agents may also be used, but the 1-(p-carboxymethoxybenzyl) EDTA and the carboxycarbonic anhydride of DTPA are advantageous because their use permits conjugation without affecting the antibody's immunoreactivity substantially.

Another method for coupling DPTA to proteins is by use of the cyclic anhydride of DTPA, as described by Hnatowich et al. (Int. J. Appl. Radiat. Isot. 33:327 [1982]) for labeling of albumin with In-111, but which can be adapted for labeling of antibodies. A suitable method of labeling antibodies with Tc-99m which does not use chelation with DPTA is the pretinning method of Crockford et al., (U.S. Pat. No. 4,323,546, herein incorporated by reference).

A preferred method of labeling immunoglobulins with Tc-99m is that described by Wong et al. (Int. J. Appl. Radiat. Isot., 29:251 [1978]) for plasma protein, and recently applied successfully by Wong et al. (J. Nucl. Med., 23:229 [1981]) for labeling antibodies.

In the case of the radiometals conjugated to the specific antibody, it is likewise desirable to introduce as high a proportion of the radiolabel as possible into the antibody molecule without destroying its immunospecificity. A further improvement may be achieved by effecting radiolabeling in the presence of the specific cancer marker of the present invention, to insure that the antigen binding site on the antibody will be protected. The antigen is separated after labeling.

In still further embodiments, in vivo biophotonic imaging (Xenogen, Almeda, Calif.) is utilized for in vivo imaging. This real-time in vivo imaging utilizes luciferase. The luciferase gene is incorporated into cells, microorganisms, and animals (e.g., as a fusion protein with a cancer marker of the present invention). When active, it leads to a reaction that emits light. A CCD camera and software is used to capture the image and analyze it.

F. Compositions & Kits

Any of these compositions, alone or in combination with other compositions of the present invention, may be provided in the form of a kit. For example, the single labeled probe and pair of amplification oligonucleotides may be provided in a kit for the amplification and detection of gene fusions of the present invention. Kits may further comprise appropriate controls and/or detection reagents. The probe and antibody compositions of the present invention may also be provided in the form of an array.

Compositions for use in the diagnostic methods of the present invention include, but are not limited to, probes, amplification oligonucleotides, and antibodies. Particularly preferred compositions detect a product only when an first gene fuses to a RAS or RAF family member gene. These compositions include: a single labeled probe comprising a sequence that hybridizes to the junction at which a 5' portion from a first gene fuses to a 3' portion from a RAS or RAF family member gene (i.e., spans the gene fusion junction); a pair of amplification oligonucleotides wherein the first amplification oligonucleotide comprises a sequence that hybridizes to a transcriptional regulatory region of a 5' portion from a first gene fuses to a 3' portion from a RAS or RAF family member gene; an antibody to an amino-terminally truncated protein resulting from a fusion of a first protein to a RAS or RAF family member gene; or, an antibody to a chimeric protein having an amino-terminal portion from a first gene and a carboxy-terminal portion from a RAS or RAF family member gene. Other useful compositions, however, include: a pair of labeled probes wherein the first labeled probe comprises a sequence that hybridizes to a transcriptional regulatory region of a first gene and the second labeled probe comprises a sequence that hybridizes to a RAS or RAF family member gene.

IV. Drug Screening Applications

In some embodiments, the present invention provides drug screening assays (e.g., to screen for anticancer drugs). The screening methods of the present invention utilize cancer markers identified using the methods of the present invention (e.g., including but not limited to, gene fusions of the present invention). For example, in some embodiments, the present invention provides methods of screening for compounds that alter (e.g., decrease) the expression of gene fusions. The compounds or agents may interfere with transcription, by interacting, for example, with the promoter region. The compounds or agents may interfere with mRNA produced from the fusion (e.g., by RNA interference, antisense technologies, etc.). The compounds or agents may interfere with pathways that are upstream or downstream of the biological activity of the fusion. In some embodiments, candidate compounds are antisense or interfering RNA agents (e.g., oligonucleotides) directed against cancer markers. In other embodiments, candidate compounds are antibodies or small molecules that specifically bind to a cancer marker regulator or expression products of the present invention and inhibit its biological function.

In one screening method, candidate compounds are evaluated for their ability to alter cancer marker expression by contacting a compound with a cell expressing a cancer marker and then assaying for the effect of the candidate compounds on expression. In some embodiments, the effect of candidate compounds on expression of a cancer marker gene is assayed for by detecting the level of cancer marker mRNA expressed by the cell. mRNA expression can be detected by any suitable method.

In other embodiments, the effect of candidate compounds on expression of cancer marker genes is assayed by measuring the level of polypeptide encoded by the cancer markers. The level of polypeptide expressed can be measured using any suitable method, including but not limited to, those disclosed herein.

Specifically, the present invention provides screening methods for identifying modulators, i.e., candidate or test compounds or agents (e.g., proteins, peptides, peptidomimetics, peptoids, small molecules or other drugs) which bind to cancer markers of the present invention, have an inhibitory (or stimulatory) effect on, for example, cancer marker expression or cancer marker activity, or have a stimulatory or inhibitory effect on, for example, the expression or activity of a cancer marker substrate. Compounds thus identified can be used to modulate the activity of target gene products (e.g., cancer marker genes) either directly or indirectly in a therapeutic protocol, to elaborate the biological function of the target gene product, or to identify compounds that disrupt normal target gene interactions. Compounds that inhibit the activity or expression of cancer markers are useful in the treatment of proliferative disorders, e.g., cancer, particularly prostate cancer.

In one embodiment, the invention provides assays for screening candidate or test compounds that are substrates of a cancer marker protein or polypeptide or a biologically active portion thereof. In another embodiment, the invention provides assays for screening candidate or test compounds that bind to or modulate the activity of a cancer marker protein or polypeptide or a biologically active portion thereof.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 [1993]; Erb et al., Proc. Nad. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33.2059 [1994]; Carell et al., Angew. Chem. Int. Ed. Engl. 33:2061 [1994]; and Gallop et al., J. Med. Chem. 37:1233 [1994].

Libraries of compounds may be presented in solution (e.g., Houghten, Biotechniques 13:412-421 [1992]), or on beads (Lam, Nature 354:82-84 [1991]), chips (Fodor, Nature 364:555-556 [1993]), bacteria or spores (U.S. Pat. No. 5,223,409; herein incorporated by reference), plasmids (Cull et al., Proc. Nad. Acad. Sci. USA 89:18651869 [1992]) or on phage (Scott and Smith, Science 249:386-390 [1990]; Devlin Science 249:404-406 [1990]; Cwirla et al., Proc. Natl. Acad. Sci. 87:6378-6382 [1990]; Felici, J. Mol. Biol. 222: 301 [1991]).

In one embodiment, an assay is a cell-based assay in which a cell that expresses a cancer marker mRNA or protein or biologically active portion thereof is contacted with a test compound, and the ability of the test compound to the modulate cancer marker's activity is determined. Determining the ability of the test compound to modulate cancer marker activity can be accomplished by monitoring, for example, changes in enzymatic activity, destruction or mRNA, or the like.

The ability of the test compound to modulate cancer marker binding to a compound, e.g., a cancer marker substrate or modulator, can also be evaluated. This can be accomplished, for example, by coupling the compound, e.g., the substrate, with a radioisotope or enzymatic label such that binding of the compound, e.g., the substrate, to a cancer marker can be determined by detecting the labeled compound, e.g., substrate, in a complex.

Alternatively, the cancer marker is coupled with a radioisotope or enzymatic label to monitor the ability of a test compound to modulate cancer marker binding to a cancer marker substrate in a complex. For example, compounds (e.g., substrates) can be labeled with $^{125}I$, $^{35}S^{14}C$ or $^{3}H$, either directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a cancer marker substrate) to interact with a cancer marker with or without the labeling of any of the interactants can be evaluated. For example, a microphysiometer can be used to detect the interaction of a compound with a cancer marker without the labeling of either the compound or the cancer marker (McConnell et al. Science 257:1906-1912 [1992]). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and cancer markers.

In yet another embodiment, a cell-free assay is provided in which a cancer marker protein or biologically active portion thereof is contacted with a test compound and the ability of the test compound to bind to the cancer marker protein, mRNA, or biologically active portion thereof is evaluated. Preferred biologically active portions of the cancer marker proteins or mRNA to be used in assays of the present invention include fragments that participate in interactions with substrates or other proteins, e.g., fragments with high surface probability scores.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FRET) (see, for example, Lakowicz et al., U.S. Pat. No. 5,631,169; Stavrianopoulos et al., U.S. Pat. No. 4,968,103; each of which is herein incorporated by reference). A fluorophore label is selected such that a first donor molecule's emitted fluorescent energy will be absorbed by a fluorescent label on a second, 'acceptor' molecule, which in turn is able to fluoresce due to the absorbed energy.

Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label should be maximal. A FRET binding event can be conveniently measured through standard fluorometric detection means well known in the art (e.g., using a fluorimeter).

In another embodiment, determining the ability of the cancer marker protein or mRNA to bind to a target molecule can be accomplished using real-time Biomolecular Interaction Analysis (BIA) (see, e.g., Sjolander and Urbaniczky, Anal. Chem. 63:2338-2345 [1991] and Szabo et al. Curr. Opin. Struct. Biol. 5:699-705 [1995]). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal that can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize cancer markers, an anti-cancer marker antibody or its target molecule to facilitate separation of complexed from non-complexed forms of one or both of the proteins, as well as to accommodate automation of the assay. Binding of a test compound to a cancer marker protein, or interaction of a cancer marker protein with a target molecule in the presence and absence of a candidate compound, can be accomplished in any vessel suitable for containing the reactants. Examples of such vessels include microtiter plates, test tubes, and microcentrifuge tubes. In one embodiment, a fusion protein can be provided which adds a domain that allows one or both of the proteins to be bound to a matrix. For example, glutathione-S-transferase-cancer marker fusion proteins or glutathione-S-transferase/target fusion proteins can be adsorbed onto glutathione Sepharose beads (Sigma Chemical, St. Louis, Mo.) or glutathione-derivatized microtiter plates, which are then combined with the test compound or the test compound and either the non-adsorbed target protein or cancer marker protein, and the mixture incubated under conditions conducive for complex formation (e.g., at physiological conditions for salt and pH). Following incubation, the beads or microtiter plate wells are washed to remove any unbound components, the matrix immobilized in the case of beads, complex determined either directly or indirectly, for example, as described above.

Alternatively, the complexes can be dissociated from the matrix, and the level of cancer markers binding or activity determined using standard techniques. Other techniques for immobilizing either cancer markers protein or a target molecule on matrices include using conjugation of biotin and streptavidin. Biotinylated cancer marker protein or target molecules can be prepared from biotin-NHS (N-hydroxy-succinimide) using techniques known in the art (e.g., biotinylation kit, Pierce Chemicals, Rockford, EL), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-IgG antibody).

This assay is performed utilizing antibodies reactive with cancer marker protein or target molecules but which do not interfere with binding of the cancer markers protein to its target molecule. Such antibodies can be derivatized to the wells of the plate, and unbound target or cancer markers protein trapped in the wells by antibody conjugation. Methods for detecting such complexes, in addition to those described above for the GST-immobilized complexes, include immunodetection of complexes using antibodies reactive with the cancer marker protein or target molecule, as well as enzyme-linked assays which rely on detecting an enzymatic activity associated with the cancer marker protein or target molecule.

Alternatively, cell free assays can be conducted in a liquid phase. In such an assay, the reaction products are separated from unreacted components, by any of a number of standard techniques, including, but not limited to: differential centrifugation (see, for example, Rivas and Minton, Trends Biochem Sci 18:284-7 [1993]); chromatography (gel filtration chromatography, ion-exchange chromatography); electrophoresis (see, e.g., Ausubel et al., eds. Current Protocols in Molecular Biology 1999, J. Wiley: New York.); and immunoprecipitation (see, for example, Ausubel et al., eds. Current Protocols in Molecular Biology 1999, J. Wiley: New York). Such resins and chromatographic techniques are known to one skilled in the art (See e.g., Heegaard J. Mol. Recognit. 11:141-8 [1998]; Hageand Tweed J. Chromatogr. Biomed. Sci. Appl 699:499-525 [1997]). Further, fluorescence energy transfer may also be conveniently utilized, as described herein, to detect binding without further purification of the complex from solution.

The assay can include contacting the cancer markers protein, mRNA, or biologically active portion thereof with a known compound that binds the cancer marker to form an assay mixture, contacting the assay mixture with a test compound, and determining the ability of the test compound to interact with a cancer marker protein or mRNA, wherein determining the ability of the test compound to interact with a cancer marker protein or mRNA includes determining the ability of the test compound to preferentially bind to cancer markers or biologically active portion thereof, or to modulate the activity of a target molecule, as compared to the known compound.

To the extent that cancer markers can, in vivo, interact with one or more cellular or extracellular macromolecules, such as proteins, inhibitors of such an interaction are useful. A homogeneous assay can be used can be used to identify inhibitors.

For example, a preformed complex of the target gene product and the interactive cellular or extracellular binding partner product is prepared such that either the target gene products or their binding partners are labeled, but the signal generated by the label is quenched due to complex formation (see, e.g., U.S. Pat. No. 4,109,496, herein incorporated by reference, that utilizes this approach for immunoassays). The addition of a test substance that competes with and displaces one of the species from the preformed complex will result in the generation of a signal above background. In this way, test substances that disrupt target gene product-binding partner interaction can be identified. Alternatively, cancer markers protein can be used as a "bait protein" in a two-hybrid assay or three-hybrid assay (see, e.g., U.S. Pat. No. 5,283,317; Zervos et al., Cell 72:223-232 [1993]; Madura et al., J. Biol. Chem. 268.12046-12054 [1993]; Bartel et al., Biotechniques 14:920-924 [1993]; Iwabuchi et al., Oncogene 8:1693-1696 [1993]; and Brent WO 94/10300; each of which is herein incorporated by reference), to identify other proteins, that bind to or interact with cancer markers ("cancer marker-binding proteins" or "cancer marker-bp") and are involved in cancer marker activity. Such cancer marker-bps can be activators or inhibitors of signals by the cancer marker proteins or targets as, for example, downstream elements of a cancer markers-mediated signaling pathway.

Modulators of cancer markers expression can also be identified. For example, a cell or cell free mixture is contacted with a candidate compound and the expression of cancer marker mRNA or protein evaluated relative to the level of expression of cancer marker mRNA or protein in the absence of the candidate compound. When expression of cancer marker mRNA or protein is greater in the presence of the candidate compound than in its absence, the candidate compound is identified as a stimulator of cancer marker mRNA or protein expression. Alternatively, when expression of cancer marker mRNA or protein is less (i.e., statistically significantly less) in the presence of the candidate compound than in its absence, the candidate compound is identified as an inhibitor of cancer marker mRNA or protein expression. The level of cancer markers mRNA or protein expression can be determined by methods described herein for detecting cancer markers mRNA or protein.

A modulating agent can be identified using a cell-based or a cell free assay, and the ability of the agent to modulate the activity of a cancer markers protein can be confirmed in vivo, e.g., in an animal such as an animal model for a disease (e.g., an animal with prostate cancer or metastatic prostate cancer; or an animal harboring a xenograft of a prostate cancer from an animal (e.g., human) or cells from a cancer resulting from metastasis of a prostate cancer (e.g., to a lymph node, bone, or liver), or cells from a prostate cancer cell line.

This invention further pertains to novel agents identified by the above-described screening assays (See e.g., below description of cancer therapies). Accordingly, it is within the scope of this invention to further use an agent identified as described herein (e.g., a cancer marker modulating agent, an antisense cancer marker nucleic acid molecule, a siRNA molecule, a cancer marker specific antibody, or a cancer marker-binding partner) in an appropriate animal model (such as those described herein) to determine the efficacy, toxicity, side effects, or mechanism of action, of treatment with such an agent. Furthermore, novel agents identified by the above-described screening assays can be, e.g., used for treatments as described herein.

V. Transgenic Animals

The present invention contemplates the generation of transgenic animals comprising an exogenous cancer marker gene (e.g., gene fusion) of the present invention or mutants and variants thereof (e.g., truncations or single nucleotide polymorphisms). In preferred embodiments, the transgenic animal displays an altered phenotype (e.g., increased or decreased presence of markers) as compared to wild-type animals. Methods for analyzing the presence or absence of such phenotypes include but are not limited to, those disclosed herein. In some preferred embodiments, the transgenic animals further display an increased or decreased growth of tumors or evidence of cancer.

The transgenic animals of the present invention find use in drug (e.g., cancer therapy) screens. In some embodiments, test compounds (e.g., a drug that is suspected of being useful to treat cancer) and control compounds (e.g., a placebo) are administered to the transgenic animals and the control animals and the effects evaluated.

The transgenic animals can be generated via a variety of methods. In some embodiments, embryonal cells at various developmental stages are used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter that allows reproducible injection of 1-2 picoliters (pl) of DNA solution. The use of zygotes as a target for gene transfer has a major advantage in that in most cases the injected DNA will be incorporated into the host genome before the first cleavage (Brinster et al., Proc. Natl. Acad. Sci. USA 82:4438-4442 [1985]). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873,191 describes a method for the micro-injection of zygotes; the disclosure of this patent is incorporated herein in its entirety.

In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich, Proc. Natl. Acad. Sci. USA 73:1260 [1976]). Efficient infection of the blastomeres is obtained by enzymatic treatment to remove the zona pellucida (Hogan et al., in *Manipulating the Mouse Embryo*, Cold Spring Harbor Laboratory Press, Cold Spring Harbor, N.Y. [1986]). The viral vector system used to introduce the transgene is typically a replication-defective retrovirus carrying the transgene (Jahner et al., Proc. Natl. Acad. Sci. USA 82:6927 [1985]). Transfection is easily and efficiently obtained by culturing the blastomeres on a monolayer of virus-producing cells (Stewart, et al., EMBO J., 6:383 [1987]). Alternatively, infection can be performed at a later stage. Virus or virus-producing cells can be injected into the blastocoele (Jahner et al., Nature 298:623 [1982]). Most of the founders will be mosaic for the transgene since incorporation occurs only in a subset of cells that form the transgenic animal. Further, the founder may contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner et al., supra [1982]). Additional means of using retroviruses or retroviral vectors to create transgenic animals known to the art involve the micro-injection of retroviral particles or mitomycin C-treated cells producing retrovirus into the perivitelline space of fertilized eggs or early embryos (PCT International Application WO 90/08832 [1990], and Haskell and Bowen, Mol. Reprod. Dev., 40:386 [1995]).

In other embodiments, the transgene is introduced into embryonic stem cells and the transfected stem cells are utilized to form an embryo. ES cells are obtained by culturing pre-implantation embryos in vitro under appropriate conditions (Evans et al., Nature 292:154 [1981]; Bradley et al., Nature 309:255 [1984]; Gossler et al., Proc. Acad. Sci. USA 83:9065 [1986]; and Robertson et al., Nature 322:445 [1986]). Transgenes can be efficiently introduced into the ES cells by DNA transfection by a variety of methods known to the art including calcium phosphate co-precipitation, protoplast or spheroplast fusion, lipofection and DEAE-dextran-mediated transfection.

Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science 240:1468 [1988]). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells that have integrated the transgene. This technique obviates the need for growth of the transfected ES cells under appropriate selective conditions prior to transfer into the blastocoel.

In still other embodiments, homologous recombination is utilized to knock-out gene function or create deletion mutants (e.g., truncation mutants). Methods for homologous recombination are described in U.S. Pat. No. 5,614,396, incorporated herein by reference.

EXPERIMENTAL

The following examples are provided in order to demonstrate and further illustrate certain preferred embodiments and aspects of the present invention and are not to be construed as limiting the scope thereof.

Example 1

RAF Gene Fusions

Materials and Methods
Cloning of Full Length Fusion Transcript

The full length fusion transcript SLC45A3-BRAF and RAF1-ESRP1 were cloned into pCR8/GW/TOPO Entry vector (Invitrogen, USA) by TA cloning method following manufacturer's instructions. The fusion transcripts were later recombined into Gateway pcDNADEST40 mammalian expression vector (Invitrogen, USA) and into pAd/CMV/V5-DEST Adenoviral expression system (Invitrogen, USA) by LR Clonase II enzyme reaction following manufacturer's instruction.
Western Blotting The ESRP1-RAF1 fusion positive prostate cancer tissue and fusion negative tissues were homogenized in NP40 lysis buffer (50 mM Tris-HCl, 1% NP40, pH 7.4, Sigma, St. Louis, Mo.), and complete protease inhibitor mixture (Roche, Indianapolis, Ind.) and phosphatase inhibitor (EMD bioscience, San Diego. Calif.). For testing the expression and assess the molecular weight of the fusion protein in the fusion positive tissues, HEK293 cells were transfected with ESRP1-RAF1 fusion construct (cloned in pDEST40 expression vector—Invitrogen, Carlsbad Calif.) and vector control and lysed in NP40 lysis buffer with protease inhibitor. Fifteen micrograms of each protein extract were boiled in sample buffer, separated by SDS-PAGE, and transferred onto Polyvinylidene Difluoride membrane (GE Healthcare, Piscataway, N.J.). The membrane was incubated for one hour in blocking buffer (Tris-buffered saline, 0.1% Tween (TBS-T), 5% nonfat dry milk) and incubated overnight at 4° C. with anti-RAFT mouse monoclonal antibody (1:1000 in blocking buffer, BD bioscience, San Jose, Calif., Cat #: 610151). Following three washes with TBS-T, the blot was incubated with horseradish peroxidase-conjugated secondary antibody and the signals visualized by enhanced chemiluminescence system as described by the manufacturer (GE Healthcare). The blot was reprobed with anti-beta actin mouse monoclonal (1:5000, Sigma Cat #: A5441) antibodies.

Foci Formation Assay

Transfections were performed using Fugene 6 according to the manufacturer's protocol (Roche Applied Sciences). NIH3T3 cells ($1.5\times10^5$) in 35-mm plastic dishes were transfected with 2 μg of DNA of the plasmid of interest. Plasmids for fusion transcripts SLC45A3-Braf, exon8-Braf, exon10-Braf and mutant V600E were used along with control plasmids (pDEST40 and pBABE respectively). Three days after transfection, cells were split into 140-mm dishes containing DMEM with 5% CS (Life Technologies). The cultures were fed every 3-4 days. After 3 weeks, the cells cultured in DMEM with 5% CS were stained with 0.2% crystal violet in 70% ethanol for the visualization of foci, and were counted on colony counter (Oxford Optronix Ltd., Oxford UK, software v4.1, 2003). Foci counts were further confirmed manually.

WST-1 Assay

For each treatment, equal amount of cells were plated into 96-well plates for WST-1 assay, Boyden invasion chambers for invasion assay. WST-1 proliferation assay was performed using manufacturer's protocol (Roche, Indianapolis, Ind., USA). Invasion assay was performed as described previously (Kleer et al. PNAS 2003, Cao et al. Oncogene 2008).

BRAF Codon V600E Mutation Detection by Pyrosequencing

One to two μg total RNA isolated from fresh frozen localized prostate cancer (n=42), metastatic prostate cancer (n=21) and benign prostate (n=5) tissue samples, and a panel of melanoma (11), pancreatic (8) and breast cancer (8) cell lines was converted into cDNA using Superscript II Reverse Transcriptase (Invitrogen) according to manufacturer's instructions. Biotinylated sequencing templates were generated by PCR amplification of a 375 bp fragment spanning the mutation in codon 600 (V600E, Exon 15) of the BRAF gene using primers from PyroMark Q24 BRAF kit (Biotage-Qiagen) according to manufacturer's instructions. Ten microliters of the biotinylated PCR products were immobilized on streptavidin coated Sepharose beads (Streptavidin Sepharose High Performance, GE Healthcare) using Pyromark Q24 Vacuum Prep Workstation, followed by removal of non-biotinylated strand by sodium hydroxide denaturation followed by wash in neutralization buffer and 70% ethanol. The single stranded biotinylated templates were then mixed with 0.3 mM sequencing primer and 'sequencing by synthesis' was carried out through dispensation of the query nucleotide sequence using PyroMark Q24 platform, as described before (Edlundh-Rose, Egyhazi et al. Melanoma Res. 16:471 2006; Spittle, Ward et al. J. Mol. Diagn. 9:464 2007). The nucleotide sequence ACAGA/TGAAA (SEQ Id NO:4) for codon 600 was analyzed and visualized by Pyromark Q24 1.0.10 software. A panel of 9 melanoma cell lines (sk-mel-2, sk-mel-5, sk-mel-19, sk-mel-28, sk-mel-29, sk-mel-103, G-361, Malme-3M, mel-1 with known mutation status was used to serve as assay standards.

Real Time PCR Validation

Quantitative PCR (QPCR) was performed using Power SYBR Green Mastermix (Applied Biosystems, Foster City, Calif.) on an Applied Biosystems Step One Plus Real Time PCR System. All oligonucleotide primers were obtained from Integrated DNA Technologies (Coralville, Iowa) and are listed in Table 3. The GAPDH primer was used as a control. All assays were performed repeated twice and results were plotted as average fold change relative to GAPDH.

Fluorescence In Situ Hybridization (FISH)

FISH hybridizations were performed on tumor cells using prostate cancer tissue microarray (TMA) and individual sections. BAC clones were selected from UCSC genome browser and purchased through BACPAC resources (Children's Hospital, Oakland, Calif.). Following colony purification midi prep DNA was prepared using QiagenTips-100 (Qiagen, USA). DNA was labeled by nick translation method with biotin-16-dUTP and digoxigenin-11-dUTP (Roche, USA). Probe DNA was precipitated and dissolved in hybridization mixture containing 50% formamide, 2×SSC, 10% dextran sulphate, and 1% Denhardts solution. About 200 ng of labeled probes was hybridized to normal human chromosomes to confirm the map position of each BAC clone. FISH signals were obtained using anti digoxigenin-fluorescein and alexa fluor594 conjugate to obtain green and red colors respectively. Fluorescence images were captured using a high resolution CCD camera controlled by ISIS image processing software (Metasystems, Germany).

Results

Figure 10:
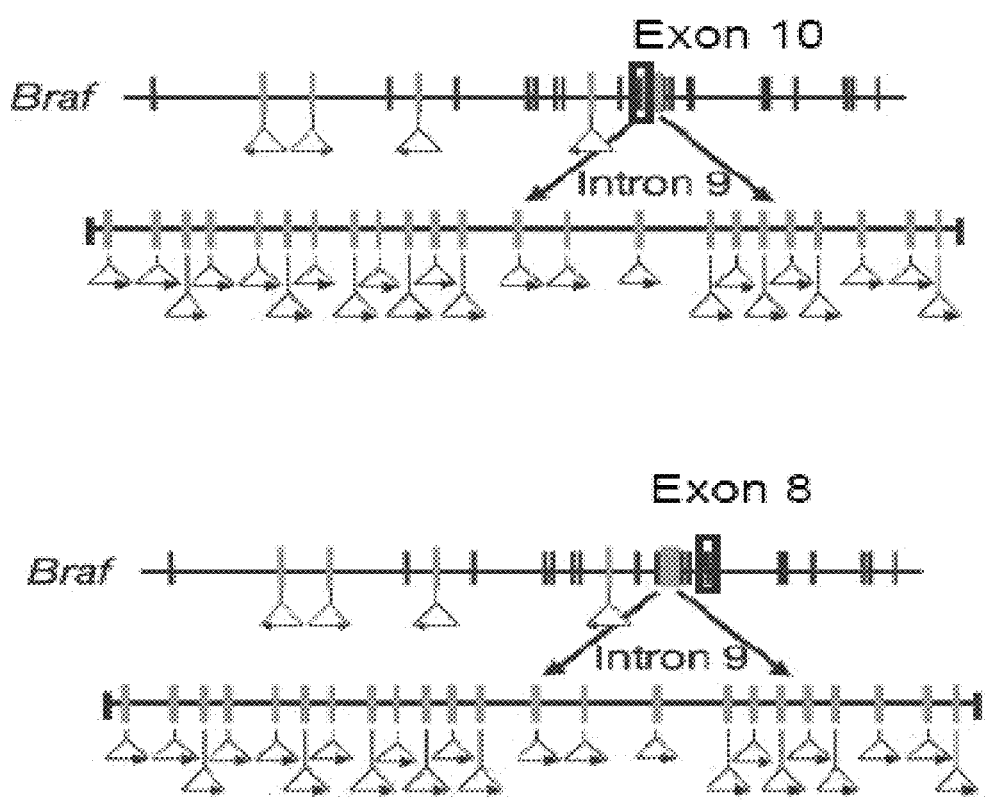
FIG. 10 shows truncated BRAF and BRAF fusion transcripts.
Figure 11:
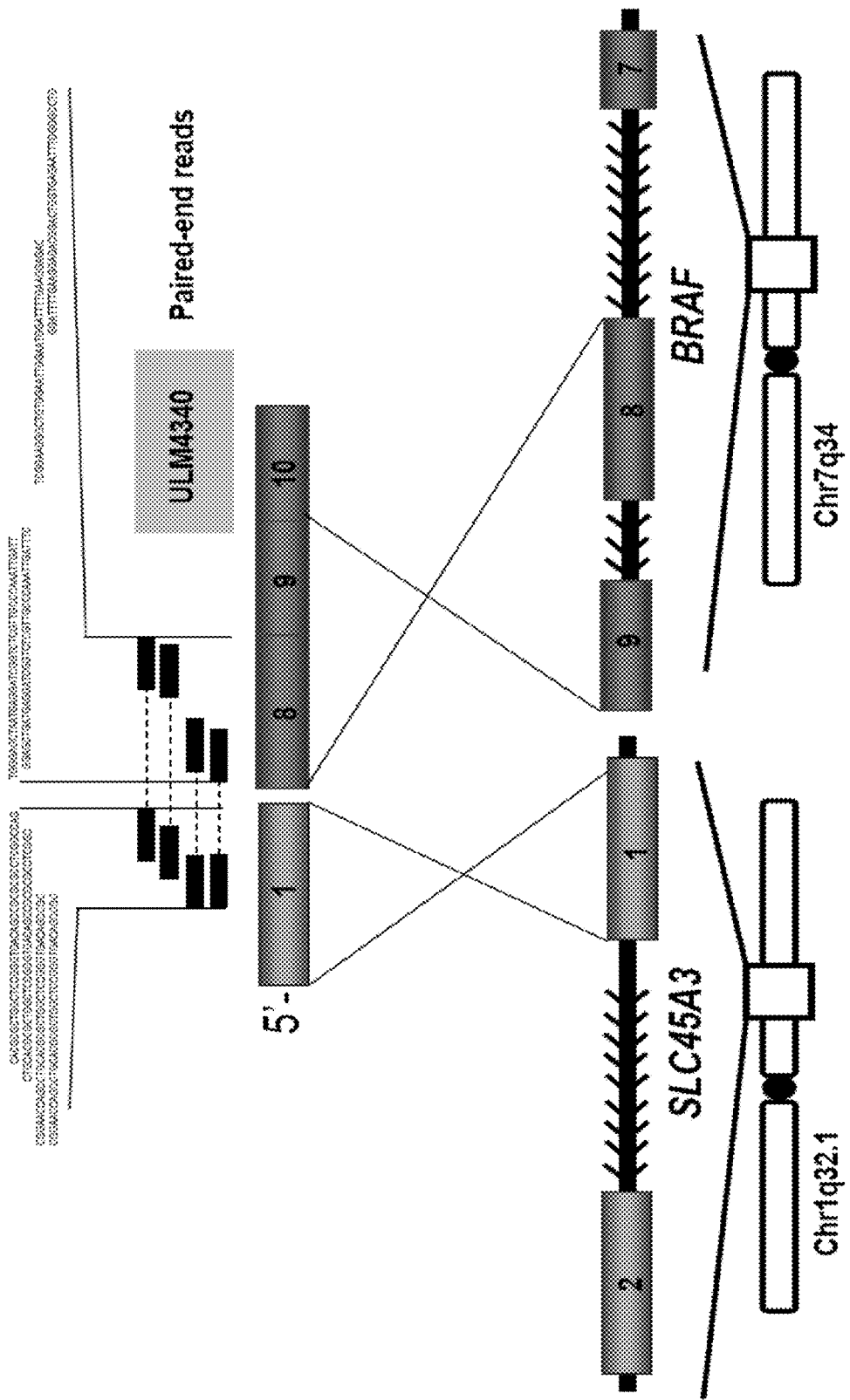
FIG. 11 shows a schematic of a SLC45A3-BRAF fusion.
Figure 12:
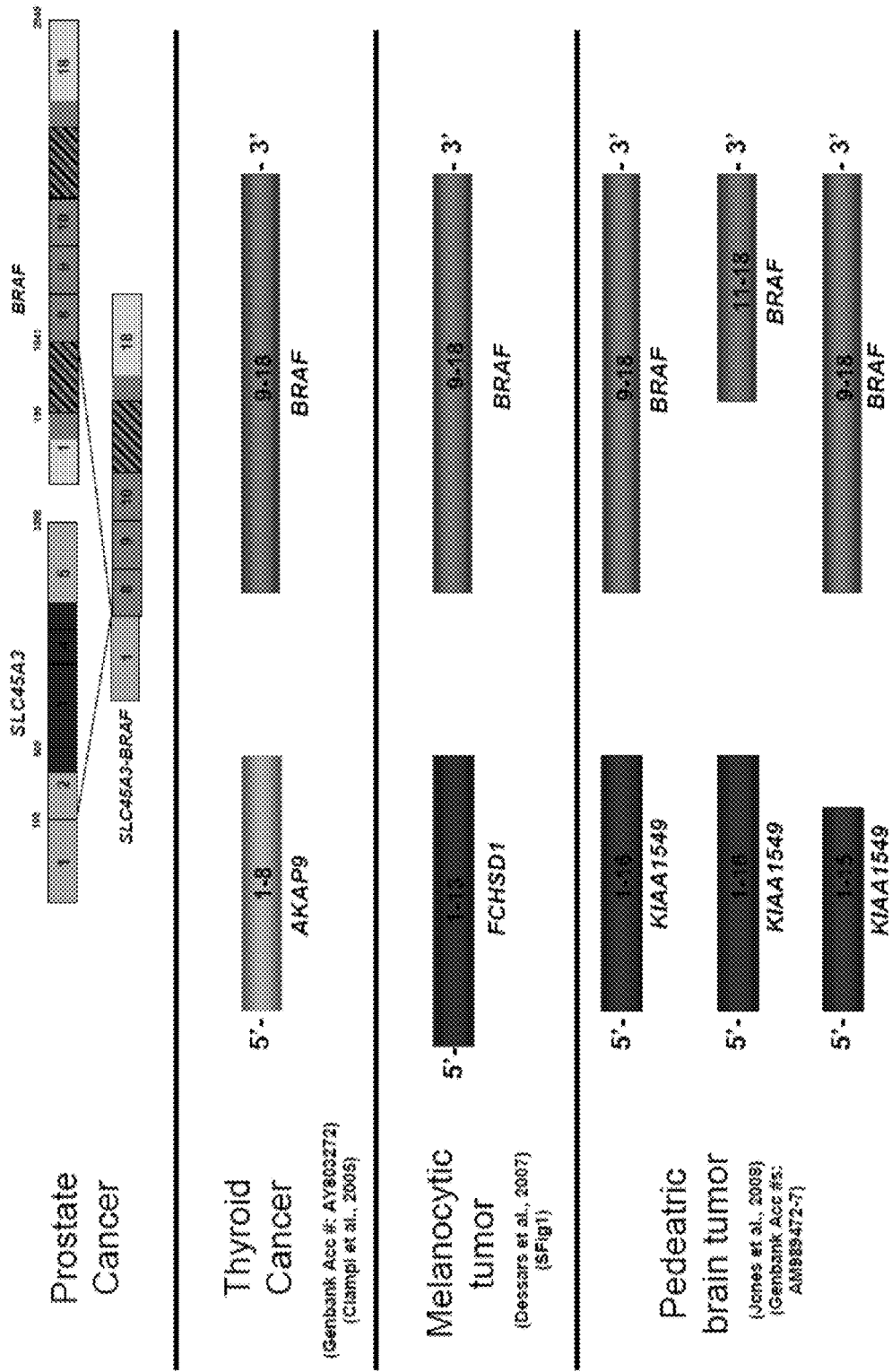
FIG. 12 shows BRAF fusion transcripts by cancer.
Figure 13:
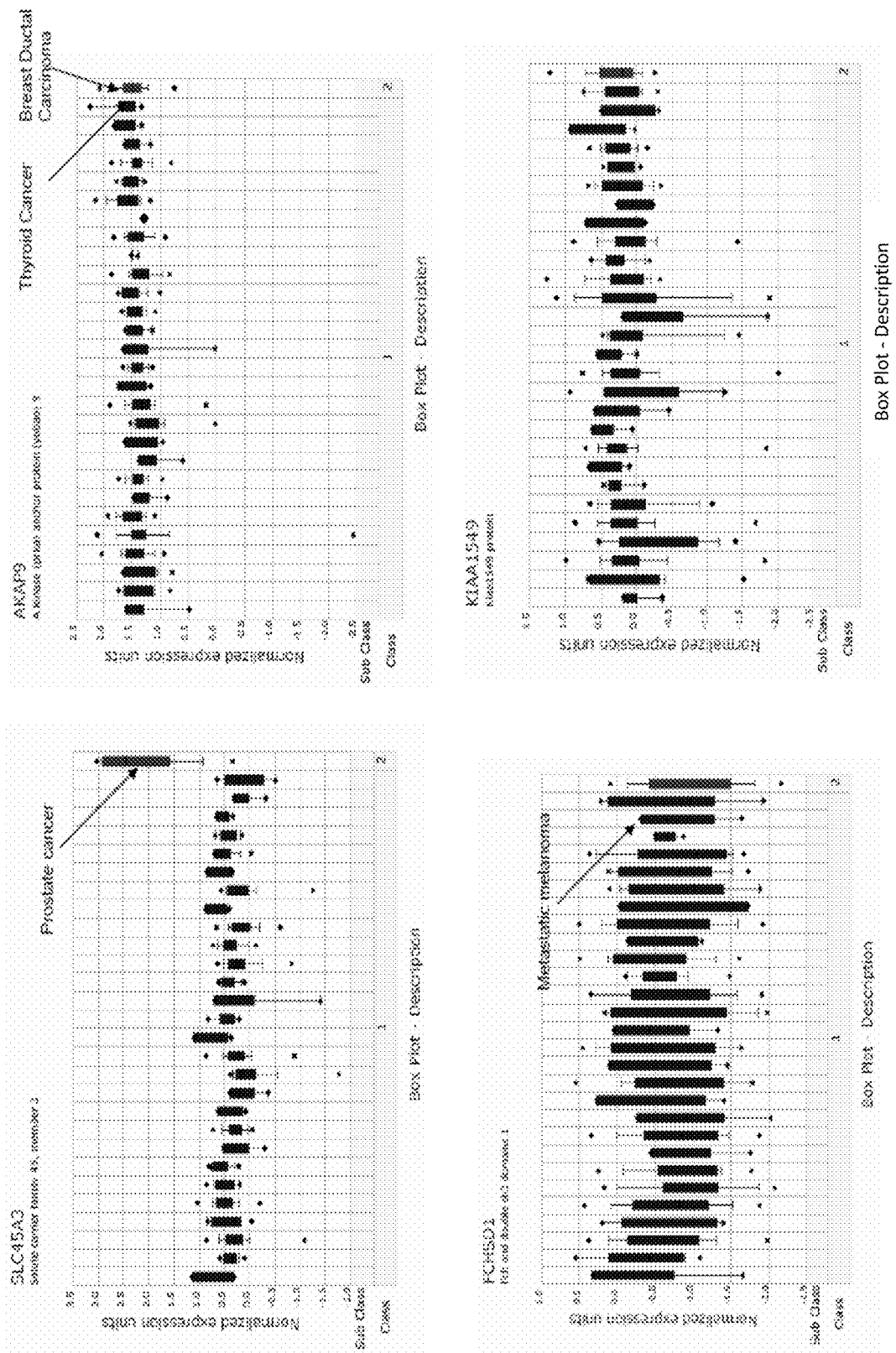
FIG. 13 shows expression plots of SLC45A3, AKAP9, FCHSD1, and KIAA1549.
Figure 14:
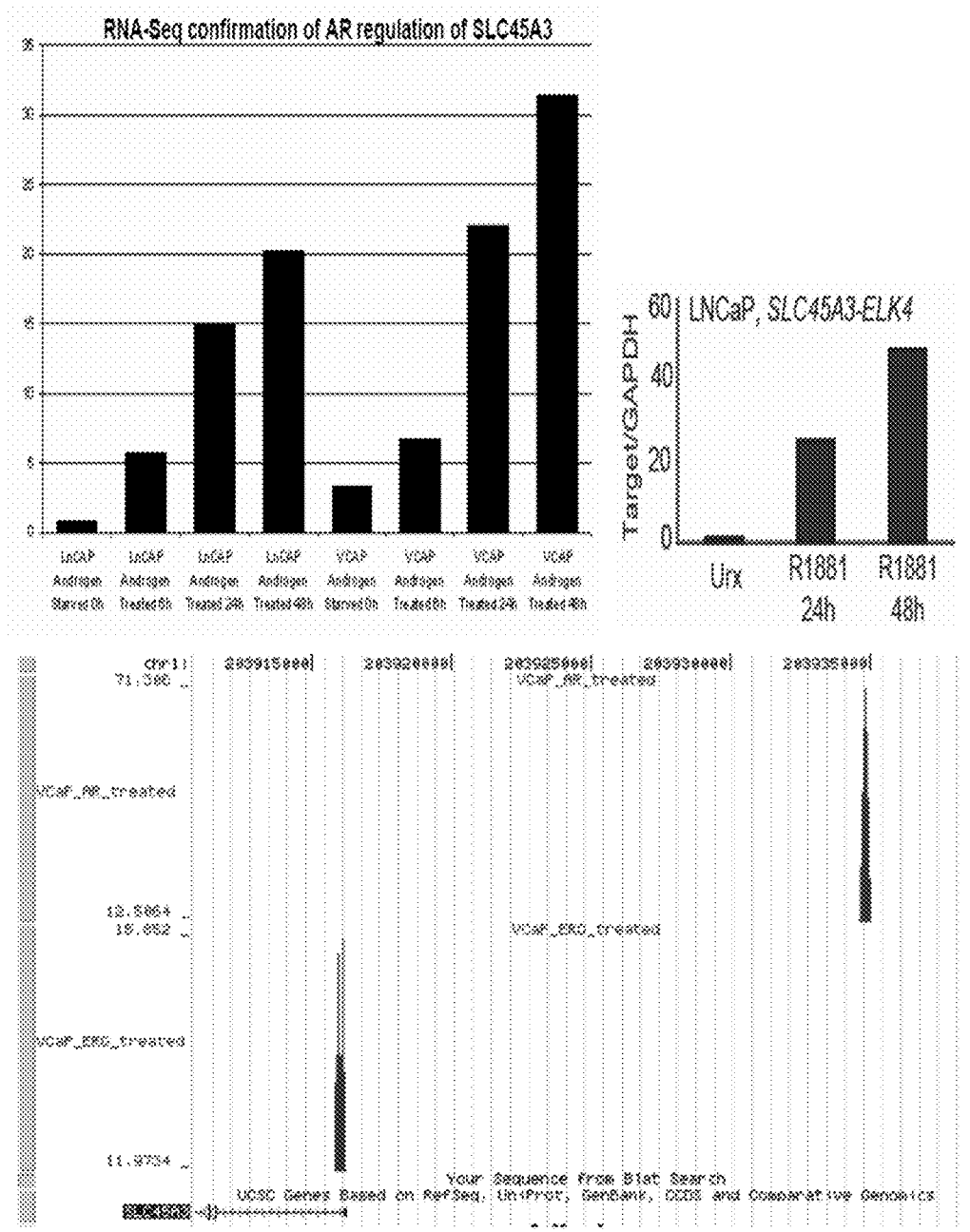
FIG. 14 shows androgen regulation of SLC45A3.

The SLC45A3-BRAF fusion transcript is predicted to transcribe exon 8 (highlighted in FIG. 10) onwards, and therefore also contains the kinase domain of BRAF FIG. 11 shows paired end transcriptome discovery of the inter-chromosomal gene fusion transcript SLC45A1-BRAF. FIG. 12 shows BRAF fusion transcripts by cancer. FIG. 13 shows a box plot of expression levels of several genes. FIG. 14 shows androgen regulation of SLC45A3. The top left panel shows RNA-Seq gene expression demonstrating that SLC45A3 is responsive to androgen treatment. The top right panel shows qRT-PCR confirmation of AR regulation of SLC45A3. The bottom right panel shows UCSC screenshot highlighting ChIP-Seq peaks representing ERG and AR regulation of SLC45A3.

FIG. 1 shows the discovery of SLC45A3-BRAF and ESRP1-RAF1 and RAF1-ESRP1 gene fusions in ETS negative prostate cancer. FIG. 1(a) shows a histogram of gene fusion nomination scores in clinically localized prostate tumor samples PCA1, PCA2, PCA3 and PCA17 harboring FLJ35294-ETV1 (top), TMPRSS2-ERG (middle), SLC45A3-BRAF (bottom left) and ESRP1-RAF1 and RAFT-ESRP1 (bottom right), respectively. FIG. 1(b) shows a schematic representation of paired-end reads supporting the inter-chromosomal gene fusion between SLC45A3 and BRAF. Protein kinase-like domain in BRAF gene remains intact following fusion event. (c &d) Schematic representation of paired-end reads supporting inter chromosomal gene fusions between ESRP1 and RAF1 resulting in reciprocal fusion genes ESRP1-RAF1 and RAF1-ESRP1.

FIG. 2 shows validation of expression of SLC45A3-BRAF, ESRP1-RAF1 and RAF1-ESRP1 gene fusions. FIG. 2(a) qRT-PCR validation of SLC45A3-BRAF gene fusion in PCA3 and (b) exon specific PCR using exons spanning primers showing the high level expression of BRAF exons 8-18 relative to the exons 1-7. FIG. 2(c) shows qRT-PCR validation of ESRP1-RAF1 and RAF1-ESRP1 reciprocal gene fusions in PCA17. FIG. 2(d) shows FISH validation of SLC45A3-BRAF (left) and ESRP1-RAF1 (right) gene fusion in PCA3 and PCA17 respectively. The individual signals indicate the normal chromosomes 1 and 7 (SLC45A3 and BRAF) in PCA3 and chromosomes 8 and 3 (ESRP1 and RAF1) in PCA17. The co localizing signals (arrow) indicate the fusion event detected using BAC clones from the 5' and 3' end of the 5' and 3' partner genes, respectively. Tumor PCA3 show two copies of the rearranged chromosome. FIG. 2(e) shows Western blot analysis showing the expression of 120 kDa ESRP1-RAF1 fusion protein in PCA17 and in HEK293 cells transfected with ESRP1-RAF1 full length fusion construct cloned from PCA17.

Figure 3:
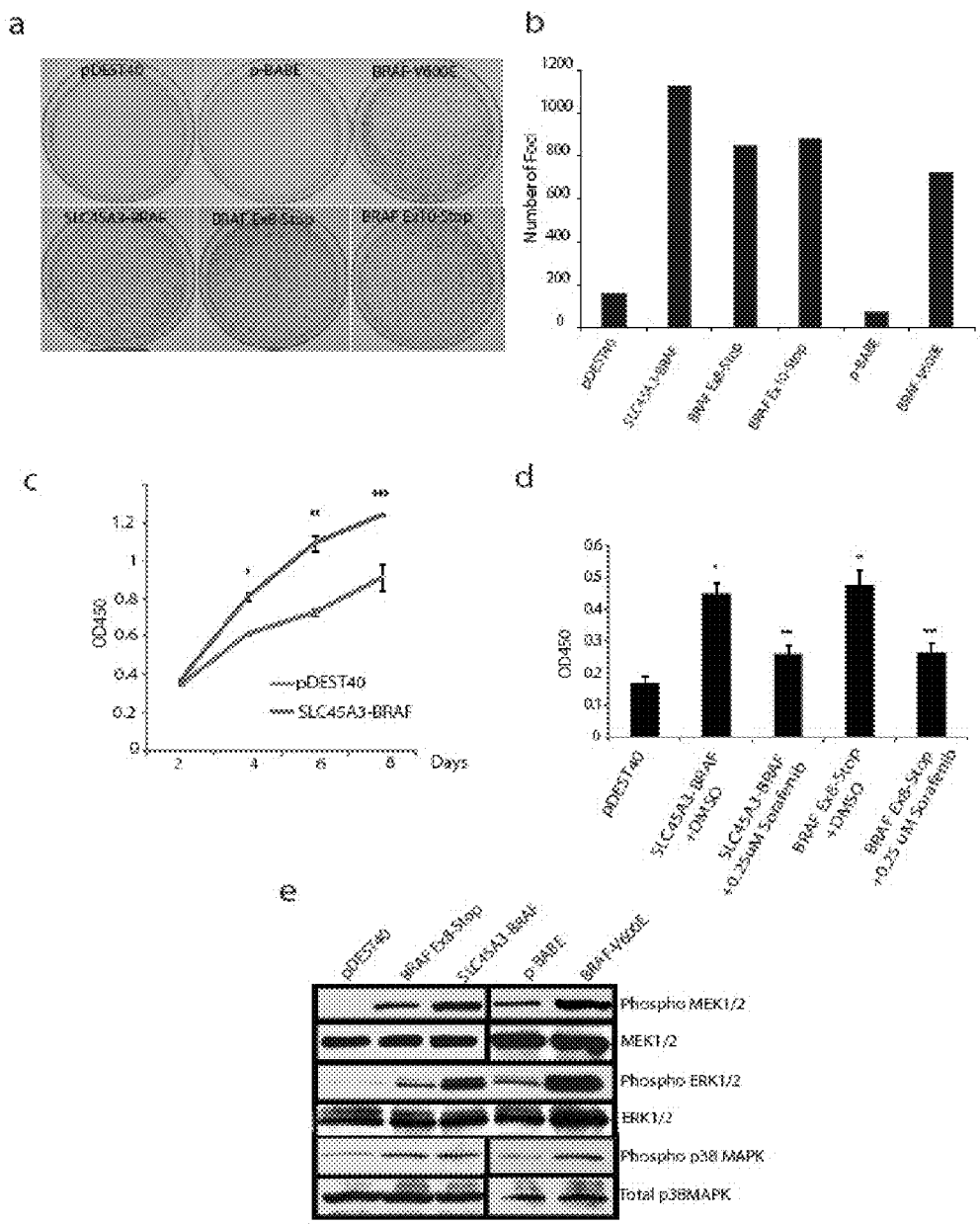
FIG. 3 shows transformation of NIH3T3 cells by SLC45A3-BRAF fusion transcript. a) Foci induction by fusion constructs SLC45A3-BRAF, BRAF EX8-stop, BRAF EX10-stop, RAF mutant V600E and vector controls (pDEST40 for fusion transcripts and pBABE for mutant V600E) in NIH3T3 cells. Representative plate shown for each sample and quantification of foci formation is shown in the bar graph (b) from two independent experiments. (c) SLC45A3-BRAF fusion promotes cell proliferation and invasion. (d) RWPE stable cells were treated with 0.25 uM Sorafenib or DMSO control, and WST-1 assay was performed at indicated time. (e) shows an immunoblot. NIH3T3 cells transfected with the indicated constructs were assessed for expression of Phospho-MEK1/2, MEK1/2, Phospho-ERK1/2, ERK1/2, Phospho-p38MAPK, 30 and Total p38MAPK.

FIG. 3 shows transformation of NIH3T3 cells by SLC45A3-BRAF fusion transcript. FIG. 3a) shows foci induction by fusion constructs SLC45A3-BRAF, BRAF EX8-stop, BRAF EX10-stop, BRAF mutant V600E and vector controls (pDEST40 for fusion transcripts and pBABE for mutant V600E) in NIH3T3 cells. NIH3T3 cells transfected with the indicated constructs were assessed for focus forming ability. Representative plate shown for each sample and quantification of foci formation is shown in the bar graph (b) from two independent experiments. FIG. 3c shows that SLC45A3-BRAF fusion promotes cell proliferation and invasion. WST-1 assay was performed at indicated time points and absorbance was measured at 450 nm. Error bars representing s.e.m. P-values were calculated by t-test compared with pDEST40 control stable cells. FIG. 3(d) shows RWPE stable cells treated with 0.25 μM Sorafenib or DMSO control, and WST-1 assay was performed at indicated time. Error bars represent s.e.m. P-values were calculated by t-test compared with DMSO treated cells. FIG. 3(e) shows an immunoblot. NIH3T3 cells transfected with the indicated constructs were assessed for expression of Phospho-MEK1/2, MEK1/2, Phospho-ERK1/2, Phospho-p38MAPK, and Total p38MAPK.

FIG. 6 shows RNA-seq exon coverage of BRAF in normal sample (NOR9) and index case (PCA3). Exons are shown at the bottom in alternating shades of grey. Bars highlight the nucleotide coverage across the exons.

Figure 7:
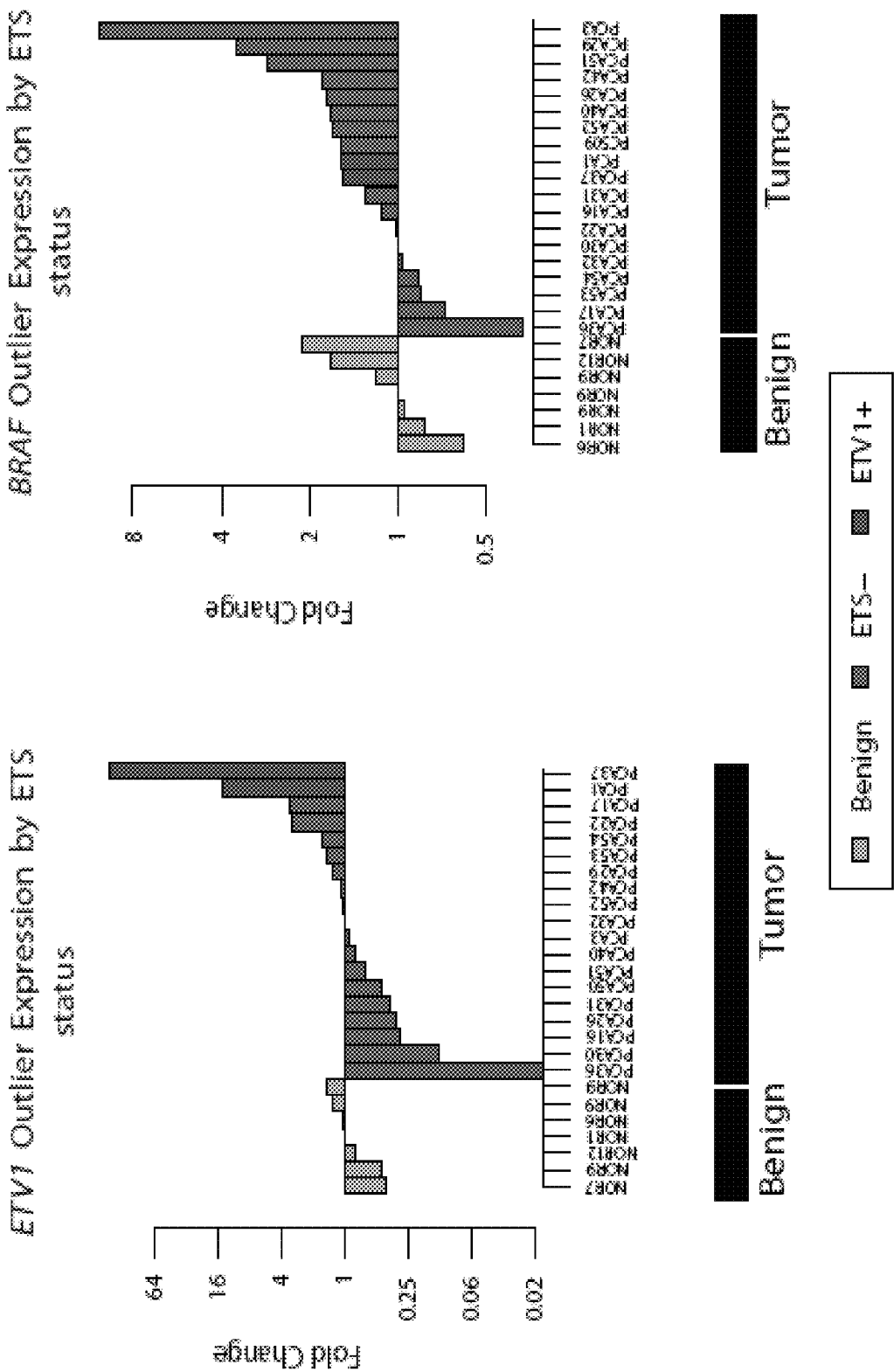
FIG. 7 shows ETV1 and BRAF RNA-Seq outlier expression profiles.
Figure 8:
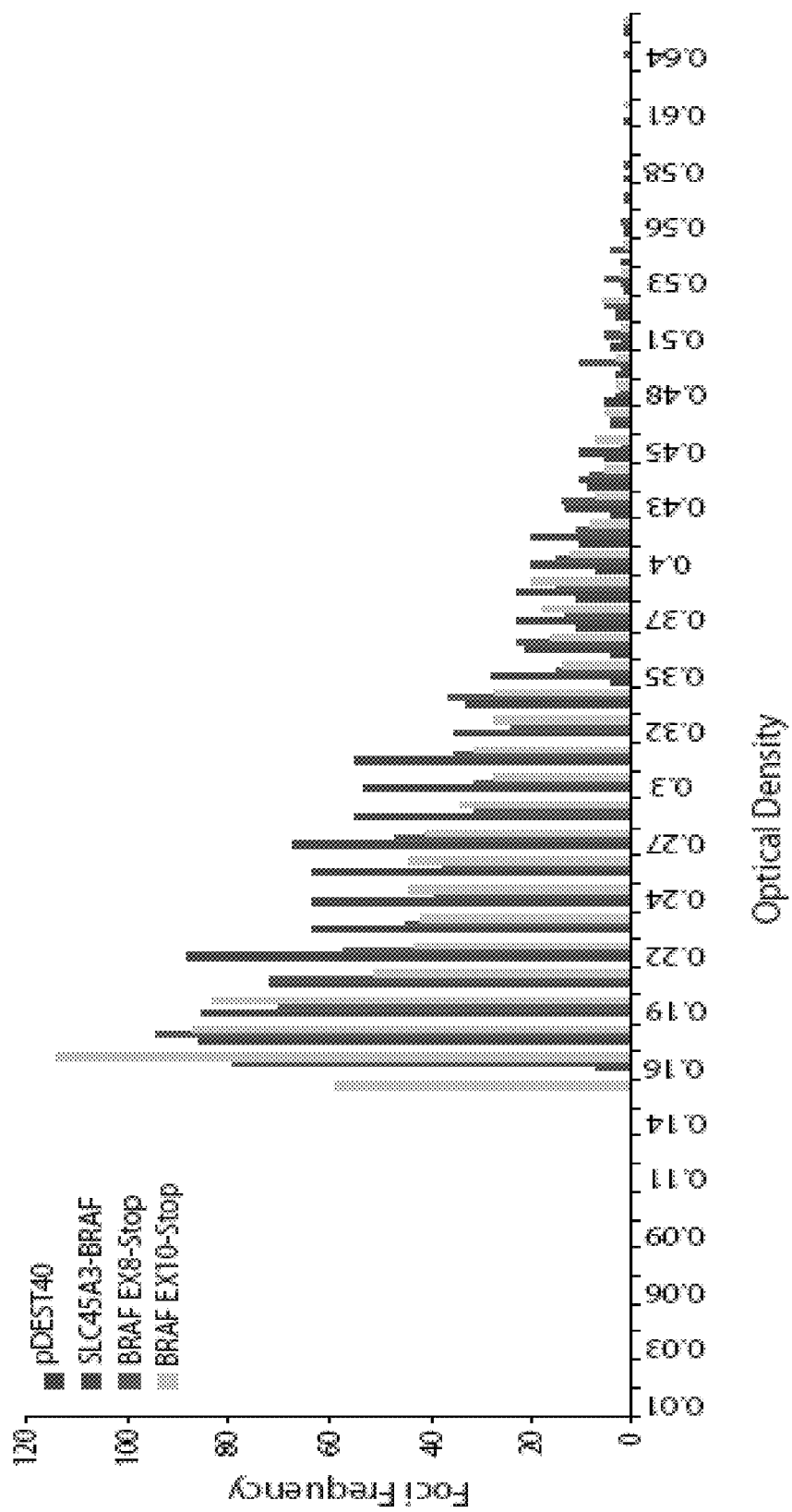
FIG. 8 shows a comparison of the foci frequencies of NIH3T3 cells expressing fusion transcript SLC45A3-Braf, BRAF Ex8-stop and BRAF Ex10-stop and pDEST40 vector.

FIG. 7 shows ETV1 and BRAF RNA-Seq outlier expression profiles. Samples are categorized as benign or tumor prostate samples. Tumor samples are further classified into ETS-samples and ETV1+ samples FIG. 8 shows a comparison of the foci frequencies of NIH3T3 cells expressing fusion transcript SLC45A3-Braf, BRAF Ex8-stop and BRAF Ex10-stop and pDEST40 vector. Foci densities of NIH3T3 cells expressing fusion transcripts SLC45A3-BRAF, BRAF Ex8-stop, BRAF Ex10-stop and vector control (pDEST40) were evaluated using colony counter (Oxford Optronix Ltd., Oxford UK, software v4.1, 2003). Values for minimum colony radius and maximum colony radius were set at 0.10 mm and 2.75 mm respectively, while minimum colony density was fixed at 0.15 optical densities (OD). The bar diagram show frequencies of foci on y-axis falling on the range (0.01 to 0.65 OD) of optical densities on x-axis.

Figure 9:
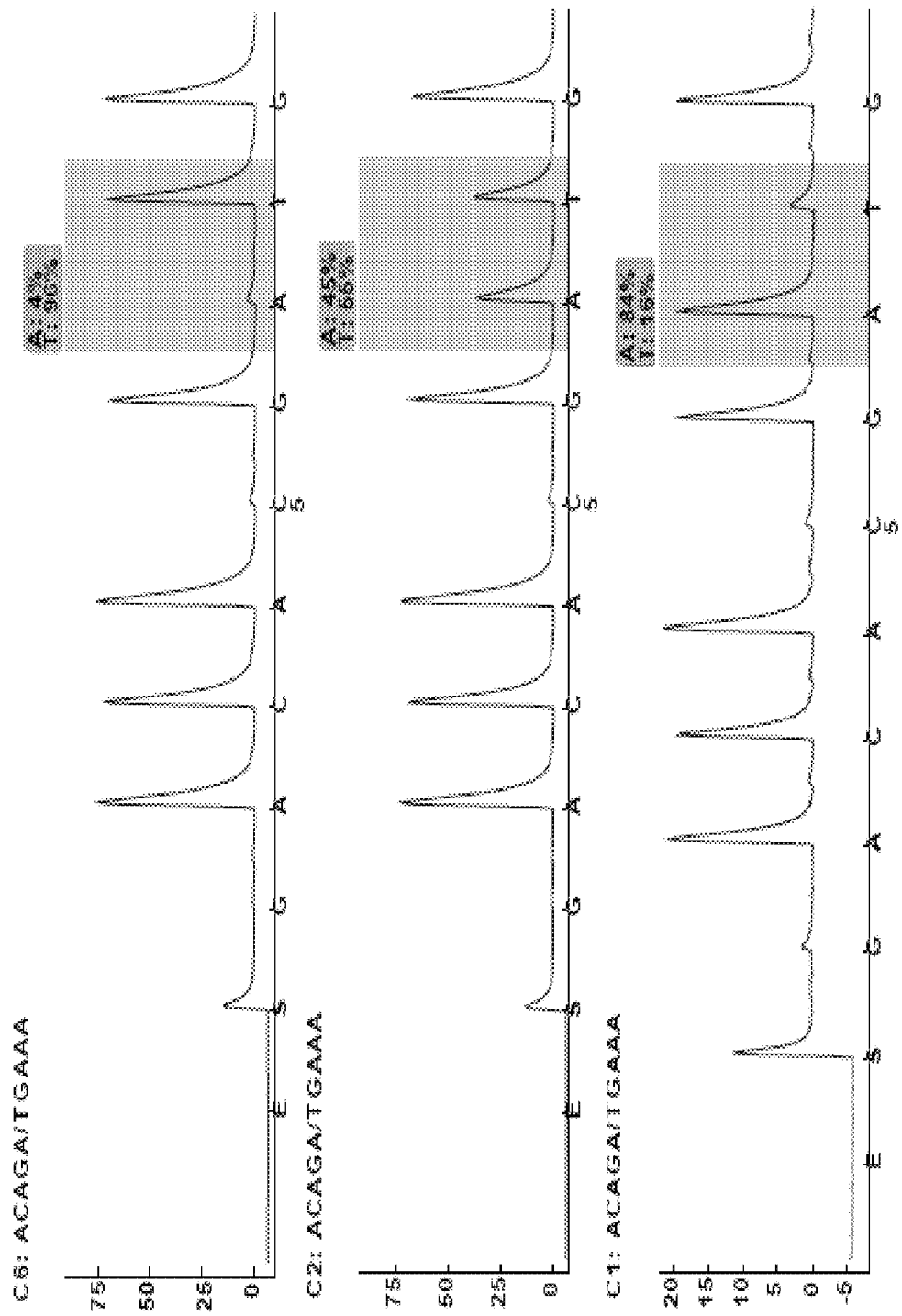
FIG. 9 shows representative pyrograms showing the BRAF V600E mutation status.

FIG. 9 shows representative Pyrograms showing the BRAF V600E mutation status (shaded grey). The nucleotide dispensation order ACAGA/TGAAA (SEQ ID NO:5) assays for the variable position A/T in codon 600 of BRAF gene. The top Pyrogram represents wild type (T/T), middle mutant/wildtype (A/T), and bottom (A/A) genotype.

TABLE 1 shows FISH evaluation for the incidence of BRAF and RAF1 gene rearrangement in prostate cancer.

| Sample ID | Age | Diagnosis | Gleason Score | ERG Rearrangement | BRAF Rearrangement | BRAF 5' Partner | RAF1 Rearrangement | RAF1 5' partner |
|---|---|---|---|---|---|---|---|---|
| PCA3 | 59 | PCA | 4 + 4 | Negative | Positive | SLC45A3 | Negative | |
| 2073 | 75 | PCA | 4 + 4 | Negative | Positive | * | Negative | |
| 2083 | NA | PCA | 4 + 4 | Negative | Positive | * | Negative | |
| 2090 | 89 | PCA | 5 + 4 | Negative | Positive | * | Negative | |
| WA-37 | 63 | METS | 4 + 5 | 5' deletion | Positive | * | Negative | |
| PCA569 | 62 | PCA | 4 + 3 | Negative | 5' deletion | * | Negative | |
| PCA17 | NA | PCA | 3 + 4 | Negative | Negative | * | Positive | ESRP1 |
| 3772 | 66 | PCA | 3 + 3 | Negative | Negative | * | 3' deletion | NA |
| WA50 | 62 | METS | NA | Negative | Negative | * | 3' deletion | NA |

*: not evaluated due to non availability of frozen tissue

Figure 4:
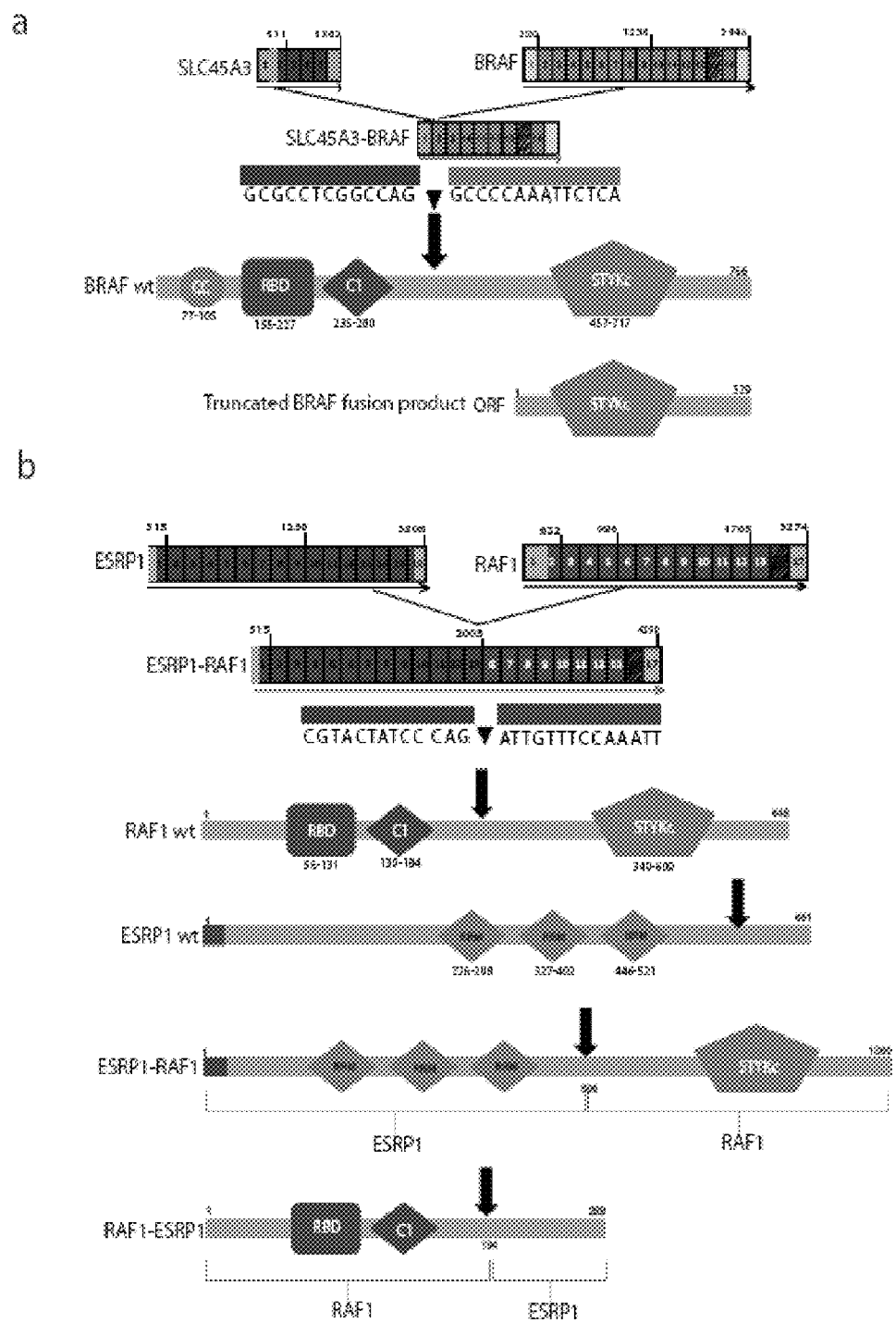
FIG. 4 shows the exon structure of BRAF (A) and RAF1 (B) normal and fusion transcripts.

FIG. 4 shows the exon structure of BRAF (A) and RAF1 (B) normal and fusion transcripts. The kinase domain is retained in both BRAF and RAF1 fusion genes. The SLC45A3-BRAF fusion results in the expression of a truncated BRAF gene retaining the entire kinase domain. The ESRP1-RAF1 fusion, a 4.2 kb fusion transcript with an open reading frame of 1060 aa was expressed resulting in the formation of a 120 kDa fusion.

FIG. 5 shows genomic organization and FISH validation of BRAF and RAF1 gene rearrangement. Schematic diagrams in the top panel of (a) and (b) show the genomic location of SLC45A3 and BRAF and ESRP1 and RAF1 genes respectively. The rectangles with BAC clone identification numbers indicate the 5' and 3' BAC clones used for the FISH analysis. The bottom panel in (a) and (b) shows the FISH analysis in normal and tumor cells. BRAF split probe show two copies of rearranged chromosomes (arrows) and SLC45A3 5'-BRAF 3' fusion probes show two copies of fusion signal. RAF1 split probes show two colocalizing signal in the normal cells and rearranged signal pattern in tumor cells. ESRP1 split probes show rearrangement in the tumor cells. 5' ESRP1 probe and 3' RAF1 probe shows separate signal in normal cells and one fusion signal in tumor cells.

TABLE 2 shows BRAF mutation V600E genotypes determined by Pyrosequencing

| | Genotype* | Pyrosequencing |
|---|---|---|
| Melanoma | | |
| SK-MEL-2 | wt | Wt |
| SK-MEL-5 | wt/mutant | wt/mutant |
| SK-MEL-19 | mutant | Mutant |
| SK-MEL-28 | mutant | Mutant |
| SK-MEL-29 | mutant | Mutant |
| SK-MEL-103 | wt | Wt |
| G-361 | wt/mutant | wt/mutant |
| Malme-3M | wt/mutant | wt/mutant |
| mel-1 | wt/mutant | wt/mutant |
| Prostate | | |
| Localized Prostate cancer (n = 42) | ? | Wt |
| Metastatic prostate cancer (n = 21) | ? | Wt |
| Benign Prostate (n = 5) | ? | Wt |

TABLE 3 shows primer sequences used for cloning and validation.

| Primer ID | Primer Sequence: (5'-3') | SEQ ID NO |
|---|---|---|
| q-RT PCR Primers for SLC45A3-BRAF gene fusion | | |
| SLC45A3 5' F | AGCCGCGCGCCTCGGCCA | 6 |
| BRAF 3' R | ATCAGGAATCTCCCAATCATCACT | 7 |
| Primers for cloning SLC45A3-BRAF full length fusion transcript | | |
| SLC45A3 5' F | GTACCAGCCCCACCCCTCTATCC | 8 |
| SLC45A3 3' R | TCAGTGGACAGGAAACGCACCATA | 9 |
| BRAF EX8-Stop F | GCGCCAAATTCTCACCAGTCCGTC | 10 |
| BRAF EX8-Stop R | TCAGTGGACAGGAAACGCACCA | 11 |
| BRAF EX10-Stop F | ATGAAACACTTGGTAGACGGGA | 12 |
| BRAF EX10-Stop R | TCAGTGGACAGGAAACGCACCA | 13 |
| BRAF Exon spanning Primers | | |
| BRAF EX2 F | AACATATAGAGGCCCTATTGGACA | 14 |
| BRAF EX3 R | AGAAGATGTAACGGTATCCATTG | 15 |
| BRAF EX4 F | GGAGTTACAGTCCGAGACAGTCTAA | 16 |
| BRAF EX5 R | CAGTAAGCCAGGAAATATCAGTGTC | 17 |
| BRAF EX6 F | AGCGTTGTAGTACAGAAGTTCCACT | 18 |
| BRAF EX7 R | AGATGTTAGGGCAGTCTCTGCTA | 19 |
| BRAF EX8 F | TGTGCATATAAACACAATAGAACCTG | 20 |
| BRAF EX10 R | TTCGATTCCTGTCTTCTGAGG | 21 |
| BRAF EX11 F | AAAACACTTGGTAGACGGGACTC | 22 |
| BRAF EX12 R | CTTGTAACTGCTGAGGTGTAGGTG | 23 |
| BRAF EX13 F | TTGTATCACCATCTCCATATCATTG | 24 |
| BRAF EX14 R | GGATGATTGACTTGGCGTGTA | 25 |
| BRAF EX15 F | CTACAGTGAAATCTCGATGGAGTG | 26 |
| BRAF EX16 R | TCATACAGAACTTCCAAATGC | 27 |
| BRAF EX17 F | CGAGGATACCTGTCTCGAGAT | 28 |
| BRAF EX18 R | GATGCACTGCGGTGAATTTTT | 29 |
| BRAF 3'UTR F | AGTGAGAGAGTTCAGGAGAGTAGCA | 30 |
| BRAF 3'UTR R | AAGTATAAATTTTAGTTTGGGAAAAA | 31 |
| qRT PCR Primers for RAF1-ESRP1 gene fusion | | |
| RAF1 EX5 F | CATGAGCACTGTAGCACCAAA | 32 |
| ESRP1 EX14 R | AGCAGCTGTAGGGATAGCC | 33 |
| qRT PCR Primers for ESRP1-RAF1 gene fusion | | |
| ESRP1 EX13 F | GTACTACCCAGCAGGCACTCA | 34 |
| RAF1 EX6 R | CTGGGACTCCACTATCACCAA | 35 |
| Primers for cloning RAF1-ESRP1 full length fusion transcript | | |
| RAF1 5' F | ATGGAGCACATACAGGGAGCT | 36 |
| ESRP1 3' R | TTAAATACAAACCCATTCTTTGG | 37 |

TABLE 3-continued shows primer sequences used for cloning and validation.

| Primer ID | Primer Sequence: (5'-3') | SEQ ID NO |
|---|---|---|
| Primers for cloning ESRP1-RAF1 full length fusion transcript | | |
| ESRP1 5' F | ATGACGGCCTCTCCGGATTA | 38 |
| RAF1 3' R | CTAGAAGACAGGCAGCCTCG | 39 |

Example 2: RAS Gene Fusions

A. Materials and Methods

Analysis of Array CGH/SNP Datasets for Acute Lymphoblastic Leukemia and Prostate Cancer For Affymetrix SNP arrays, model-based expression was performed to summarize signal intensities for each probe set, using the perfect-match/mismatch (PM/MM) model. For copy number inference, raw copy numbers were calculated for each tumor sample by comparing the summarized signal intensity of each SNP probe set against a diploid reference set of samples. In Agilent two channel array CGH dataset, the differential ratio between the processed testing channel signal and processed reference channel signal was calculated. All resulting relative DNA copy number data were log 2 transformed, which reflects the DNA copy number difference between the testing and reference samples. To improve the accuracy of copy number estimation, a reference set normalization method was employed. For each sample, non-sex chromosomes were split into 30 Mb region units. The absolute mean of the relative DNA copy number data for the probes from each region was calculated and compared with the other regions. The probes from two regions with minimal absolute mean in each sample were picked up as an internal reference set, representing the chromosomal regions with minimal DNA copy number aberrations. For each sample, log ratios were transformed into a normal distribution with a mean of 0, under the null model assumption for the reference probe set. The normalization method was implemented by perl programming.

Amplification Breakpoints Rating and Assembling (ABRA)

Figure 20:
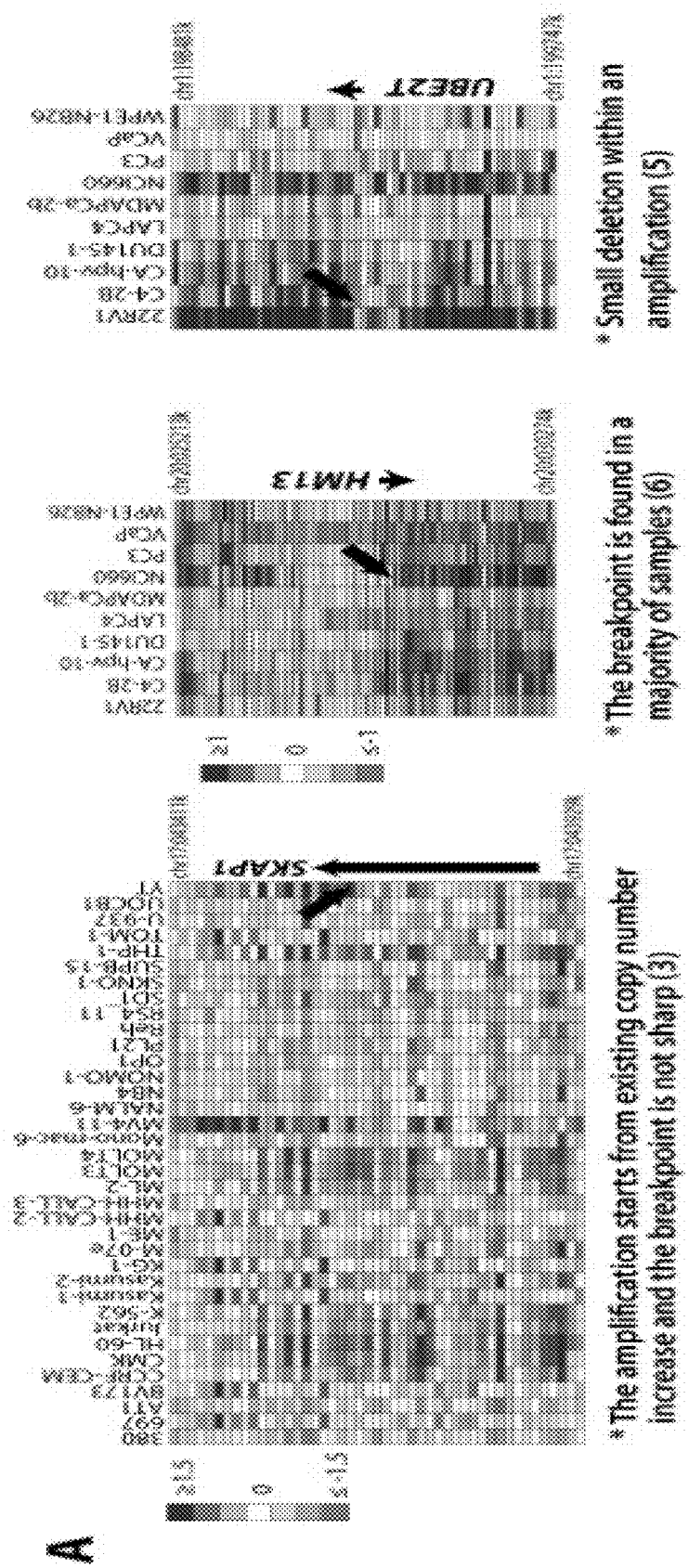
FIG. 20 shows SNP array and array CGH data for representative 5' and 3' fusion partner candidates (genes with 5' or 3' amplification) depicting the criteria of manual curation. (A) The relative DNA copy number data for representative candidate 3' partners in leukemia and prostate cancer cell lines with unacceptable breakpoints. (B) The array CGH data for candidate 5' fusion partners of ABL1 identified by amplification breakpoint assembling analysis on K-562, together with other leukemia cell lines. (C) The array CGH data for candidate 5' fusion partners of KRAS on DU145 (two replicate hybridizations) and other prostate cancer cell lines.
Figure 20:
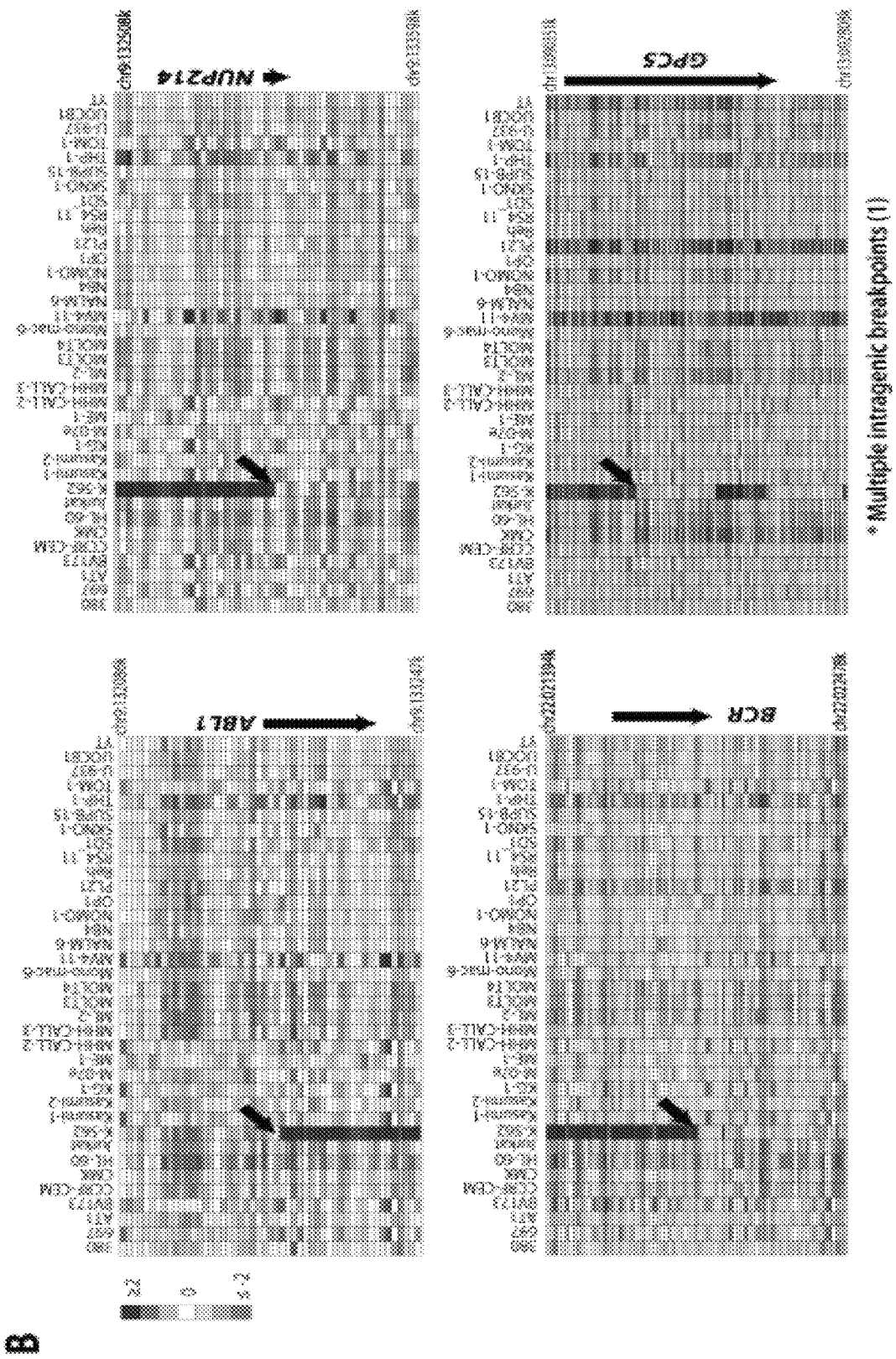

ABRA analysis has three steps. First, the copy number data from the array CGH or array SNP datasets were segmented by the circular binary segmentation (CBS) algorithm (Karnoub et al., Nat Rev Mol Cell Biol 9, 517 (July, 2008)). The level of amplification was determined by comparing the relative copy number data of the amplifications with the neighboring segments, and the breakpoints having equal to or more than 2 copies number gain were selected (≥0.75). Amplifications spanning more than 500 kb are included in the analysis. The genomic position of each amplification breakpoint was mapped with the genomic regions of all human genes. The genomic region of each human gene was designated as the starting of the transcript variant most approaching the 5' of the gene, and the end of the variant most approaching the 3' of the gene. The partially amplified genes were classified into candidate 5' and 3' partners based on the association of amplification breakpoints with gene placements. 5' amplified genes are considered as 5' partners, 3' amplified genes as 3' partners. Second, the partially amplified "cancer genes" were identified as driver fusion gene candidates. This was achieved by mapping 3' amplified genes to known cancer genes defined by cancer gene census. To evaluate the relevance of partially amplified genes underlying cancer, the "concept signature technology" (ConSig) method (Moul et al., Prostate 20, 327 (1992)), which can preferentially identify biologically meaningful genes based on their association with the "molecular concepts" frequently found in known cancer genes was used. This score is especially discriminative for 3' fusion genes (Moul et al., supra). The 3' amplified genes with acceptable breakpoints (see below criteria, FIG. 20A) were rated by their radial concept signature scores (in brief ConSig Score). The top scored 3' amplified cancer genes were considered as driver fusion gene candidates. Third, the level of amplification for the selected 3' amplified gene was matched with 5' amplified genes from the same cell line to nominate putative 5' partners. The actual location and the quality of the breakpoint were manually curated with the un-segmented relative quantification of DNA copy number data. The situations when the amplification breakpoint is not acceptable are (FIG. 20):

(1) Multiple intragenic breakpoints;
(2) The candidate is not the gene closest to the amplification breakpoint;
(3) The amplification starts from existing copy number increase and the breakpoint is not sharp;
(4) The breakpoint locates at the centromere or the end of the chromosome;
(5) The breakpoint is the result of a small deletion within an amplification; and
(6) The breakpoint is found in a majority of samples.

It is possible that the segmentation process could have slightly different estimation of the breakpoints from the actual location. This is relevant to breakpoint assembling. To overcome this problem, the DNA breakpoints within 10 kb up and 1 kb downstream region of a gene were assigned to this gene during breakpoint ranking; and 20 kb up- and downstream during breakpoint assembling. In practice, this window can be adjusted to improve the performance of ABRA analysis.

In total, six 5' amplified genes were found on K-562, 4 matched the 3' amplification level of ABL1. After curation, only 2 genes BCR and NUP214 had acceptable breakpoints. On DU145, eight and six 5' amplified genes were found from the two replicate hybridizations respectively (Table 4). After curation, UBE2L3-KRAS, SOX5-KRAS, and C14orf166-KRAS were selected for experimental validation. Primers were then designed from the first exon of candidate 5' partners and last exon of candidate 3' partners, as well as the exons next to the breakpoints, to test the putative fusions.

Cell Lines and Tissues

The benign immortalized prostate cell line RWPE, prostate cancer cell line DU145, PC3, Ca-HPV-10, WPE1-NB26 and NCI-H660, Fibroblast cell line NIH 3T3, and human embryonic kidney cell line HEK were obtained from the American Type Culture Collection (Manassas, Va.). Primary benign prostatic epithelial cells (PrEC) were obtained from Cambrex Bio Science (Walkersville, Md.). VCaP was derived from a vertebral metastasis from a patient with hormone-refractory metastatic prostate cancer (Seeburg et al., *Nature* 312, 71 (Nov. 1-7, 1984)). Tissues were from the radical prostatectomy series at the University of Michigan and from the Rapid Autopsy Program, which are both part of University of Michigan Prostate Cancer Specialized Program of Research Excellence (S.P.O.R.E.) Tissue Core. Tissues were also obtained from a radical prostatectomy series at the University Hospital Ulm (Ulm, Germany). All samples were collected with informed consent of the patients and prior institutional review board approval at each institution. A pool of benign prostate tissue total RNA was obtained from Clontech laboratories (Mountain View, Calif.). Total RNA from all samples was isolated with Trizol (Invitrogen, Carlsbad, Calif.) according to the manufacturer's protocols. RNA integrity was verified by Agilent Bioanalyzer 2100 (Agilent Technologies, Palo Alto, Calif.).

Microarray Comparative Genomic Hybridization (Array CGH)

To nominate potential driver gene fusions in prostate cancer cell lines, ten prostate cancer cell lines were profiled on an Agilent-014698 Human Genome CGH Microarray 105A (Agilent Technologies, Palo Alto, Calif.), including 22RV1, C4-2B, CA-hpv-10, DU145, LAPC4, MDAPCa-2b, NCI660, PC3, VCaP, and WPE1-NB26. All cell lines were grown in full serum in accordance with the distributor's instructions. The genomic DNA extracted from those cell lines were hybridized against reference human male genomic DNA (6 normal individuals, Promega, #G1471) to oligonucleotide printed in the array format according to manufacture's protocol. Analysis of fluorescent intensity for each probe detected the copy number changes in cancer cell lines relative to normal reference genome (Genome build 2004). Replicate array CGH hybridizations of DU145 were done to nominate 5' partners of KRAS.

Paired-End Transcriptome Sequencing and Analysis

DU145 mRNA samples were prepared for sequencing using the mRNA-seq sample prep kit (Illumina) following manufacturers protocols. The raw sequencing image data were analyzed by the Illumina analysis pipeline, aligned to the unmasked human reference genome (NCBI v36, hg 18) using the ELAND software (Illumina). The paired reads were then analyzed as previously described to nominate mate-pair chimeras (Schubbert, K. Shannon, G. Bollag, *Nat Rev Cancer* 7, 295 (April, 2007)).

Reverse-Transcription PCR(RT-PCR) and Sequencing

Complimentary DNA was synthesized from one microgram of total RNA, using SuperScript III (Invitrogen, Carlsbad, Calif.) in presence of random primers. The reaction was carried out for 60 minutes at 50° C. and the cDNA was purified using microcon YM-30 (Millipore Corp, Bedford, Mass., USA) according to manufacturer's instruction and used as template in PCRs. All oligonucleotide primers used in this study were synthesized by Integrated DNA Technologies (Coralville, Iowa) and are listed in Table 10. Polymerase chain reaction was performed with Platinum Taq High Fidelity and fusion-specific primers for 35 cycles. Products were resolved by electrophoresis on 1.5% agarose gels, and bands were excised, purified and TOPO TA cloned into pCR 4-TOPO TA vector (Invitrogen, Carlsbad, Calif.). Purified plasmid DNA from at least 4 colonies was sequenced bi-directionally using M13 Reverse and M13 Forward primers on an ABI Model 3730 automated sequencer at the University of Michigan DNA Sequencing Core.

Quantitative PCR (qPCR)

Quantitative PCR (qPCR) was performed using the StepOne Real Time PCR system (Applied Biosystems, Foster City, Calif.). Briefly, reactions were performed with SYBR Green Master Mix (Applied Biosystems) cDNA template and 25 ng of both the forward and reverse fusion primers using the manufacturer recommended thermocycling conditions. For each experiment, threshold levels were set during the exponential phase of the QPCR reaction using the StepOne software. The amount of each target gene relative to the housekeeping gene glyceraldehyde-3-phosphate dehydrogenase (GAPDH) for each sample was determined using the comparative threshold cycle (Ct) method (Applied Biosystems User Bulletin #2). For the experiments presented in FIG. 16b, the relative amount of the target gene was calibrated to the relative amount from a benign prostate. For a subset of cell lines and tissue samples, qPCR was performed using the Taqman probe CAGCAACCAAAACC (SEQ ID NO:40). Samples with RQ value≥10 by fusion qPCR were considered fusion positive.

RNA Ligase Mediated Rapid Amplification of cDNA Ends (RLM-RACE)

RNA ligase mediated rapid amplification of cDNA ends was performed using the GeneRacer RLM-RACE kit (Invitrogen), according to the manufacturer's instructions. The prostate cell line DU145 and tissue samples PCA1-3 and MET10 that had high UBE2L3-KRAS expression levels by qPCR were selected for 5' RACE. Briefly, two micrograms of total RNA was treated with calf intestinal phosphatase to remove 5' phosphates from truncated mRNA and non-mRNA and decapped with tobacco acid pyrophosphatase. The GeneRacer RNA Oligo was ligated to full length transcripts and reverse transcribed using SuperScript III. To obtain 5' ends, first-strand cDNA was amplified with Platinum Taq High Fidelity (Invitrogen) using the GeneRacer 5' and KRAS R2 primer pairs. Nested PCR was then performed with GeneRacer 5' nested Primer and KRAS R3 or R4 primers. Products were resolved by electrophoresis on 1.5% agarose gels and bands were excised, purified and sequenced as described above.

Fluorescence In Situ Hybridization (FISH)

To evaluate the fusion of UBE2L3 with KRAS, a two-color, two-signal FISH strategy was employed, with probes spanning the respective gene loci. The digoxin-dUTP labeled BAC clone RP11-317J15 was used for the UBE2L3 locus and the biotin-14-dCTP BAC clone RP11-608F13 was used for the KRAS locus. To detect possible translocations at KRAS locus, a break-apart FISH strategy was used, with two probes spanning the KRAS locus (digoxin-dUTP labeled BAC clone RP11-68123, (5' KRAS) and biotin-14-dCTP labeled BAC clone RP11-157L6 (3' KRAS)). All BAC clones were obtained from the Children's Hospital of Oakland Research Institute (CHORI). Prior to FISH analysis, the integrity and purity of all probes were verified by hybridization to metaphase spreads of normal peripheral lymphocytes.

For interphase FISH on DU145 cells, interphase spreads were prepared using standard cytogenetic techniques. For interphase FISH on a series of prostate cancer tissue microarrays, tissue hybridization, washing and color detection were performed as described (Tomlins et al., *Science* 310, 644 (Oct. 28, 2005); Kumar-Sinha et al., *Nat Rev Cancer* 8, 497 (July, 2008)). The total evaluable cases include 78 PCAs and 29 METs for KRAS split probes, and 67 PCAs and 18 METs for UBE2L3/KRAS fusion probes. For evaluation of the interphase FISH on the TMA, an average of 50-100 cells per case were evaluated for assessment of the KRAS rearrangement and UBE2L3/KRAS fusion. In addition, formalin fixed paraffin-embedded (FFPE) tissue sections from five fusion positive cases were used to confirm the negative FISH results.

Western Blotting

The prostate cancer cell lines DU145 were transfected with siRNA duplex (Dharmacon, Lafayette, Colo., USA) against UBE2L3 (5'-CCACCGAAGATCACATTTA-3'; SEQ ID NO:1), KRAS (5'-GAAGTTATGGAATTCCTTT-3'; SEQ ID NO:2) or the fusion junction (5'-CCGAC-CAAGGCCTGCTGAA-3'; SEQ ID NO:3) by oligo-fectamine (Invitrogen). DU145 transfected with non-targeting siRNA and RWPE cells was used as negative control. Post 48 hours transfection, cells were homogenized in NP40 lysis buffer (50 mM Tris-HCl, 1% NP40, pH 7.4, Sigma, St. Louis, Mo.), and complete proteinase inhibitor mixture (Roche, Indianapolis, Ind.). Ten micrograms of each protein extract were boiled in sample buffer, separated by SDS-PAGE, and transferred onto Polyvinylidene Difluoride membrane (GE Healthcare, Piscataway, N.J.). The membrane was incubated for one hour in blocking buffer [Tris-buffered saline, 0.1% Tween (TBS-T), 5% nonfat dry milk] and incubated overnight at 4° C. with the following antibodies: anti-RAS mouse monoclonal (1:1000 in blocking buffer, Millipore Cat #: 05-516), anti-KRAS rabbit polyclonal (1:1000, Proteintech Group Inc., Cat #: 12063-1-AP) and anti-beta Actin mouse monoclonal (1:5000, Sigma Cat #: A5441) antibodies. Following three washes with TBS-T, the blot was incubated with horseradish peroxidase-conjugated secondary antibody and the signals visualized by enhanced chemiluminescence system as described by the manufacturer (GE Healthcare). To test fusion protein expression in multiple prostate derived cell lines, lysates from DU145, PrEC, RWPE, 22RV1, VCaP, PC3 either untreated or treated with 500 nM bortezomib for 12 hours were used. Bortezomib treated HEK cells over-expressing UBE2L3-KRAS fusion protein was used as a positive control. To explore the activation of MAPK signaling pathways, protein lysates from NIH 3T3 stable cell lines expressing UBE2L3-KRAS, V600E mutant BRAF, G12V mutant KRAS, and vector controls were probed with phospho MEK1/2, phospho p38 MAPK, phospho Akt, and equal loading was demonstrated by probing for the respective total proteins and beta Actin. For ERK activation analysis NIH 3T3 cells were starved for 12 hours before immunoblot analysis using phospho erk1/2 antibody. All antibodies for the MAPK signaling proteins were purchased from Cell Signaling Technologies.

Multiple Reactions Monitoring Mass Spectrometry

Du145 and LnCaP cells were grown to 70% confluence and treated with bortezomib. After 24 hours, cells were harvested and whole cell protein lysates were prepared in RIPA buffer (Pierce Biotechnology, Rockford, Ill., USA) with the addition of protease inhibitor complete mini cocktail (Roche, Indianapolis, Ind., USA). Lysates were cleared by centrifugation and separated by SDS PAGE (Novex, 18% Tris-Glycine, Invitrogen, Carlsbad, Calif., USA). 12 equal sized bands from 15-40 kDa regions were excised for in-gel trypsin digestion. Lyophilized peptides from each gel slice were re-suspended in 3% acetonitrille, 0.1% formic acid containing 25 fmol of each stably isotopically labeled peptide internal standards (Sigma-Aldrich Corp., St. Louis, Mo., USA). Peptides were then separated and measured by CHIP HPLC-multiple reaction monitoring mass spectrometry (MRM-MS). Three transitions for each stably isotopically labeled internal standard and three transitions for endogenous peptides were measured. An overlap of all 6 transitions for each peptide in retention time indicated a positive measurement.

In Vitro Overexpression of the UBE2L3-KRAS Chimera

Expression plasmids for UBE2L3-KRAS were generated with the pDEST40 (with or without 5' FLAG) and pLenti-6 vectors (without 5'FLAG). NIH 3T3 cells were maintained in DMEM with 10% FBS and transfected with either the pDEST40 vector plasmid or pDEST40 containing the UBE2L3-KRAS open reading frame using Fugene 6 transfection reagent (Invitrogen). After three days, transfected cells were selected using 500 µg/ml Geneticin. After three weeks of selection stable cell lines were established for both the vector and UBE2L3-KRAS fusion, and were used for further analyses. Constructs for the G12V mutant KRAS (Addgene plasmid 9052), V600E mutant BRAF (Addgene plasmid 15269), and their respective pBABE-puro vector (Addgene plasmid 1764) were obtained from Addgene (Cambridge, Mass., USA). These plasmid constructs were transfected in NIH 3T3 cells maintained in 10% calf serum and stable lines were generated using puromycin 1 µg/ml for selection. These stable cell lines were used as controls for immunoblot analysis of the RAS-MAPK signaling pathways.

Figure 25:
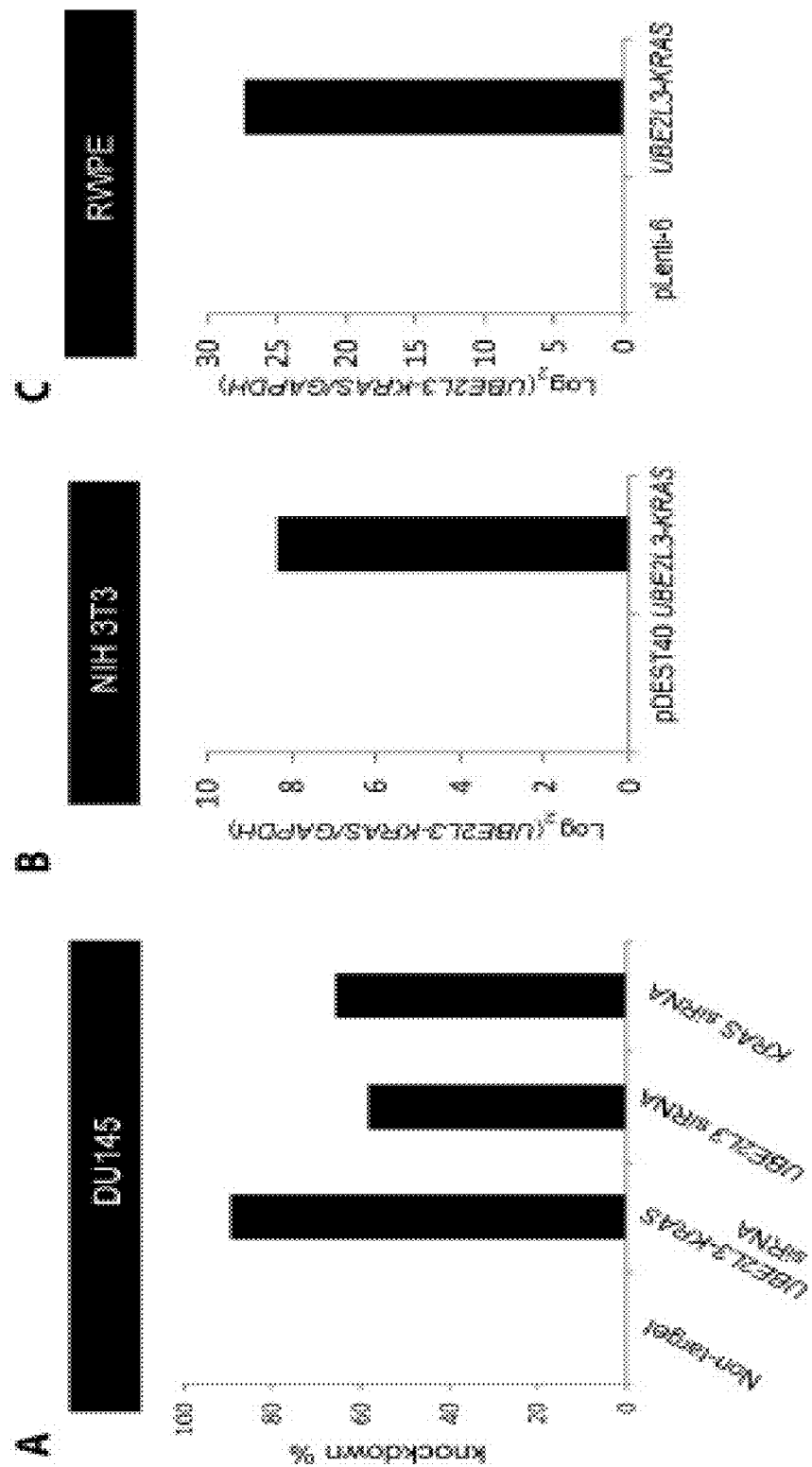
FIG. 25 shows qPCR confirmation of siRNA knockdown and ectopic expression of UBE2L3-KRAS fusion. (A) qPCR confirmation of UBE2L3-KRAS knockdown by siRNA against the fusion junction, wild-type UBE2L3, and wild-type KRAS on DU145. (B-C), qPCR confirmation of NIH 3T3 and RWPE cells expressing UBE2L3-KRAS fusion. NIH 3T3 cells (B) were transfected with the empty pDEST40 vector or the UBE2L3-KRAS fusion. RWPE cells (C) were transfected with lentiviral particles harboring the empty pLenti-6 vector or UBE2L3-KRAS fusion.

To overexpress UBE2L3-KRAS fusion in the prostate derived normal cell lines, RWPE cells were transfected with lentiviral particles expressing the UBE2L3-KRAS open reading frame or the pLenti-6 vector. Three days after infection, the cells were subject to 3 µg/ml blasticidin selection. After three weeks of selection individual clones were picked up and propagated for further analysis. Both the NIH 3T3 and the RWPE overexpression models were tested for UBE2L3-KRAS fusion by qPCR (FIG. 25 B,C) and Western blotting.

Cell Proliferation Assay

For cell proliferation analysis, 10,000 cells of NIH 3T3 expressing UBE2L3-KRAS fusion or the vector were plated on 24 well plates in duplicate wells and cell counts were performed using a Coulter Counter (Beckman Coulter, Fullerton, Calif.) at the indicated times. Similar assays were performed using RWPE stable clones expressing UBE2L3-KRAS fusion or vector. Both cell proliferation assays were performed twice and data from representative assays are presented.

Basement Membrane Matrix Invasion Assay 100,000 cells of RWPE clones expressing UBE2L3-KRAS fusion or pLenti-6 vector were seeded onto a matrigel precoated plate (BD Biosciences) and processed as the manufacturer's recommendation. After 48 hours the inserts were stained with crystal violet. Destaining was carried out using 10% acetic acid, and the invasion was quantitated by comparing the absorbance at 560 nm. DU145 was used as a positive control for the invasion assay.

Foci Formation Assay

Transfections were performed using Fugene 6 according to the manufacturer's protocol (Roche Applied Sciences). NIH 3T3 cells ($1.5 \times 10^5$) in 35-mm plastic dishes were transfected with 2 µg of DNA of the plasmid of interest. Plasmids for fusion transcript UBE2L3-KRAS and oncogenic KRAS G12V were used along with control plasmids (pDEST40 and pBABE respectively). Three days after transfection, cells were split into one 140-mm dishes containing DMEM with 5% calf serum (Colorado Serum Company). The cultures were fed every 3-4 days. After 3 weeks, the cells were stained with 0.2% crystal violet in 70% ethanol for the visualization of foci, and were counted on colony counter (Oxford Optronix Ltd., Oxford UK, software v4.1, 2003). Counts were further confirmed manually.

FACS Cell Cycle Analysis

Propidium iodide-stained stable NIH 3T3 cells expressing the UBE2L3-KRAS fusion or vector were analyzed on a LSR II flow cytometer (BD Biosciences, San Jose, Calif.) running FACSDivia, and cell cycle phases were calculated using ModFit LT (Verity Software House, Topsham, Me.).

NIH 3T3 and RWPE-UBE2L3-KRAS Xenograft Model

Four week old male Balb C nu/nu mice were purchased from Charles River, Inc. (Charles River Laboratory, Wilmington, Mass.). Stable NIH 3T3 and RWPE cells over expressing fusion transcript UBE2L3-KRAS or NIH 3T3-Vector ($2 \times 10^6$ cells) were resuspended in 100 µl of saline with 20% Matrigel (BD Biosciences, Becton Drive, N.J.) and were implanted subcutaneously into the left or both left and right flank regions of the mice. Mice were anesthetized using a cocktail of xylazine (80-120 mg/kg IP) and ketamine (10 mg/kg IP) for chemical restraint before implantation. Eight mice were included in each group. Growth in tumor volume was recorded everyday by using digital calipers and tumor volumes were calculated using the formula ($\pi/6$) (L×W2), where L=length of tumor and W=width. All procedures involving mice were approved by the University Committee on Use and Care of Animals (UCUCA) at the University of Michigan and conform to their relevant regulatory standards.

Results

Using an integrative genomics approach called Amplification Breakpoint Ranking and Assembly (ABRA) analysis KRAS was nominated as a gene fusion with the ubiquitin-conjugating enzyme UBE2L3 in DU145 prostate cancer cells. expression of the UBE2L3-KRAS chimeric transcript was validated in DU145 cells and in 42 out of 112 prostate cancer tissues (38%). The UBE2L3-KRAS fusion protein is relatively unstable and requires proteosomal inhibition to be observed easily. Overexpression of the UBE2L3-KRAS fusion induces an oncogenic phenotype in NIH 3T3 fibroblast cells and RWPE prostate epithelial cells in vitro and in vivo. In contrast to the canonical KRAS G12V mutation, the UBE2L3-KRAS fusion attenuates MEK and ERK signaling in NIH 3T3 cells and instead leads to activation of AKT and p38 MAP Kinase, both of which are implicated in prostate cancer progression.

RAS proteins play a critical role in cellular physiology, development and tumorigenesis (Karnoub et al., Nat Rev Mol Cell Biol 9, 517 (July, 2008); Rodriguez-Viciana et al., Cold Spring Harb Symp Quant Biol 70, 461 (2005)). Mutations in RAS have been identified in a wide spectrum of cancers (Karnoub et al., supra), but rarely in prostate cancer (Moul et al., Prostate 20, 327 (1992)). To date, oncogenic alterations in the RAS pathway have been exclusively restricted to activating point mutations including the most commonly studied being the Gly-to-Val substitution of HRAS (Seeburg et al., Nature 312, 71 (Nov. 1-7, 1984)) and substitutions in codons 12, 13 or 61 of KRAS (Karnoub et al., supra; Schubbert, K. Shannon, G. Bollag, Nat Rev Cancer 7, 295 (April, 2007)). Chimeric transcripts of RAS genes have not been described as a class of cancer-related mutations. In previous studies, recurrent gene fusions characterized by 5' genomic regulatory elements, most commonly controlled by androgen, fused to members of the ETS family of transcription factors were identified and found to be present in over 60-70% of prostate cancers (Tomlins et al., Science 310, 644 (Oct. 28, 2005); Kumar-Sinha et al., Nat Rev Cancer 8, 497 (July, 2008)). In this study, integrative bioinformatics approaches were employed to study genomic patterns characteristic of gene fusions in cancers. This led to the characterization of a recurrent chimeric transcript of UBE2L3 fused to KRAS in a subset of human prostate cancers.

Figure 15:
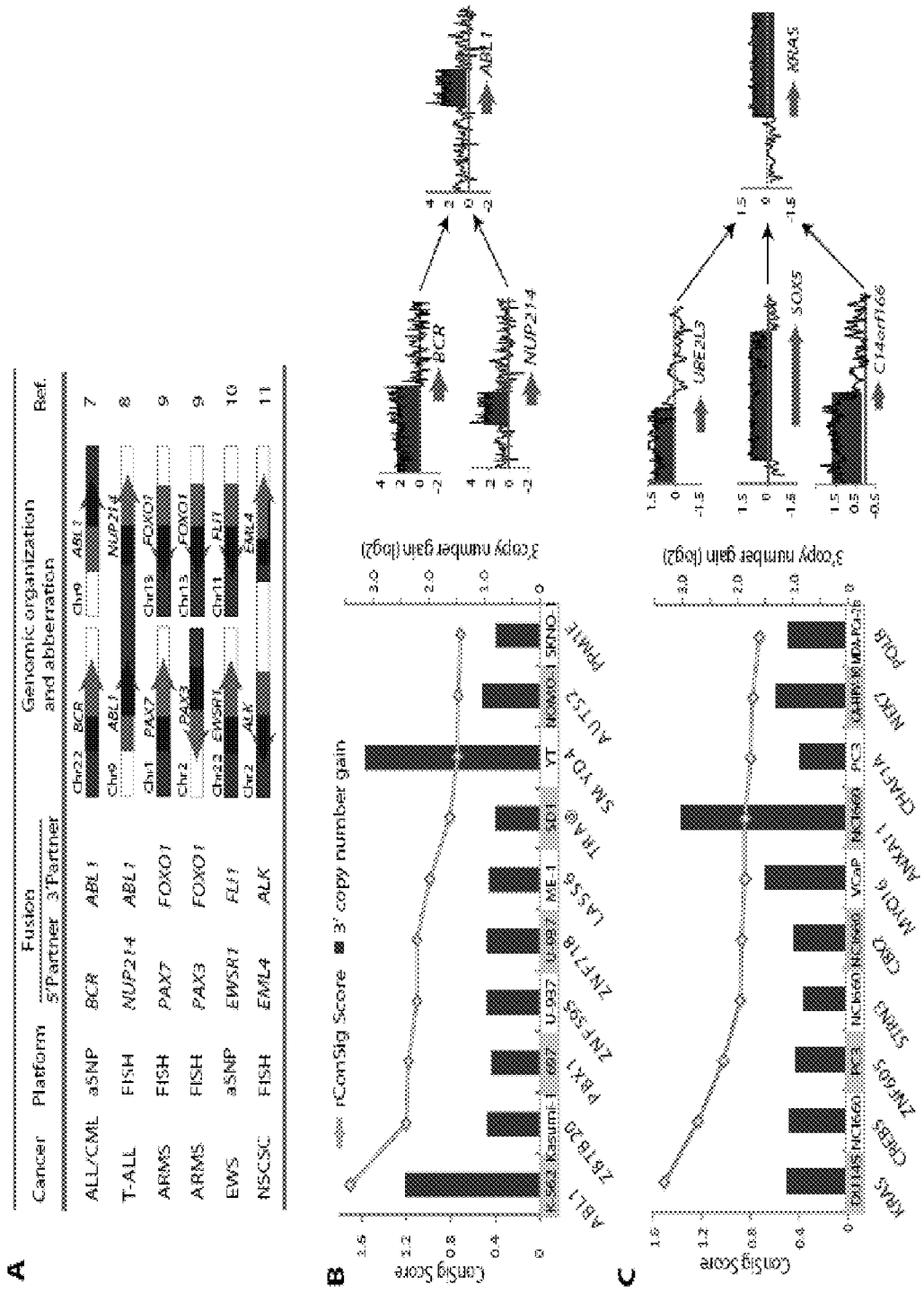
FIG. 15 shows integrative analyses of DNA copy number data that nominated KRAS as a candidate gene fusion in DU145 prostate cancer cells. (A) Table displaying known recurrent gene fusions which are accompanied by characteristic focal amplifications in a subset of patients. (B) Left panel, Amplification Breakpoint Ranking and Assembly (ABRA) analysis and ConSig scoring of 3' amplified genes from 36 leukemia cell lines identify ABL1 as a fusion gene associated with 3' amplification. (C) Left panel, as in (B), except data from a panel of prostate cancer cell lines is used.

To understand the characteristic features of recurrent gene fusions in cancer, a large-scale integrative analysis of multi-dimensional genomic data related to human cancers was carried out. This analysis revealed that in many instances, a small subset of tumors or cancer cell lines harboring a recurrent gene fusion, often display characteristic amplification at the site of genomic rearrangement (Mullighan et al., Nature 453, 110 (May 1, 2008); Graux et al., Nat Genet. 36, 1084 (October, 2004); Barr et al., Hum Mol Genet. 5, 15 (January, 1996); Ferreira et al., Oncogene 27, 2084 (Mar. 27, 2008); Koivunen et al., Clin Cancer Res 14, 4275 (Jul. 1, 2008)) (FIG. 15A). The amplification usually affected a portion of the fusion gene, and is generally considered a secondary genetic lesion associated with disease progression, drug resistance, and poor prognosis (Mullighan et al., supra; Barr et al., supra; Ferreira et al., supra; Koivunen et al., supra; Stergianou et al., Leukemia 19, 1680 (September, 2005); Attard et al., Oncogene 27, 253 (Jan. 10, 2008)). In contrast, high level copy number changes that result in the marked over-expression of oncogenes usually encompass the target genes at the center of overlapping amplifications across a panel of tumor samples. Thus, a "partially" amplified cancer gene may indicate that this gene participates in a genomic fusion event important in cancer progression. Moreover, based on the integrative analysis carried out, amplifications associated with gene fusions usually involve the 5' region of 5' partners, and 3' region of 3' partners.

Figure 19:
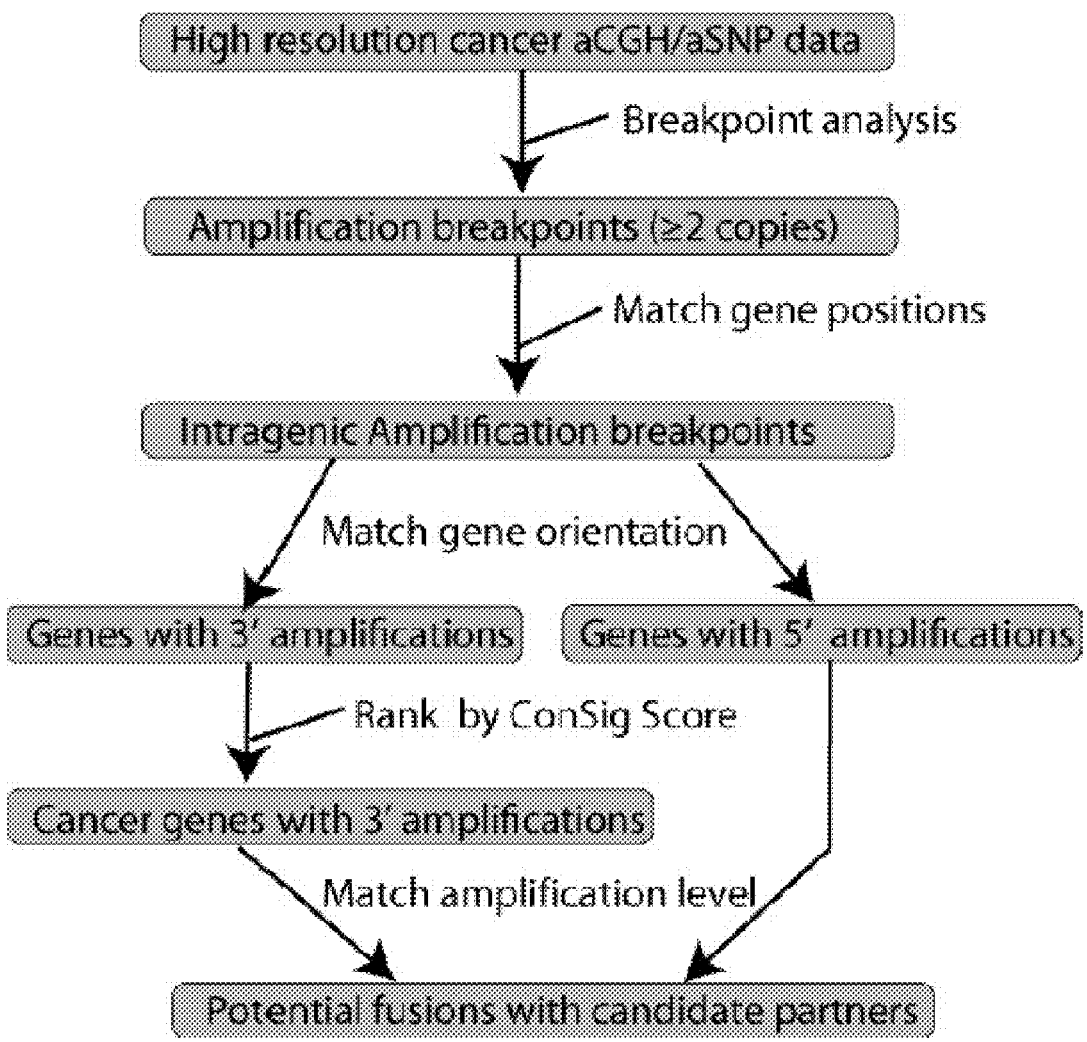
FIG. 19 shows the bioinformatics workflow of amplification breakpoint ranking and assembly (ABRA) analysis.

This observation provided the rationale to assemble putative gene fusions from amplification breakpoints by matching the amplification levels of candidate 5' and 3' partners. In order to nominate partially amplified gene fusions systematically from genomic data, ABRA was employed across a compendium of data from cancer cell lines (the workflow is described in FIG. 19). Experiments were performed on cancer cell lines initially, as breakpoint analyses are more reliable in uniform cellular populations as opposed to tumors which are made up of multiple cell types many of which are not malignant. The ABRA approach was first tested on a published single polymorphism microarray (aSNP) dataset (Mullighan et al., supra) generated from 36 leukemia cell lines including the K-562 chronic myeloid leukemia cell line known to harbor the amplified BCR-ABL1 fusion (Wu et al., Leukemia 9, 858 (May, 1995)). The relative DNA copy number data was determined and all 5' and 3' amplified genes from the 36 cell lines ($\geq 2$ copies) were identified. In this data set ABL1 was the top ranking gene with a 3' copy number increase (FIG. 15B, left panel, Table 4). The amplification levels of all 5' amplified genes in K-562 were then matched with ABL1 to nominate potential 5' partners. In total, six 5' amplified genes were found in K-562 and five matched the level of ABL1 3' amplification. After curation of the amplification breakpoints, BCR and NUP214 were nominated as ABL1 fusion partner candidates (FIG. 15B, right panel). See methods and FIG. 20 A, B for the criteria of candidate selection. This analysis demonstrated the feasibility of this method in nominating driver gene fusions from genomic datasets.

To nominate novel gene fusions in prostate cancer, this method was applied to an array of comparative genomic hybridization (aCGH) of ten prostate cancer cell lines (Table 5). The top candidate nominated in the DU145 prostate cancer cell line was KRAS exhibiting a clear breakpoint accompanied by a 3' amplification of KRAS (FIG. 15C, left).

The activation of downstream signaling intermediaries of the RAS-MAPK pathway have been observed in prostate cancer by a number of studies (Graff et al., *J Biol Chem* 275, 24500 (Aug. 11, 2000); Xu et al., *Oncogene* 25, 2987 (May 18, 2006)).

To assemble amplification breakpoints in the KRAS gene, replicate array CGH hybridizations for DU145 was performed. Matching the amplification level of KRAS with the 5' amplified genes from DU145 cells identified ten potential 5' partner candidates that were indicated by either of the two array CGH hybridizations. After curation, C14orf166, SOX5 and UBE2L3 were left as the top 5' partner candidates for KRAS (FIG. 15C, right), based on the criteria detailed in FIG. 20C.

Figure 16:
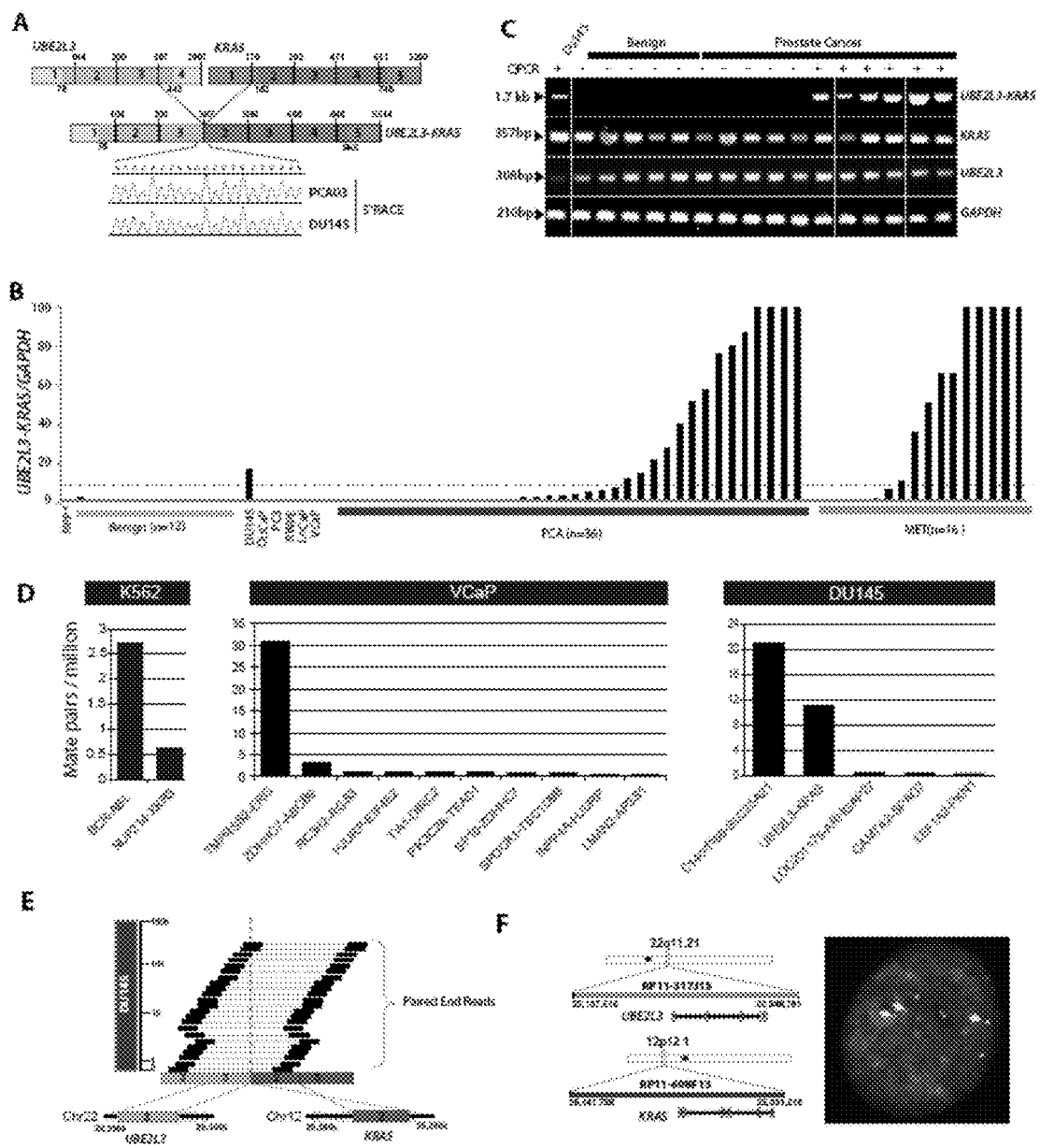
FIG. 16 shows characterization of the UBE2L3-KRAS chimera in DU145 cells and prostate cancer tissues. (A) Schematic of sequencing result from 5'RACE revealing fusion of UBE2L3 with KRAS on DU145 and a fusion positive PCA. (B) A consecutive panel of prostate cancer cell lines, benign prostate tissues, localized (PCA) and metastatic (MET) prostate cancer tissues, were analyzed for UBE2L3-KRAS mRNA expression by SYBR assay with the fusion primers. (C) Conventional RT-PCR validation with the fusion primers from the first exon of UBE2L3 and the last exon of KRAS. RT-PCR for UBE2L3, KRAS and GAPDH mRNA is also shown. (D) Histogram of the mate pair reads supported chimera nominations from K562, VCaP, and DU145 highlighting the distinction between recurrent gene fusions TMPRSS2-ERG, BCR-ABL1, UBE2L3-KRAS, and the secondary gene fusions within their respective cell lines. (E) Schematic of paired-end sequencing coverage of the fusion between UBE2L3 and KRAS in DU145. (F) Left, the genomic organizations of UBE2L3 and KRAS loci are shown in the schematic, with bars indicating the location of BAC clones. Right, interphase FISH analysis on DU145 showing three copies of fusion signals as indicated by arrows.

To experimentally validate the predicted fusions of C14orf166-KRAS, SOX5-KRAS and UBE2L3-KRAS, primer pairs were designed from the first exons of candidate 5' partners and last exon of KRAS, as well as the exons next to the breakpoints. Reverse transcription polymerase chain reaction (RT-PCR) analysis of DU145 cells identified a specific fusion band for UBE2L3-KRAS but not for the others. Subsequent sequencing of the RT-PCR product confirmed the fusion of the UBE2L3 exon 3 to the KRAS exon 2 which is schematically depicted in FIG. 16A.

Figure 21:
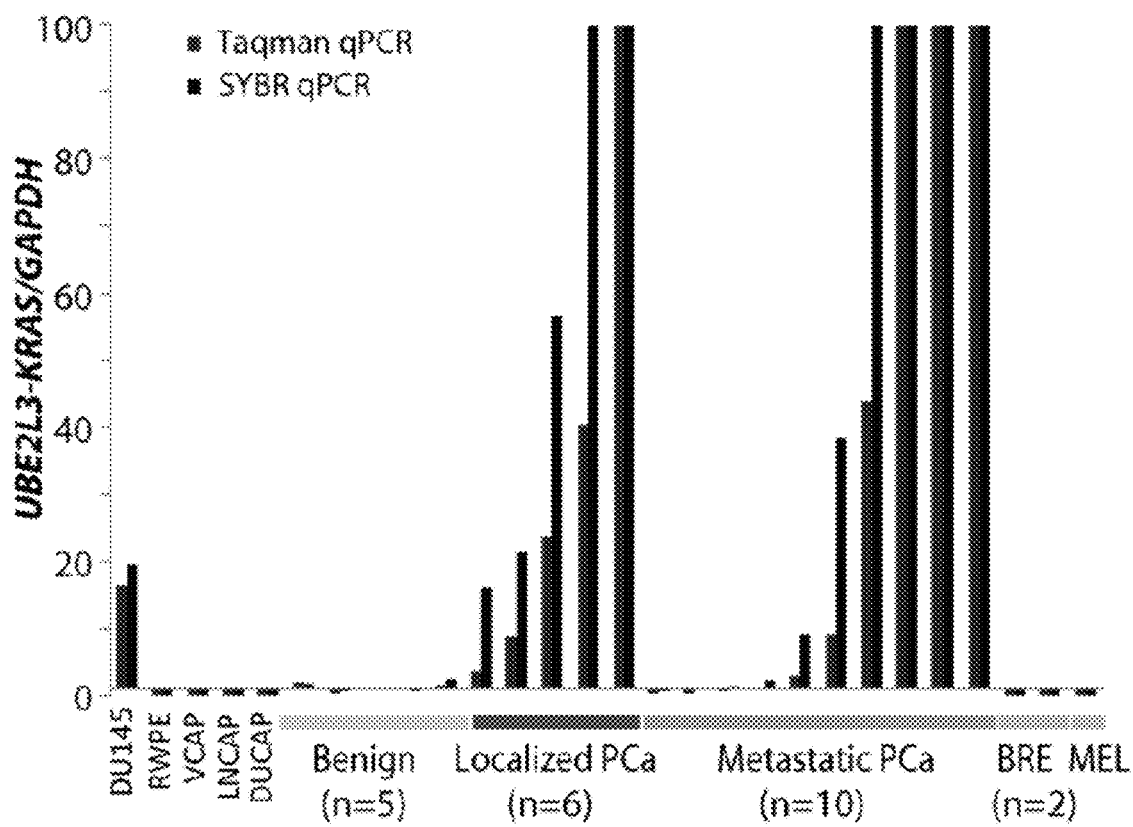
FIG. 21 shows a comparison of SYBR and Taqman fusion qPCR assay.

To assess the expression pattern of the UBE2L3-KRAS chimera, a panel of prostate cell lines and tissues was analyzed by SYBR green quantitative PCR (QPCR) as well as Taqman QPCR. In the context of cell lines, UBE2L3-KRAS expression was restricted to DU145 cells and not expressed in the other 5 prostate cell lines tested (FIG. 16B, FIG. 21). In the panel of prostate tissues from the University of Michigan Prostate SPORE program and the University of Ulm, 14 out of 36 prostate cancers (PCA), and 10 out of 16 metastatic prostate cancers (MET) exhibited elevated expression of UBE2L3-KRAS using SYBR green assays (FIG. 16B). None of the benign adjacent prostates displayed expression of this chimera. These results were further corroborated using an independently designed Taqman assay (FIG. 21) on a subset of the samples.

Figure 23:
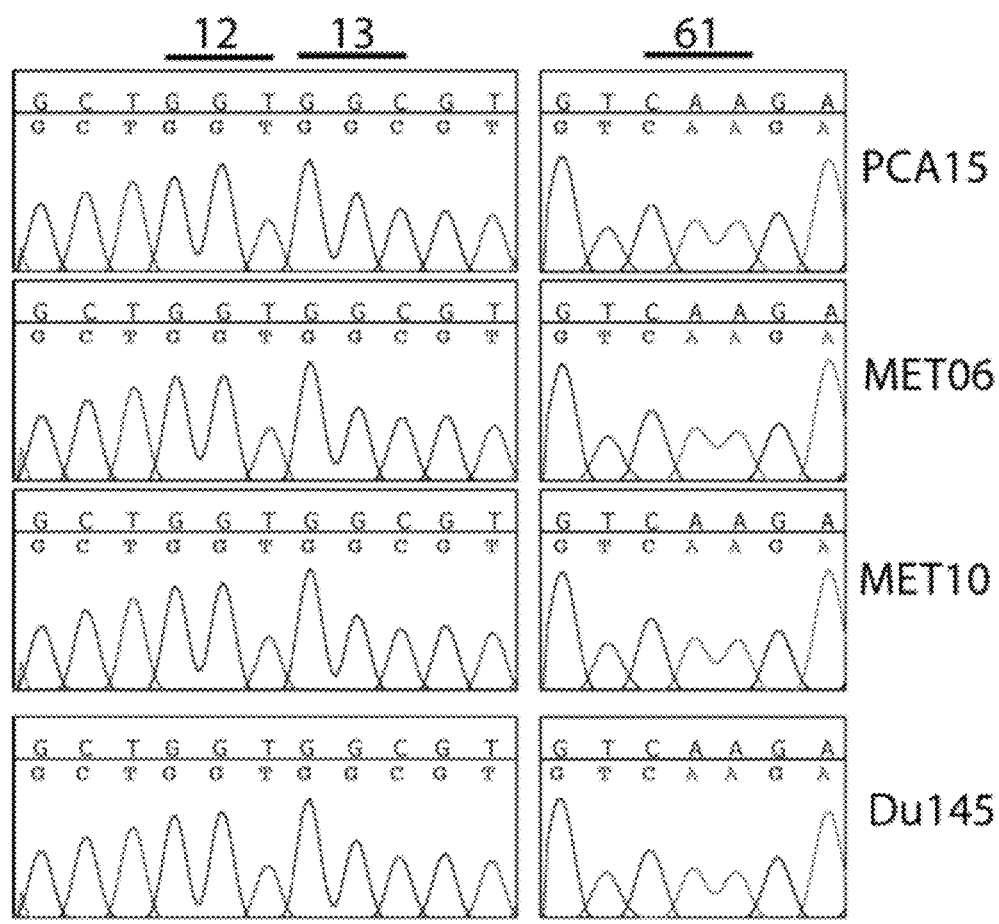
FIG. 23 shows analysis of the fusion sequences from DU145 and three fusion positive cases reveals no canonical mutation in KRAS fusion allele.

Mutual exclusivity with the ETS gene fusions described earlier (Table 7) was not observed, indicating that the UBE2L3-KRAS chimera can co-exist in a tumor harboring an ETS gene fusion. Conventional RT-PCR using primers from the first exon of UBE2L3 and the last exon of KRAS generated expected size products in prostate cancer samples determined to be UBE2L3-KRAS positive by QRT-PCR (FIG. 16C). Wild-type UBE2L3 and KRAS were expressed equally across the cohort (FIG. 16C). Subsequent sequencing of cloned RT-PCR products from three fusion positive tissues revealed the same fusion transcripts as isolated from DU145 cells (FIG. 23). Moreover, mutation analysis of these sequences did not reveal alterations in the fusion allele of KRAS (FIG. 23). The prevalence of the UBE2L3-KRAS chimera was tested on a second independent cohort of prostate cancers from Weill Cornell Medical College and the fusion transcript was detected in 18 out of 60 samples (Table 8). The products were sequenced for confirmation. Similar to the other cohorts examined, prostate cancers expressing the UBE2L3-KRAS chimera were not mutually exclusive with the presence of ETS gene fusions. To address the tissue specificity of the UBE2L3-KRAS fusion, a cohort of cancers not of prostatic origin was examined. Analysis of 36 breast cancer tissues, and 9 melanoma cell lines by qPCR did not detect the chimeric transcript, highlighting the prostate cancer specificity of UBE2L3-KRAS (Table 7).

Figure 22:
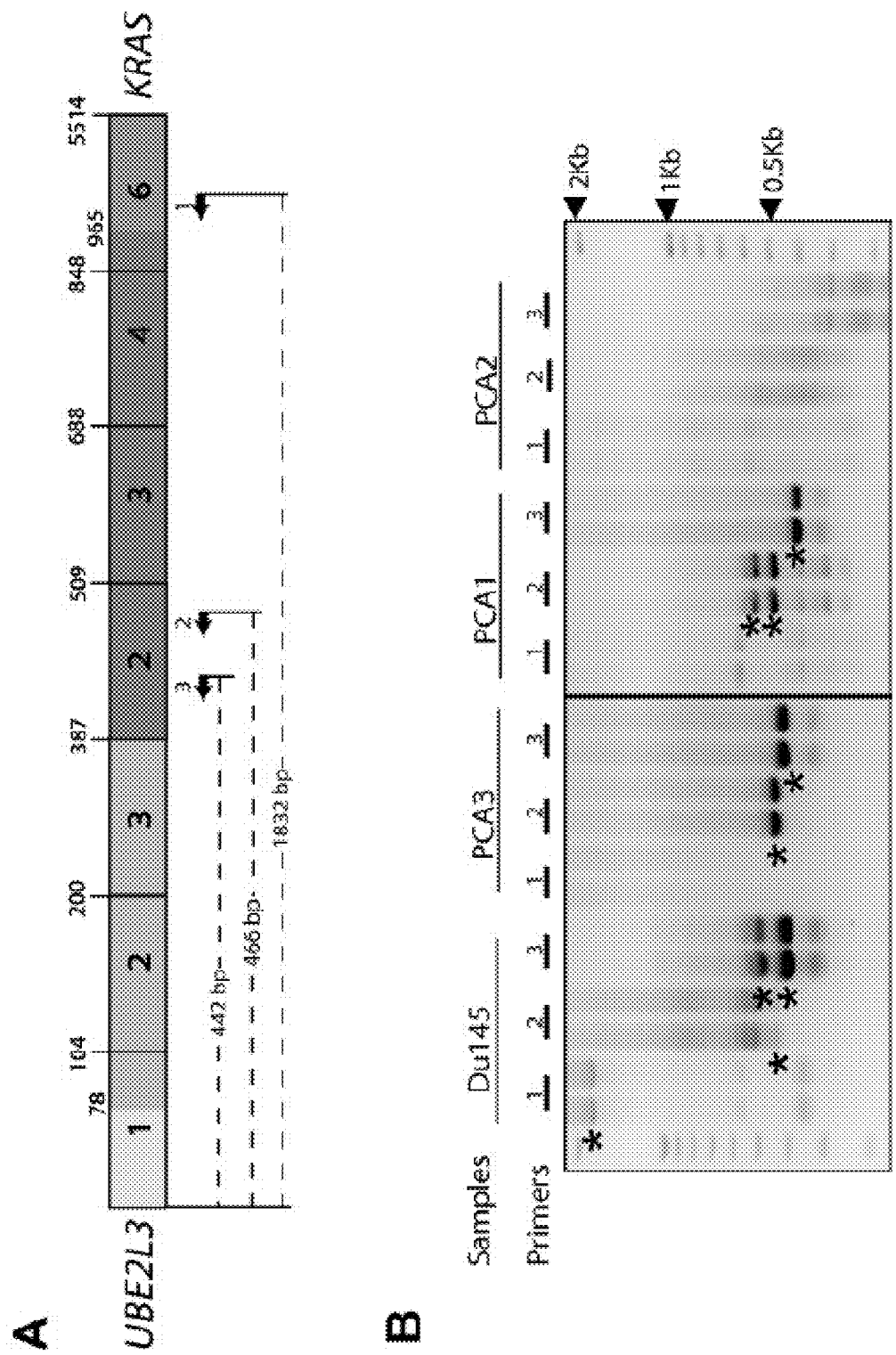
FIG. 22 shows RNA ligase-mediated rapid amplification of 5' cDNA ends (RLM-5' RACE) in DU145 and fusion positive PCA tissues. (A) The schematic depicting the positions of gene specific primers (black arrows) on KRAS part of the fusion used for RLM-5' RACE. (B) The representative gel picture of RLM-5' RACE results for DU145 and three fusion positive cases.

To characterize the 5' end of the fusion transcript, 5' RNA ligase-mediated rapid amplification of cDNA ends (RLM-RACE) was performed priming from exon 2 of KRAS using DU145 cells and four UBE2L3-KRAS positive prostate cancer tissues (FIG. 22). This confirmed the presence of UBE2L3 at the 5' end of the fusion transcript in DU145 and 3 prostate cancer samples. Sequence analysis revealed an open reading frame (ORF) of 296 amino acids extending from UBE2L3 to KRAS (FIG. 16A).

To compare the relative expression level of the UBE2L3-KRAS transcript with other putative chimeras, paired-end transcriptome sequencing was performed on DU145 cells. Similar to BCR-ABL in K-562 cells and TMPRSS2-ERG in VCaP cells (FIG. 16D) (Maher et al., *Proc Natl Acad Sci USA* (Jul. 10, 2009)), the UBE2L3-KRAS chimera was amongst the top chimeric sequences in DU145 cells demonstrating biological relevance (FIG. 16D-E). Transcriptome sequencing also identified C14orf166-SLC25A1 as the top most chimera found in DU145 cells (FIG. 16D, right panel), both of which were nominated as putative 5' and 3' fusion genes respectively by ABRA (Tables 5-6). Moreover, transcriptome sequencing data from K-562 cells not only detected the BCR-ABL chimera but the second most abundant chimera in this cell line was NUP214-XKR3 (FIG. 16D, left panel). NUP214 was also nominated as a 5' fusion partner in K562 cells by the ABRA approach (FIG. 15B, right panel).

Figure 24:
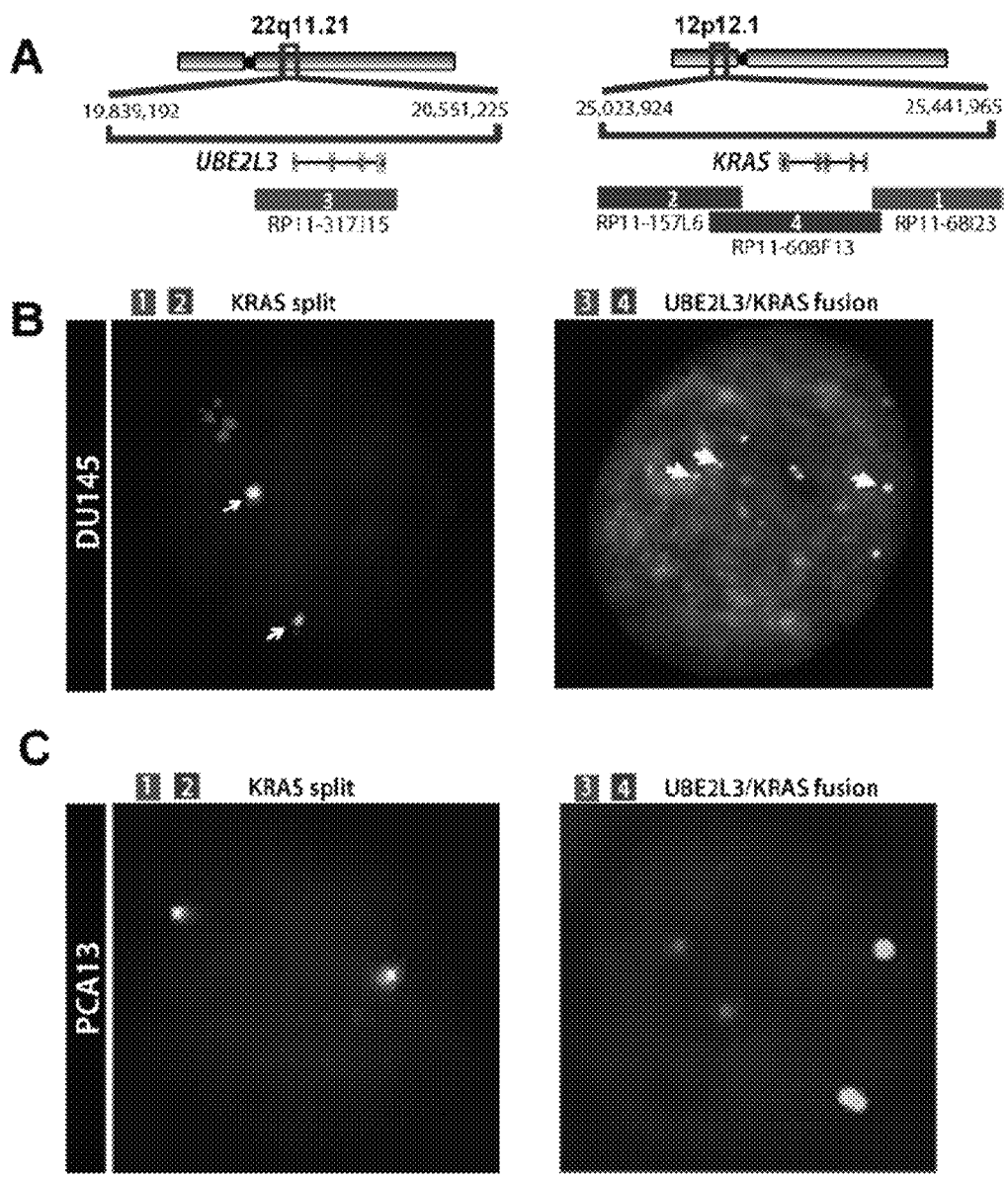
FIG. 24 shows representative FISH results in DU145 and a UBE2L3-KRAS positive prostate cancer tissue. (A) Schematic of BACs used as probes for interphase FISH. (B) FISH analysis on DU145 confirms the rearrangements at the KRAS loci and fusion of UBE2L3 to KRAS. (C) Representative FISH results on a UBE2L3-KRAS positive tissue highlighting the negative findings.

To determine whether the UBE2L3-KRAS chimera can be attributable to a DNA based rearrangement, fluorescence in situ hybridization (FISH) analysis was performed. By both KRAS split probe and UBE2L3-KRAS fusion probe FISH analysis, DU145 clearly showed a rearrangement at the KRAS genomic loci and fusion with UBE2L3 (FIG. 16F, FIG. 24B). In addition, low level amplification (3 copies) of the UBE2L3-KRAS fusion was observed, consistent with its nomination by the ABRA approach. To extend these findings into prostate tissue, FISH analysis of a series of prostate cancer tissue microarrays, which included 67 PCAs and 18 METs, was performed. Gene rearrangements were not observed in the KRAS locus; nor was fusion of UBE2L3 to KRAS observed (Table 11, FIG. 24C). Three index cases from Weill Cornell Medical College were assayed by FISH with KRAS split probes and no rearrangement was found (Table 8). This result, which is discordant from that observed in DU145 cells, indicates that prostate tumors express the UBE2L3-KRAS transcript, which is not attributable to a DNA based fusion analogous to the SLC45A3-ELK4 chimeric transcripts found in prostate cancer (Rickman et al., *Cancer Res* 69, 2734 (Apr. 1, 2009); Maher et al., *Nature* 458, 97 (Mar. 5, 2009)). Similarly, Sklar and colleagues identified the recurrent JJAZ1-SUZ12 chimera which is expressed at the mRNA level in endometrial stromal cells that appears to get "locked in" as a DNA based gene fusion in endometrial stromal tumors (Wang et al., *Science* 321, 1357 (Sep. 5, 2008)). Thus, DU145 prostate cancer cells could have been derived from a prostate cancer expressing the UBE2L3-KRAS transcript in which expression of the chimera is locked into place by genomic rearrangements picked up in cell culture.

Figure 17:
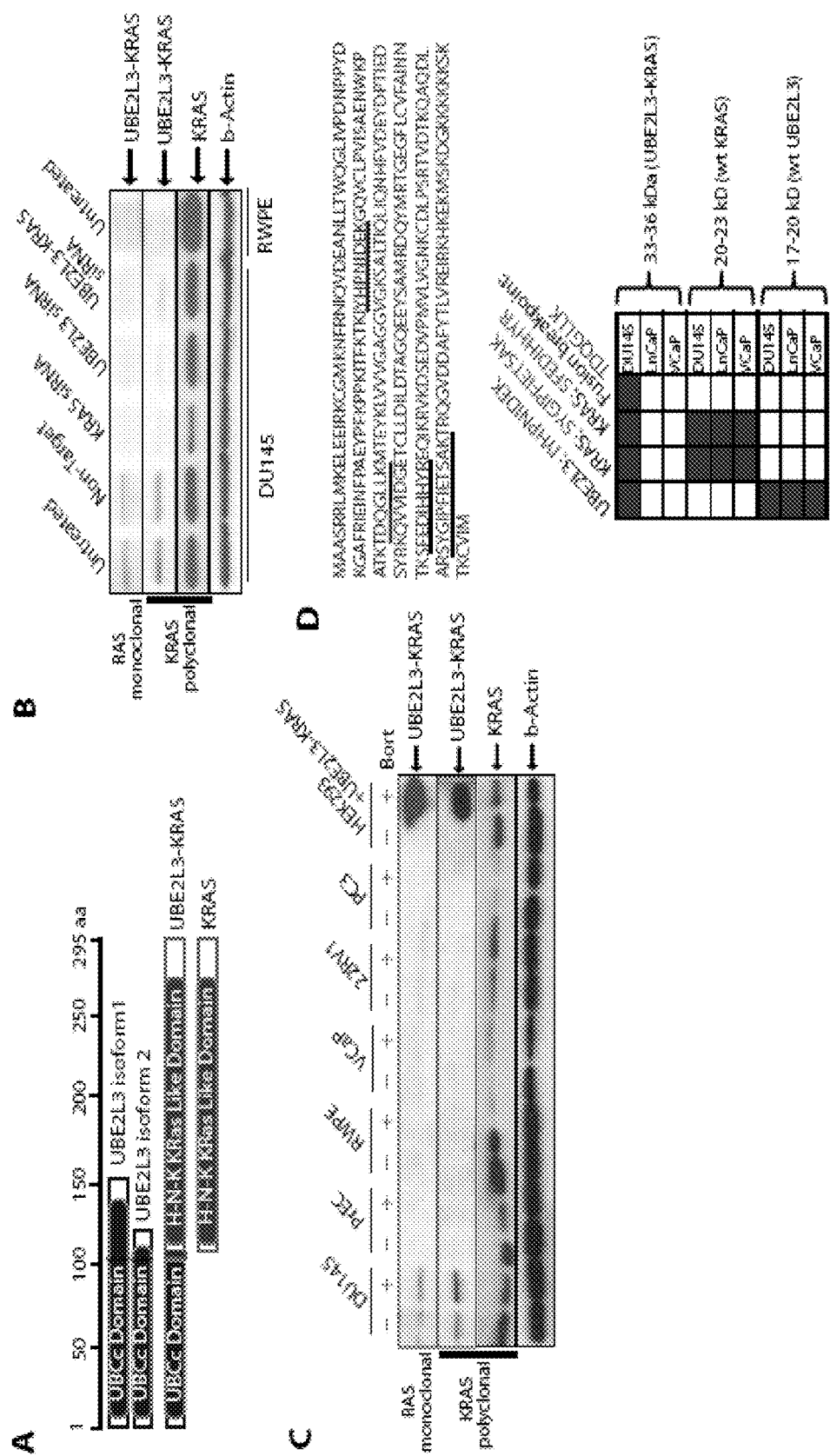
FIG. 17 shows characterization of the UBE2L3-KRAS fusion protein. (A) Schematic representations of UBE2L3, KRAS and the predicted UBE2L3-KRAS fusion protein. (B) Expression of the UBE2L3-KRAS fusion protein in DU145 cells. (C) Survey of the UBE2L3-KRAS fusion protein in a panel of prostate cancer cell lines and stabilization of protein expression with a proteosomal inhibitor, bortezomib. (D) Mass spectrometric assay for the detection of the UBE2L3-KRAS protein in DU145 cells.

Expression of the UBE2L3-KRAS protein was next examined. The predicted 296 amino acids fusion protein trims 17 amino acids from the C-terminus of UBE2L3 (FIG. 17A). The full length KRAS protein is preserved, with a 4 amino acid insertion between UBE2L3 and KRAS. Using both a monoclonal antibody raised against RAS and a polyclonal antibody raised against KRAS, a 33 kDa fusion protein was detected in addition to the 21 kDa band corresponding to wild-type KRAS (FIG. 17B,C). Specificity of the band attributed to the UBE2L3-KRAS protein was shown by knocking down expression using RNA interference against KRAS, UBE2L3 and the chimeric junction of UBE2L3-KRAS (FIG. 17B, FIG. 25A). The UBE2L3-KRAS protein was found specifically in DU145 cell and not in a panel of other prostate cell lines (FIG. 17C). Specific expression of the protein was also independently confirmed by mass spectrometric assessment of DU145 cells using a multiple reaction monitoring (MRM) assay (FIG. 17D). While wild-type KRAS and UBE2L3 were detected in DU145, VCaP and LNCaP cells, UBE2L3-KRAS was only detected in DU145 cells. Over-expression of an expression construct encoding UBE2L3-KRAS in HEK293 cells did not show protein expression (FIG. 17C). In the presence of the proteosomal inhibitor, bortezomib, expression of the fusion protein was clearly apparent indicating decreased stability of the fusion protein. Incubation of DU145 cells with bortezomib also enhanced the levels of UBE2L3-KRAS protein expression (FIG. 17C).

Figure 18:
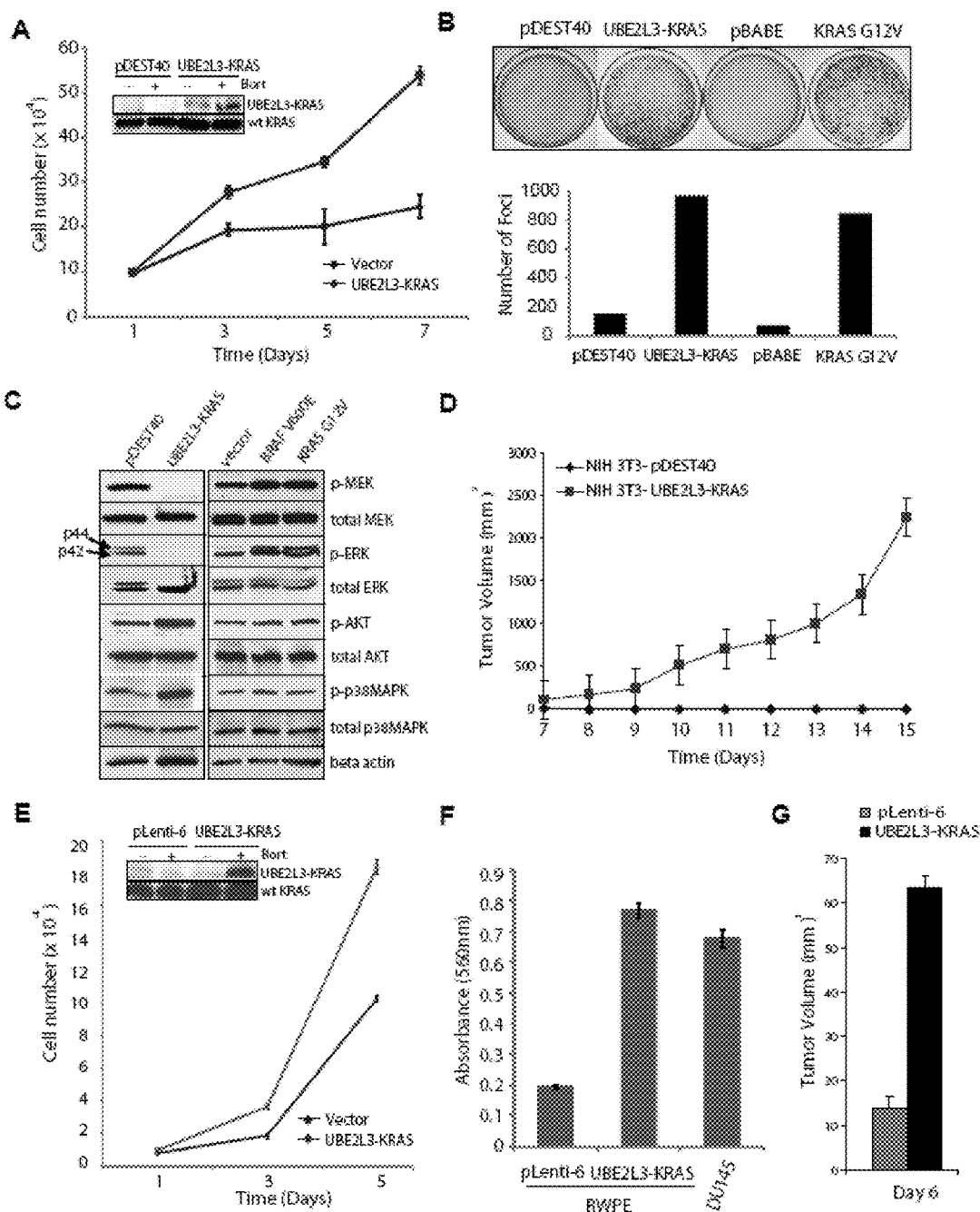
FIG. 18 shows the oncogenic potential of the UBE2L3-KRAS fusion. (A) Overexpression of UBE2L3-KRAS in NIH 3T3 cells increases cellular proliferation. (B) Overexpression of UBE2L3-KRAS induces foci formation in NIH 3T3 cells. (C) Investigation of the downstream signaling pathways engaged by the UBE2L3-KRAS fusion. (D) The UBE2L3-KRAS transfected NIH 3T3 cells form tumors in nude mice. (E) Expression of the UBE2L3-KRAS fusion in RWPE benign prostate epithelial cells leads to increased cellular proliferation. (F) RWPE stable cells expressing the UBE2L3-KRAS fusion showed increased cell invasion potential. (G) The UBE2L3-KRAS infected RWPE cells form transient tumors in mice.
Figure 26:
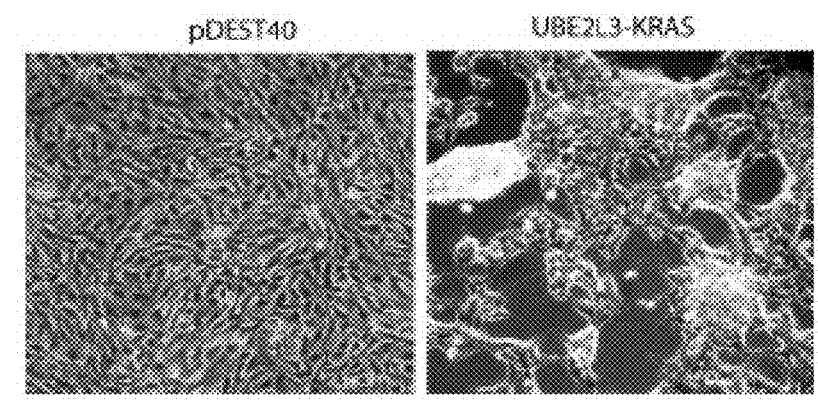
FIG. 26 shows NIH 3T3 fibroblasts expressing the UBE2L3-KRAS fusion lost normal fibroblast morphology in contrast to the pDEST40 vector control.
Figure 27:
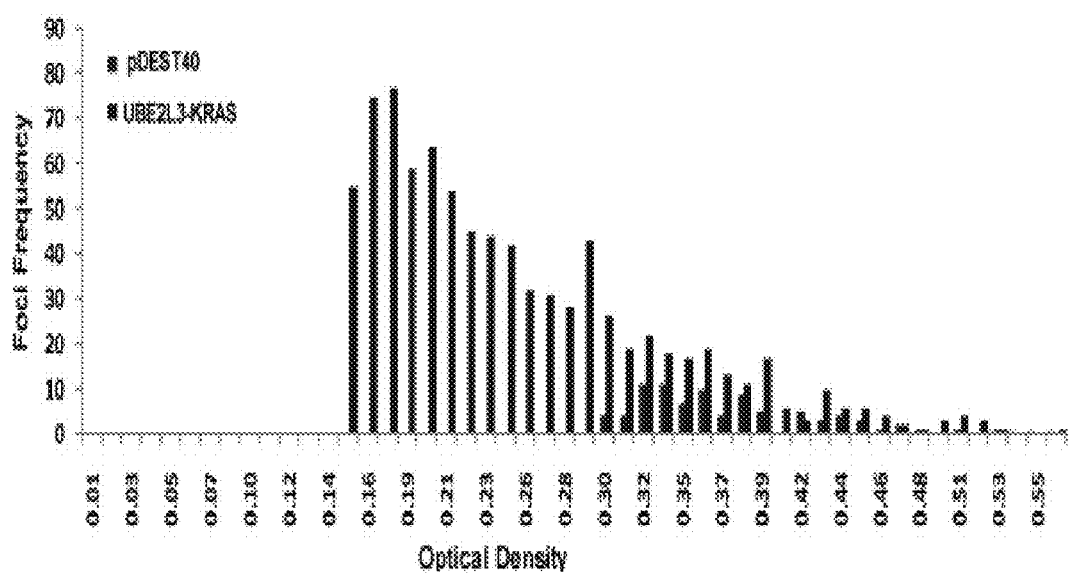
FIG. 27 shows a comparison of the foci density of NIH 3T3 cells expressing the UBE2L3-KRAS fusion or pDEST40 vector.
Figure 28:
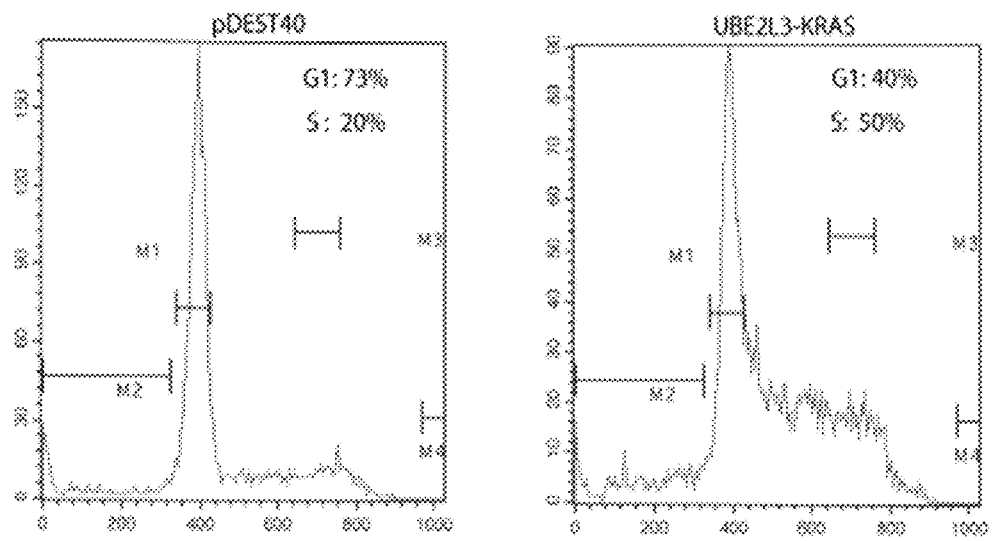
FIG. 28 shows that NIH 3T3 cells expressing the UBE2L3-KRAS fusion show an increase in the S phase.
Figure 29:
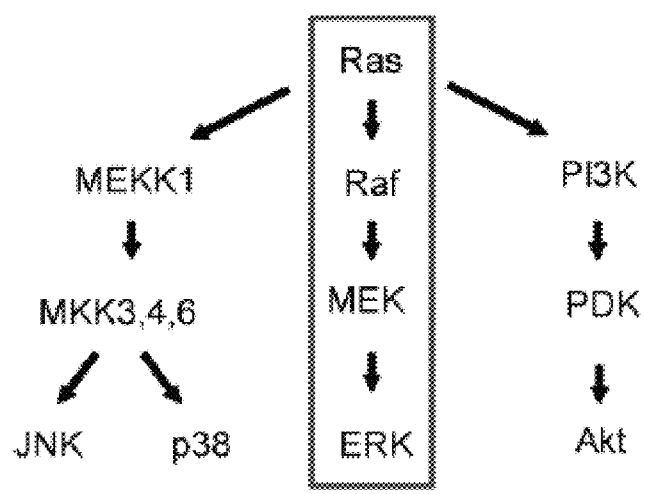
FIG. 29 shows a schematic of Ras signaling pathways.

To determine the function of the UBE2L3-KRAS protein, it was over-expressed in NIH 3T3 cells (FIG. 25B), a system classically used to study RAS biology (Seeburg et al., supra; Der et al., Proc Natl Acad Sci USA 79, 3637 (June, 1982)). Enforced expression of UBE2L3-KRAS induced loss of fibroblast morphology (FIG. 26) and increased cell proliferation (FIG. 18A) and foci formation (FIG. 18B, FIG. 27). Cell cycle analysis revealed an increase in the S phase fraction of cells (FIG. 28). To interrogate the potential RAS-related signaling pathways engaged by UBE2L3-KRAS in NIH 3T3 cells a series of immunoblot analyses was performed on key signaling intermediaries (FIG. 29). As reported in the literature for NIH 3T3 cells, KRAS is a stronger inducer of the MEK/ERK cascade; whereas HRAS is a stronger activator of the PI3K/AKT pathway (Zhu et al., J Biol Chem 279, 37398 (Sep. 3, 2004)). UBE2L3-KRAS over-expression attenuated endogenous MEK and ERK phosphorylation indicating a potential dominant negative effect of the chimeric product on RAS signaling (FIG. 18C). Furthermore, not only was there an attenuation of MEK-ERK signaling by the UBE2L3-KRAS fusion, but a shift to AKT and p38 MAP Kinase activation was observed, pathways which have been implicated in prostate cancer by a number of studies (Graff et al., supra; Xu et al., supra).

Figure 30:
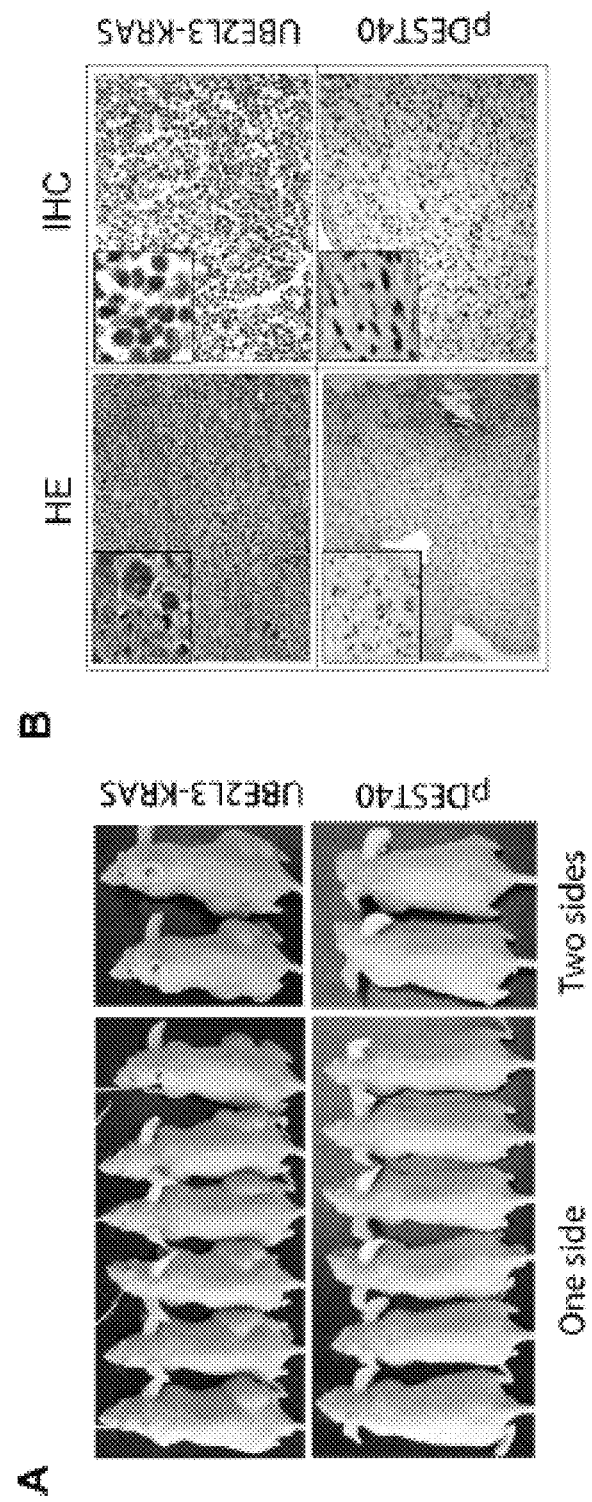
FIG. 30 shows photographs and pathology of NIH 3T3 xenograft models. (A) The photographs of the mice bearing the NIH 3T3 xenograft tumors expressing UBE2L3-KRAS fusion (upper) and the pDEST40 vector (lower). (B) The pathology of NIH 3T3 xenograft tissues. Left panel, xenograft tissues excised from NIH 3T3 fusion expressing tumor bearing mice were stained using hematoxylin and eosin (HE). Right panel, Ki-67 immunohistochemical (IHC) staining of xenograft tissues showing 98% of tumor nuclei (upper) versus 17% of control tissue nuclei (lower) are positive for Ki-67.

To determine the effects of UBE2L3-KRAS expression on tumor growth in vivo, nude mice were implanted with the stable NIH 3T3 vector control cells or NIH 3T3 UBE2L3-KRAS chimera expressing cells. Tumor formation was observed in the UBE2L3-KRAS expressing cells but not the vector transfected cells (FIG. 18D, FIG. 30).

To investigate the role of the UBE2L3-KRAS chimera in a prostate background, the fusion was overexpressed in RWPE prostate epithelial cells (FIG. 25C). In order to observe expression of the fusion protein, proteosomal inhibition with bortezomib was required (FIG. 18E, insert), indicating that the fusion protein is highly unstable. Over-expression of the UBE2L3-KRAS chimera in RWPE cells led to increased cellular proliferation, cell invasion and a transient increase of tumor growth in nude mice (FIG. 18E-G). Unlike NIH 3T3 xenografts, RWPE xenografts overexpressing UBE2L3-KRAS exhibited tumor regression over several weeks indicating that in the RWPE system, additional alterations are required to maintain tumor growth longer term.

In summary, this example describes an integrative bioinformatics approach to understand common characteristics of recurrent gene fusions in cancer using a compilation of published genomic datasets matched with gene rearrangement data. This led to the nomination of the UBE2L3-KRAS chimera in the DU145 prostate cancer cell line. This genomic fusion was experimentally confirmed to exist at the RNA and DNA level in DU145 cells. In prostate tumors it was found that the UBE2L3-KRAS chimeric transcript is highly expressed in 30-40% of prostate cancers (from 3 independent cohorts, Table 9) but is undetectable or at low levels in benign adjacent tissues or in other cancer types. DNA based alteration was not detected in prostate cancer tissues that accounts for the creation of this chimeric transcript, indicating that altered splicing mechanisms may be a prerequisite for the generation of a genomic fusion. This is analogous to the altered splicing mechanisms described for the JJAZ1-SUZ12 chimera in endometrial stromal tissues (Wang et al., supra). It was determined that the UBE2L3-KRAS chimera can co-exist with ETS gene fusions in prostate cancer.

The UBE2L3-KRAS chimera encodes a protein in which the N-terminus encompasses most of the UBE2L3 protein with a small truncation in frame with full length KRAS. This fusion protein is unstable and requires proteosomal inhibition to be observed readily. UBE2L3 is a ubiquitin-conjugating enzyme (E2) (Moynihan et al., Genomics 51, 124 (Jul. 1, 1998)). Furthermore, there is already considerable evidence that ubiquitination pathways are important in tumorigenesis (Hoeller et al., Nature 458, 438 (Mar. 26, 2009)).

While a number of oncogenic activating point mutations of KRAS have been identified, this is the first description of a mutant chimeric version of KRAS that is oncogenic and thus represents a new class of cancer-related alteration. As activating point mutations in KRAS are rare in prostate cancer, the UBE2L3-KRAS chimera also represents the KRAS alteration specific to prostate cancer as there are a number of studies supporting the role of KRAS and MAPK pathways in prostate cancer progression (Graff et al., supra; Chen et al., supra). Both KRAS G12V and UBE2L3-KRAS exhibit an oncogenic phenotype in vitro and in vivo, UBE2L3-KRAS over-expression leads to attenuation, rather than activation, of the MEK-ERK pathway. Instead, the KRAS fusion directs signaling down the AKT and p38 MAPK pathways.

TABLE 4

The result of ABRA ranking analysis in a panel of 36 leukemia cell lines. Cell lines that do not harbor partially amplified genes are not shown.

| Cell line | Gene | Chr | Gene position | Breakpoint position | Type | Level of amplification* | ConSig Score | Breakpoint curation[#] | Cancer Gene[$] |
|---|---|---|---|---|---|---|---|---|---|
| K-562 | ABL1 | chr9 | 132579089-132752883 | 132538227-132601560 | 3'amp | 2.43 | 1.70 | | Yes |
| Kasumi-1 | ZBTB20 | chr3 | 115540207-116348817 | 115654416-115688377 | 3'amp | 0.97 | 1.20 | | |
| 697 | PBX1 | chr1 | 162795561-163082934 | 163015749-163027242 | 3'amp | 0.88 | 1.18 | | Yes |
| U-937 | ZNF595 | chr4 | 43227-78099 | 34101-59713 | 3'amp | 0.97 | 1.10 | | |
| U-937 | ZNF718 | chr4 | 43250-146491 | 34101-59713 | 3'amp | 0.97 | 1.10 | | |
| ME-1 | LASS6 | chr2 | 169021081-169339398 | 169307675-169332507 | 3'amp | 0.92 | 0.98 | | |

TABLE 4-continued

The result of ABRA ranking analysis in a panel of 36 leukemia cell lines. Cell lines that do not harbor partially amplified genes are not shown.

| Cell line | Gene | Chr | Gene position | Breakpoint position | Type | Level of amplification* | ConSig Score | Breakpoint curation# | Cancer Gene$ |
|---|---|---|---|---|---|---|---|---|---|
| SD1 | TRA@ | chr14 | 21159897-22090915 | 21480460-21483625 | 3'amp | 0.82 | 0.80 | | |
| YT | SMYD4 | chr17 | 1629603-1679844 | 1668363-1723617 | 3'amp | 3.15 | 0.74 | | |
| NOMO-1 | AUTS2 | chr7 | 68702255-69895790 | 68965752-69022498 | 3'amp | 1.04 | 0.73 | | |
| SKNO-1 | PPM1E | chr17 | 54188231-54417319 | 54195586-54264925 | 3'amp | 0.80 | 0.71 | | |
| Kasumi-1 | DCUN1D4 | chr4 | 52404033-52477760 | 48758236-52409268 | 3'amp | 0.81 | 0.66 | | |
| UOCB1 | TRIT1 | chr1 | 40079315-40121764 | 40081505-40116019 | 3'amp | 1.33 | 0.63 | | |
| NB4 | RASIP1 | chr19 | 53915654-53935782 | 53932963-53999660 | 3'amp | 2.49 | 0.61 | | |
| Kasumi-1 | BOC | chr3 | 114414065-114488996 | 114397446-114403958 | 3'amp | 0.89 | 0.59 | | |
| Jurkat | LSAMP | chr3 | 117011832-117647068 | 117435489-117435958 | 3'amp | 1.00 | 0.56 | | |
| UOCB1 | SSH2 | chr17 | 24977091-25281144 | 25114150-25145292 | 3'amp | 1.43 | 0.56 | | |
| NB4 | CD72 | chr9 | 35599976-35608408 | 35605896-35672585 | 3'amp | 1.80 | 0.50 | | |
| CMK | TNFSF18 | chr1 | 171277074-171286679 | 171279427-171335867 | 3'amp | 1.12 | 0.46 | | |
| NOMO-1 | GNE | chr9 | 36204438-36248401 | 36227241-36296809 | 3'amp | 1.16 | 0.45 | | |
| YT | NMT1 | chr17 | 40494206-40541910 | 40524918-40529353 | 3'amp | 1.08 | 0.43 | | |
| K-562 | GRID1 | chr10 | 87349292-88116230 | 87835186-87847802 | 3'amp | 1.03 | 0.38 | | |
| BV173 | CRB1 | chr1 | 195504031-195714208 | 195630571-195665893 | 3'amp | 0.91 | 0.34 | | |
| PL21 | KIF21A | chr12 | 37973297-38123185 | 38082147-38177337 | 3'amp | 1.08 | 0.32 | | |
| SKNO-1 | TMEM135 | chr11 | 86426713-86712220 | 86486132-86489947 | 3'amp | 0.76 | 0.27 | | |
| Kasumi-1 | TMEM100 | chr17 | 51151989-51155141 | 51157187-51193501 | 3'amp | 0.91 | 0.27 | | |
| NB4 | TMTC1 | chr12 | 29545024-29828959 | 29633231-29639626 | 3'amp | 1.05 | 0.25 | | |
| CMK | DEFB115 | chr20 | 29309128-29311096 | 28119554-29309964 | 3'amp | 1.52 | 0.18 | | |
| BV173 | IGL@ | chr22 | 20710659-21595085 | 20987900-21049884 | 3'amp | 1.15 | 0.16 | | |
| Kasumi-1 | C17orf57 | chr17 | 42756346-42873677 | 42768483-42771996 | 3'amp | 0.80 | 0.13 | | |
| SKNO-1 | FOXD4L2 | chr9 | 69465527-69468635 | 67813967-68171592 | 3'amp | 0.86 | 0.00 | | |
| MV4-11 | C1orf150 | chr1 | 245779072-245806482 | 245731777-245732788 | 3'amp | 0.80 | 0.00 | | |
| K-562 | DGCR5 | chr22 | 17338027-17362141 | 17317513-17347582 | 3'amp | 1.51 | 0.00 | | |
| BV173 | IGLV7-46 | chr22 | 21054162-21054455 | 20987900-21049884 | 3'amp | 1.15 | | Not acceptable (5) | |
| CMK | CHEK1 | chr11 | 125001547-125030847 | 125017829-125050645 | 3'amp | 0.86 | | Not acceptable (6) | |
| CMK | UBE4B | chr1 | 10015630-10163884 | 10145592-10158626 | 3'amp | 0.76 | | Not acceptable (6) | |
| CMK | DNM3 | chr1 | 170077261-170648480 | 170339258-170384303 | 3'amp | 1.21 | | Not acceptable (5) | |
| CMK | ERI3 | chr1 | 44459329-44593526 | 44470260-44503655 | 3'amp | 0.92 | | Not acceptable (5) | |
| Jurkat | TERT | chr5 | 1306282-1348159 | 1322060-1375087 | 3'amp | 0.77 | | Not acceptable (6) | |
| Kasumi-1 | REST | chr4 | 57468799-57493097 | 57443410-57460303 | 3'amp | 1.67 | | Not acceptable (5) | |
| MV4-11 | LOC646479 | chr8 | 17333702-17373392 | 17367002-17367251 | 3'amp | 1.34 | | Not acceptable (5) | |
| MV4-11 | CCDC25 | chr8 | 27646752-27686089 | 27660240-27663535 | 3'amp | 1.20 | | Not acceptable (5) | |
| NOMO-1 | STARD13 | chr13 | 32575307-32757892 | 32941750-32950412 | 3'amp | 0.84 | | Not acceptable (4) | |
| PL21 | FAM155A | chr13 | 106618880-107317084 | 107054542-107088262 | 3'amp | 2.21 | | Not acceptable (5) | |
| SD1 | TRAV15 | chr14 | 21488174-21488717 | 21480460-21483625 | 3'amp | 0.82 | | Not acceptable (5) | |
| SKNO-1 | FNDC3B | chr3 | 173312936-173601181 | 173467998-173474266 | 3'amp | 1.09 | | Not acceptable (1) | |
| SUPB-15 | FAM49B | chr8 | 130922898-131021182 | 130947000-131041167 | 3'amp | 2.18 | | Not acceptable (5) | |
| TOM-1 | LOC729894 | chr15 | 20304046-20344434 | 20329239-20335459 | 3'amp | 0.77 | | Not acceptable (6) | |
| YT | IRF4 | chr6 | 336760-356193 | 323970-340634 | 3'amp | 0.89 | | Not acceptable (6) | |
| YT | SKAP1 | chr17 | 43565804-43862551 | 4359289-43599947 | 3'amp | 0.93 | | Not acceptable (3) | |

*level of amplification shows the difference of relative quantification of DNA copy number data at the amplification breakpoints
Situations when breakpoint is not acceptable
(1) Multiple intragenic breakpoints;
(2) The candidate is not the gene closest to the amplification breakpoint;
(3) The amplification starts from existing copy number increase and the breakpoint is not sharp;
(4) The breakpoint locates at the centromere or the end of the chromosome;
(5) The breakpoint is the result of a small deletion within an amplification;
(6) The breakpoint is found in a majority of samples.
$Cancer genes are defined by cancer gene census

TABLE 5

The result of ABRA ranking analysis in a panel of 10 prostate cancer cell lines.
Cell lines that do not harbor partially amplified genes are not shown.

| Cell line | Gene | Chr | Gene position | Breakpoint position | Type | Level of amplification* | ConSig Score | Breakpoint curation# | Cancer Gene$ |
|---|---|---|---|---|---|---|---|---|---|
| DU145.1 | KRAS | chr12 | 25249446-25295121 | 25289615-25308034 | 3'amp | 1.10 | 1.51 | | Yes |
| NCI660 | CREB5 | chr7 | 28112179-28638749 | 28602533-28619165 | 3'amp | 1.05 | 1.23 | | |
| PC3 | ZNF605 | chr12 | 132108397-132143218 | 132153240-132181375 | 3'amp | 0.95 | 1.02 | | |
| NCI660 | STRN3 | chr14 | 30432761-30565340 | 30459890-30475453 | 3'amp | 0.79 | 0.88 | | |
| NCI660 | CRX2 | chr17 | 75366587-75375973 | 75345225-75368067 | 3'amp | 0.96 | 0.87 | | |
| VCaP | MYO16 | chr13 | 108046500-108658356 | 108470109-108485416 | 3'amp | 1.48 | 0.84 | | |
| NCI660 | ANXA11 | chr10 | 81904859-81955308 | 81952099-81996286 | 3'amp | 3.00 | 0.84 | | |
| PC3 | CHAF1A | chr19 | 4353659-4394393 | 4343191-4350902 | 3'amp | 0.86 | 0.80 | | |
| CA.hpv.10 | NEK7 | chr1 | 194933338-195020426 | 194997907-195020336 | 3'amp | 1.29 | 0.78 | | |

TABLE 5-continued

The result of ABRA ranking analysis in a panel of 10 prostate cancer cell lines.
Cell lines that do not harbor partially amplified genes are not shown.

| Cell line | Gene | Chr | Gene position | Breakpoint position | Type | Level of amplification* | ConSig Score | Breakpoint curation# | Cancer Gene$ |
|---|---|---|---|---|---|---|---|---|---|
| MDAPCa.2b | POLB | chr8 | 42315186-42348470 | 42308627-42321600 | 3'amp | 1.06 | 0.73 | | |
| C4.2B | TNFSF12 | chr17 | 7393098-7401930 | 7388929-7401533 | 3'amp | 0.86 | 0.71 | | |
| DU145.1 | GPSM3 | chr6 | 32266521-32271278 | 32268003-32297149 | 3'amp | 0.89 | 0.70 | | |
| PC3 | PARG | chr10 | 50696332-51041337 | 50717613-50764988 | 3'amp | 1.58 | 0.70 | | |
| PC3 | PIPN20A | chr10 | 45970128-48447930 | 46371243-46396163 | 3'amp | 0.76 | 0.69 | | |
| C4.2B | CHFR | chr12 | 132027287-132074534 | 132043499-132057649 | 3'amp | 0.78 | 0.69 | | |
| NCI660 | POLQ | chr3 | 122632963-122747519 | 122747877-122772579 | 3'amp | 0.78 | 0.62 | | |
| NCI660 | MIS12 | chr17 | 5330970-5334852 | 5329458-5332851 | 3'amp | 1.10 | 0.60 | | |
| PC3 | RINT1 | chr7 | 104766482-104802075 | 104742899-104771013 | 3'amp | 0.89 | 0.59 | | |
| PC3 | DHX8 | chr17 | 38916859-38957206 | 38922343-38940540 | 3'amp | 0.90 | 0.55 | | |
| C4.2B | RHOG | chr11 | 3804787-3818760 | 3823067-3843370 | 3'amp | 0.78 | 0.55 | | |
| NCI660 | DULLARD | chr17 | 7087882-7095983 | 7104658-7116744 | 3'amp | 0.99 | 0.54 | | |
| NCI660 | KRT7 | chr12 | 50913220-50928976 | 50888386-50904894 | 3'amp | 1.58 | 0.54 | | |
| PC3 | PHLDA3 | chr1 | 198166279-198169956 | 198168603-198184752 | 3'amp | 1.87 | 0.53 | | |
| PC3 | HEATR4 | chr14 | 73014945-73095404 | 73082250-73092018 | 3'amp | 1.22 | 0.51 | | |
| DU145.1 | CCDC130 | chr19 | 13719752-13735106 | 13663749-13726338 | 3'amp | 1.10 | 0.44 | | |
| DU145.1 | PRSS36 | chr16 | 31057749-31068888 | 31065342-31081708 | 3'amp | 0.88 | 0.43 | | |
| NCI660 | CLDN7 | chr17 | 7104183-7106513 | 7104658-7116744 | 3'amp | 0.99 | 0.31 | | |
| NCI660 | CLDN7 | chr17 | 7104183-7106513 | 7104658-7116744 | 3'amp | 0.99 | 0.31 | | |
| C4.2B | TNFSF12-TNFSF13 | chr17 | 7393139-7405649 | 7388929-7401533 | 3'amp | 0.86 | 0.29 | | |
| DU145.1 | SLC25A21 | chr14 | 36218828-36711616 | 36250273-36264559 | 3'amp | 1.03 | 0.23 | | |
| PC3 | CCDC109A | chr10 | 74121894-74317456 | 74212793-74231229 | 3'amp | 2.10 | 0.22 | | |
| VCaP | SIL1 | chr5 | 138310310-138561964 | 138352012-138377215 | 3'amp | 1.23 | 0.21 | | |
| PC3 | PTPN20B | chr10 | 45970128-48447930 | 46371243-46396163 | 3'amp | 0.76 | 0.18 | | |
| NCI660 | TMLHE | chrX | 154283476-154406301 | 154405100-154429859 | 3'amp | 1.29 | 0.11 | | |
| MDAPCa.2b | CCDC36 | chr3 | 49210864-49270159 | 49200589-49211507 | 3'amp | 0.76 | 0.00 | | |
| VCaP | C6orf106 | chr6 | 34663049-34772603 | 34757380-34808070 | 3'amp | 1.91 | 0.00 | | |
| X22RV1 | DTWD2 | chr5 | 118203134-118352139 | 118249938-118267673 | 3'amp | 0.84 | 0.00 | | |
| C4.2B | UBE2T | chr1 | 199032442-199042734 | 199032584-199065829 | 3'amp | 1.12 | | Not acceptable (5) | |
| C4.2B | PPPIR12B | chr1 | 199049492-199289354 | 199194296-199208949 | 3'amp | 1.01 | | Not acceptable (5) | |
| C4.2B | SENP3 | chr17 | 7406042-7416009 | 7388929-7401533 | 3'amp | 0.86 | | Not acceptable (2) | |
| C4.2B | TNFSF13 | chr17 | 7402339-7405641 | 7388929-7401533 | 3'amp | 0.86 | | Not acceptable (2) | |
| DU145.1 | PBX2 | chr6 | 32260495-32265941 | 32268003-32297149 | 3'amp | 0.89 | | Not acceptable (2) | |
| DU145.1 | AGER | chr6 | 32256723-32260001 | 32268003-32297149 | 3'amp | 0.89 | | Not acceptable (2) | |
| NCI660 | HMI3 | chr20 | 29565901-29621029 | 29557170-29575050 | 3'amp | 0.91 | | Not acceptable (6) | |
| NCI660 | LOC541473 | chr7 | 74665887-74669359 | 73431763-73452181 | 3'amp | 0.77 | | Not acceptable (5) | |
| NCI660 | STAG3L2 | chr7 | 71913147-73751326 | 73431763-73452181 | 3'amp | 0.77 | | Not acceptable (3) | |
| PC3 | KLHL17 | chr1 | 936109-941162 | 919074-931088 | 3'amp | 0.80 | | Not acceptable (5) | |
| X22RV1 | UBE2T | chr1 | 199032442-199042734 | 199032584-199065829 | 3'amp | 0.85 | | Not acceptable (5) | |
| X22RV1 | PPPIR12B | chr1 | 199049492-199289354 | 199194296-199208949 | 3'amp | 0.77 | | Not acceptable (5) | |

TABLE 6

Matching the amplification level of 5' amplified genes with ABL1 and KRAS on K-562 and DU145 respectively nominates their candidate 5' partners. 3' genes seeding the breakpoint assembling analysis are highlighted by bold.

| Cell line | Gene | Chr | Gene Position | Breakpoint position | Type | Level of amplification* | Breakpoint curation** |
|---|---|---|---|---|---|---|---|
| K-562 | BCR | chr22 | 21852552-21990224 | 21953284-21965924 | 5'amp | 2.89 | |
| K-562 | FBXW4P1 | chr22 | 21934791-21937180 | 21953284-21965924 | 5'amp | 2.89 | Not acceptable (2) |
| K-562 | GPC5 | chr13 | 90848930-92317491 | 91268794-91293729 | 5'amp | 2.89 | Not acceptable (2) |
| K-562 | NUP214 | chr9 | 132990802-133098912 | 133105930-133147163 | 5'amp | 2.57 | |
| K-562 | ABL1 | chr9 | 132579089-132752883 | 132538227-132601560 | 3'amp | 2.43 | |
| K-562 | CAMP | chr3 | 48239866-48241979 | 48235972-48294562 | 5'amp | 1.22 | level not matched |
| DU145.1 | SOX5 | chr12 | 23576498-24606647 | 23557809-23576870 | 5'amp | 1.14 | |
| DU145.1 | KRAS | chr12 | 25249446-25295121 | 25289615-25330834 | 3'amp | 1.10 | |
| DU145.1 | C14orf166 | chr14 | 51525942-51667191 | 51530172-51541520 | 5'amp | 1.04 | |
| DU145.1 | PPAP2C | chr19 | 232045-242435 | 64418-232080 | 5'amp | 1.03 | Not acceptable (4) |
| DU145.1 | RNF5 | chr6 | 32254149-32256545 | 32268003-32297149 | 5'amp | 0.89 | Not acceptable (2) |
| DU145.1 | UBE2L3 | chr22 | 20246510-20302877 | 20289615-20302254 | 5'amp | 0.89 | |
| DU145.1 | MYST1 | chr16 | 31036487-31050206 | 31065342-31081708 | 5'amp | 0.88 | Not acceptable (2) |
| DU145.1 | BTRC | chr10 | 103103814-103307058 | 103107408-103128976 | 5'amp | 0.86 | Not acceptable (3) |
| DU145.2 | SOX5 | chr12 | 23576498-26406647 | 23480427-23557809 | 5'amp | 0.99 | |
| DU145.2 | CCDC116 | chr22 | 20311639-20316169 | 20313694-20322692 | 5'amp | 0.97 | Not acceptable (2) |
| DU145.2 | SDF2L1 | chr22 | 20321095-20323141 | 20313694-20322692 | 5'amp | 0.97 | Not acceptable (2) |
| DU145.2 | UBE2L3 | chr22 | 20246510-20302877 | 20313694-20322692 | 5'amp | 0.97 | |
| DU145.2 | KRAS | chr12 | 25249446-25295121 | 25289615-25308034 | 3'amp | 0.96 | |
| DU145.2 | C14orf166 | chr14 | 51525942-51667191 | 51530172-51541520 | 5'amp | 0.76 | |

TABLE 7

The clinicopathological data and UBE2L3-KRAS expression across a panel of benign prostates, prostate cancer cell lines and tissues, and other tumors (UM and ULM cohort).

| Cohort | Sample | qPCR SYBR | qPCR Taqman | 5'RACE | RT-PCR | Sequencing | TMPRSS2-ERG (qPCR) | Age | Global Gleason Sum | pT | pN | pre-operation PSA |
|---|---|---|---|---|---|---|---|---|---|---|---|---|
| Benign prostate | NPP* | − | | | | | − | | | | | |
| | TXP** | − | − | | | | − | | | | | |
| | BPH1 | − | | | | | − | | | | | |
| | BPH2 | − | | | | | − | | | | | |
| | BPH3 | − | | | | | − | | | | | |
| | BPH4 | − | | | − | | − | | | | | |
| | BPH5 | − | − | | | | − | | | | | |
| | BPH6 | − | − | | | | − | | | | | |
| | BPH7 | − | | | − | | − | | | | | |
| | BPH8 | − | | | | | − | | | | | |
| | BPH9 | − | − | | − | | − | | | | | |
| | BPH10 | − | − | | | | − | | | | | |
| | PROSTATITIS | − | | | | | − | | | | | |
| Prostate cell lines | DU145 | + | + | + | + | + | − | | | | | |
| | DUCAP | − | − | | | | − | | | | | |
| | PC3 | − | | | | | − | | | | | |
| | RWPE | − | − | | | | − | | | | | |
| | LnCaP | − | | | | | − | | | | | |
| | VCAP | − | | | | | + | | | | | |
| Localized PCA (ULM) | PCA01 | + | | + | | | NA | 60 | 9 | T3a+ | 1 | 23.9 |
| | PCA02 | + | | − | | | NA | NA | NA | NA | NA | NA |
| | PCA03 | + | | + | | | + | 64 | 8 | T3b+ | 2 | 25.0 |
| | PCA04 | + | | | + | | + | 59 | 8 | T3a+ | 1 | 15.0 |
| | PCA05 | + | + | | | | − | 63 | 9 | T3a+ | 1 | 57.0 |
| | PCA06 | − | | | | | − | NA | 9 | NA | NA | NA |
| | PCA07 | − | | | | | + | 63 | 9 | T3a+ | 1 | 57.5 |
| | PCA08 | − | | | | | + | NA | 6 | NA | NA | NA |
| | PCA09 | − | | | | | − | 72 | 7 | T3b | 2 | 38.0 |
| | PCA10 | − | | | | | − | 72 | 8 | T3a | 1 | 16.5 |
| | PCA11 | − | | | | | + | 72 | 7 | T3a+ | 1 | 12.1 |
| | PCA12 | − | | | | | + | 61 | 8 | T4a | 2 | 26.2 |
| Localized PCA (UM) | PCA13 | + | + | | + | | + | 67 | NA | T4 | 0 | 0.4 |
| | PCA14 | + | + | | + | | − | 63 | 7 | T2b | 2 | 3.9 |
| | PCA15 | + | + | | + | + | NA | 74 | 7 | T2b | 0 | 6.9 |
| | PCA16 | + | | | − | | − | 78 | 8 | T3a | 0 | 5.0 |
| | PCA17 | + | | | | | − | 60 | 7 | T3a | 0 | 5.6 |
| | PCA18 | + | | | | | − | 81 | 7 | T2b | 2 | 4.8 |
| | PCA19 | + | | | | | − | 76 | 7 | T2b | 0 | 16.4 |
| | PCA20 | + | | | | | − | 72 | 7 | T2b | 2 | 7.5 |
| | PCA21 | + | + | | + | | − | 61 | 6 | T2b | 0 | 9.5 |
| | PCA22 | − | | | | | NA | 65 | 7 | T2a | 2 | 8.0 |
| | PCA23 | − | | | | | + | 57 | 7 | T2b | 0 | 8.4 |
| | PCA24 | − | | | | | − | 42 | 7 | T3a | 0 | 5.0 |
| | PCA25 | − | | | | | − | 65 | 7 | T3a | 0 | 3.5 |
| | PCA26 | − | | | | | − | 66 | 7 | T2b | 2 | 5.4 |
| | PCA27 | − | | | | | − | 63 | 9 | T3b | 1 | 44.6 |
| | PCA28 | − | | | | | − | 73 | 7 | T2b | 2 | 6.2 |
| | PCA29 | − | | | | | − | 67 | 6 | T2b | 0 | 3.9 |
| | PCA30 | − | | | | | − | 79 | 7 | T2b | 0 | 7.3 |
| | PCA31 | − | | | | | − | 73 | 8 | T3a | 0 | 12.4 |
| | PCA32 | − | | | | | NA | 79 | 8 | T2b | 2 | 0.9 |
| | PCA33 | − | | | − | | + | 55 | 7 | T3a | 0 | 5.0 |
| | PCA34 | − | | | − | | + | 62 | 7 | T2a | 2 | 10.2 |
| | PCA35 | − | | | − | | − | 63 | NA | T3b | 0 | 0.3 |
| | PCA36 | − | | | | | + | 59 | 7 | T3a | 0 | 14.9 |
| Metastatic PCA (UM)*** | MET01 | + | + | | | | + | 65 | NA | | | NA |
| | MET02 | + | | | + | | − | 65 | 6 | | | 35.0 |
| | MET03 | + | + | | | | − | 51 | NA | | | 486.0 |
| | MET04-1 | + | + | | | | − | 61 | 9 | | | NA |
| | MET04-2 | + | | | | | − | 61 | 9 | | | NA |
| | MET05-1 | + | | | | | + | 49 | 5 | | | NA |
| | MET06 | + | | | + | + | + | 54 | 9 | | | 6.4 |
| | MET07 | + | + | | + | | − | 67 | 9 | | | 7.5 |
| | MET08 | + | + | | | | − | 63 | NA | | | NA |
| | MET09 | + | | | | | − | 49 | 9 | | | NA |
| | MET10 | + | + | + | + | + | + | 65 | 6 | | | NA |
| | MET11 | − | − | | | | − | 74 | 10 | | | 32.0 |
| | MET05-2 | − | − | | | | + | 49 | 5 | | | NA |
| | MET12 | − | − | | | | + | 67 | NA | | | 232.0 |
| | MET13 | − | | | | | − | 71 | 7 | | | 10.4 |
| | MET14 | − | | | | | − | 72 | 8 | | | 65.0 |

TABLE 7-continued

The clinicopathological data and UBE2L3-KRAS expression across a panel of benign prostates, prostate cancer cell lines and tissues, and other tumors (UM and ULM cohort).

| Cohort | Sample | qPCR SYBR | qPCR Taqman | 5'RACE | RT-PCR | Sequencing | TMPRSS2-ERG (qPCR) | Age | Global Gleason Sum | pT | pN | pre-operation PSA |
|---|---|---|---|---|---|---|---|---|---|---|---|---|
| | MET15 | − | | | | | + | 61 | 8 | | | 29.0 |
| | MET05-3 | | | | − | | + | 49 | 5 | | | NA |
| | MET16 | − | | | − | | − | 75 | NA | | | NA |
| Melanoma cell lines | MM603 | − | − | | | | | | | | | |
| | SKMEL28 | − | | | | | | | | | | |
| | MMD14 | − | | | | | | | | | | |
| | MM576 | − | | | | | | | | | | |
| | SKMEL5 | − | | | | | | | | | | |
| | MM3M | − | | | | | | | | | | |
| | MM96L | − | | | | | | | | | | |
| | RM311 | − | | | | | | | | | | |
| | RM308 | − | | | | | | | | | | |
| Breast cancer tissues | BRE01 | − | − | | | | | | | | | |
| | BRE02 | − | − | | | | | | | | | |
| | BRE03 | − | | | | | | | | | | |

TABLE 8

UBE2L3-KRAS expression in 60 localized prostate cancer samples from Cornell cohort.

| Case | Age | Gleason Score# | pT | pN | pM | Pre-operative PSA | UBE2L3-KRAS Expression | Gleason Score* | FISH& | ERG Re-arrangement Status (FISH)$ | TMPRSS2-ERG Fusion Status (RT-PCR) | Comment |
|---|---|---|---|---|---|---|---|---|---|---|---|---|
| STID0000000025_T | 69 | 2 + 3 | 2c | 0 | x | 12.7 | + | 3 + 3 | | − | − | |
| STID0000000051_T | 66 | 3 + 4 | 3a | 0 | x | 6.5 | + | 4 + 3 | | + | − | |
| STID0000000057_T | 74 | 4 + 3 | 3b | 1 | x | 20.5 | + | 3 + 4 | | − | − | |
| STID0000000063_T | 72 | 2 + 4 | 2c | 0 | x | 8.7 | + | 4 + 3 | | − | − | |
| STID0000000097_T | 63 | 2 + 3 | 2c | 0 | x | 19.9 | + | 3 + 3 | | − | − | |
| STID0000000150_B_M | 67 | 2 + 3 | 2c | 0 | x | 15.9 | + | 3 + 4 | | + | − | |
| STID0000000423_C | 70 | 3 + 4 | 2c | 0 | x | 10.6 | + | 3 + 3 | | − | NA | |
| STID0000000424_B | 53 | 3 + 4 | 2c | 0 | x | 6 | + | 3 + 3 | | + | − | |
| STID0000000435_D | 69 | 3 + 4 | 3a | 0 | x | 4.9 | + | 3 + 4 | − | + | + | UBE-KRAS fusion transcript is different from the others |
| STID0000000505_D | 75 | 3 + 4 | 2c | 0 | x | 15.7 | + | 3 + 3 | − | − | − | |
| STID0000000540_C | 67 | 3 + 4 | 3a | 0 | x | 5.5 | + | 4 + 3 | | − | − | |
| STID0000000582_A | 61 | 3 + 3 | 2c | 0 | x | 3 | + | 3 + 3 | − | − | − | |
| STID0000001028_C | 55 | 3 + 4 | 2a | 0 | x | 5.8 | + | 3 + 3 | | − | − | |
| STID0000001032_B | 65 | 4 + 3 | 2c | 0 | x | 10.5 | + | 4 + 4 | | − | − | |
| STID0000001043_B | 59 | 3 + 3 | 2c | 0 | x | 4.9 | + | 3 + 3 | | + | − | |
| STID0000001765_A | 72 | 3 + 4 | 2a | 0 | x | 6 | + | 3 + 4 | | − | − | |
| STID0000001780_D | 60 | 3 + 4 | 2c | 0 | x | 4.5 | + | 3 + 4 | | − | + | |
| STID0000001783_B | 66 | 4 + 4 | 2c | 0 | x | 9.8 | + | 4 + 3 | | − | − | |
| STID0000000013_D | 68 | 3 + 3 | 2c | 1 | x | 10.5 | − | 3 + 3 | | + | + | |
| STID0000000020_T | 59 | 4 + 5 | 4 | 0 | x | 47.8 | − | 4 + 3 | | − | − | |
| STID0000000028_T | 69 | 3 + 4 | 2c | 0 | x | 7.5 | − | 3 + 3 | | + | + | |
| STID0000000034_T | 71 | 3 + 4 | 3b | 0 | x | 15.1 | − | 3 + 4 | | + | − | |
| STID0000000038_A | 53 | 3 + 4 | 2c | 0 | x | 8.1 | − | 3 + 4 | | − | − | |
| STID0000000041_J | 70 | 4 + 5 | 3b | 0 | x | 13.5 | − | 4 + 4 | | − | − | |
| STID0000000045_T | 68 | 2 + 3 | 2c | 0 | x | 12.5 | − | 3 + 3 | | + | + | |
| STID0000000054_T | 63 | 3 + 4 | 2c | 0 | x | 8.4 | − | 3 + 3 | | + | + | |
| STID0000000045_T | 68 | 2 + 3 | 2c | 0 | x | 12.5 | − | 3 + 3 | | + | + | |
| STID0000000054_T | 63 | 3 + 4 | 2c | 0 | x | 8.4 | − | 3 + 3 | | + | + | |
| STID0000000060_T | 64 | 3 + 4 | 2c | 0 | x | 19.3 | − | 3 + 4 | | + | + | |
| STID0000000069_T | 53 | 4 + 3 | 3a | 0 | x | 7.6 | − | 4 + 3 | | + | + | |
| STID0000000076_T | 64 | 4 + 5 | 3b | 0 | x | 8.5 | − | 4 + 5 | | − | − | |
| STID0000000088_T | 68 | 3 + 5 | 3b | 0 | x | 6.7 | − | 4 + 4 | | + | + | |
| STID0000000091_3 | 61 | 3 + 4 | 3a | 0 | x | 5.4 | − | 3 + 4 | | − | NA | |
| STID0000000099_T | 70 | 3 + 3 | 3a | 0 | x | 10.3 | − | 4 + 4 | | + | − | |
| STID0000000113_T | 60 | 4 + 5 | 3b | 0 | x | 7.9 | − | 4 + 3 | | − | − | |
| STID0000000127_T | 62 | 3 + 3 | 2a | 0 | x | 12.1 | − | 3 + 3 | | − | − | |
| STID0000000134_B | 64 | 3 + 2 | 2b | 0 | x | 10.2 | − | 3 + 3 | | − | − | |
| STID0000000136_T | 63 | 3 + 3 | 3a | 0 | x | 29.3 | − | 3 + 3 | | − | − | |
| STID0000000140_T | 63 | 3 + 4 | 3a/b | 0 | x | 26.9 | − | 4 + 3 | | + | + | |
| STID0000000145_C_M | 70 | 4 + 5 | 3a | 0 | x | 11.9 | − | 5 + 4 | | + | − | |

TABLE 8-continued

UBE2L3-KRAS expression in 60 localized prostate cancer samples from Cornell cohort.

| Case | Age | Gleason Score# pT | | pN | pM | Pre-operative PSA | UBE2L3-KRAS Expression | Gleason Score* | FISH& | ERG Re-arrangement Status (FISH)$ | TMPRSS2-ERG Fusion Status (RT-PCR) | Comment |
|---|---|---|---|---|---|---|---|---|---|---|---|---|
| STID0000000151_T | 61 | 2 + 3 | 2c | 0 | x | 3.4 | − | 3 + 3 | | − | − | |
| STID0000000415_B | 71 | 4 + 5 | 3a | 0 | x | 7.6 | − | 4 + 4 | | + | + | |
| STID0000000427_A | 69 | 4 + 3 | 2a | 0 | x | 5.1 | − | 3 + 4 | | − | − | |
| STID0000000428_A | 55 | 3 + 4 | 2c | 0 | x | 5.2 | − | 3 + 3 | | − | − | |
| STID0000000431_D | 64 | 3 + 3 | 2a | 0 | x | 2.4 | − | 4 + 3 | | + | + | |
| STID0000000432_C | 50 | 3 + 4 | 3a | 0 | x | 7 | − | 3 + 4 | | − | − | |
| STID0000000436_D | 42 | 4 + 3 | 2c | 0 | x | 9 | − | 3 + 4 | | − | NA | |
| STID0000000501_C | 60 | 3 + 4 | 3a | 0 | x | 3.4 | − | 3 + 3 | | − | − | |
| STID0000000522_D | 64 | 3 + 4 | 2c | 0 | x | 4.8 | − | 3 + 3 | | + | + | |
| STID0000000541_C | 70 | 3 + 4 | 2c | 0 | x | 5.6 | − | 3 + 3 | | − | − | |
| STID0000000560_D | 66 | 4 + 3 | 3a | 0 | x | 4.9 | − | 4 + 3 | | + | + | |
| STID0000000580_B | 56 | 3 + 4 | 2c | 0 | x | 3 | − | 3 + 4 | | + | + | |
| STID0000001027_C | 56 | 3 + 4 | 3a | 0 | x | 7.1 | − | 3 + 4 | | − | − | |
| STID0000001040_B | 60 | 3 + 4 | 2c | 0 | x | 5.3 | − | 4 + 3 | | − | − | |
| STID0000001060_B | 57 | 4 + 3 | 2c | 0 | x | 5.9 | − | 4 + 3 | | − | − | |
| STID0000001062_D | 57 | 3 + 4 | 2c | 0 | x | 5.2 | − | 3 + 3 | | − | − | |
| STID0000001701_A | 62 | 3 + 4 | 3a | 0 | x | 2.1 | − | 4 + 3 | | + | + | |
| STID0000001702_C | 65 | 3 + 4 | 3a | 0 | x | 4.6 | − | 3 + 3 | | − | − | |
| STID0000001703_B | 67 | 3 + 3 | 2c | 0 | x | 6 | − | 3 + 3 | | − | − | |
| STID0000001761_C | NA | NA | NA | NA | NA | NA | − | 3 + 4 | | − | − | |
| STID0000001763_B | 62 | 3 + 3 | 2c | 0 | x | 6.8 | − | 3 + 4 | | − | NA | |
| STID0000001781_C | 62 | 3 + 4 | 3a | 0 | x | 2.3 | − | 4 + 3 | | − | − | | patient specific Gleason Sum.
*focus specific Gleason Score.
&FISH was performed with KRAS split probes.

TABLE 9

The summary of UBE2L3-KRAS fusion status on prostate cancer tissues

| Cohort | Positive | Negative | Total | Percentage |
|---|---|---|---|---|
| PCA(UM) | 9 | 15 | 24 | 37.5% |
| PCA(ULM) | 5 | 7 | 12 | 41.7% |
| PCA(Cornell) | 18 | 42 | 60 | 30.0% |
| all PCA (3 cohort) | 32 | 64 | 96 | 33.3% |
| MET(UM) | 10 | 6 | 16 | 62.5% |
| Total (PCA + MET) | 42 | 70 | 112 | 37.5% |
| Melanoma cell lines | 0 | 9 | 9 | 0.0% |
| Breast cancer | 0 | 36 | 36 | 0.0% |

TABLE 10

Oligonucleotide primers used for RT-PCR, qPCR, 5' RLM-RACE and cloning.

| Gene | Refseq. | Primer | Type | Bases | Exon | Sequence(5' to 3') | application |
|---|---|---|---|---|---|---|---|
| SOX5 | NM_006940 | SOX5_S1 | Sense | 456 | Exon 3 | ACAGAGTGGCGAGTCCTTGTCT | RT-PCR |
| SOX5 | NM_006940 | SOX5_S2 | Sense | 1324 | Exon 10 | TCACCCACATCACCCACCTCTC | RT-PCR |
| C14orf166 | NM_016039 | C14orf166_S1 | Sense | 143 | Exon 1 | AAGTTGACGGCTCTCGACTACC | RT-PCR |
| C14orf166 | NM_016039 | C14orf166_S2 | Sense | 336 | Exon 3 | GTCCTTTCAAGATTCAAGATCG | RT-PCR |
| UBE2L3 | NM_003347 | UBE2L3_S1 | Sense | 53 | Exon 1 | GGGAAGGAGCAGCACCAAATCC | RT-PCR |
| UBE2L3 | NM_003347 | UBE2L3_S2 | Sense | 76 | Exon 1 | AGATGGCGGCCAGCAGGAGGCT | RT-PCR |
| UBE2L3 | NM_003347 | UBE2L3_S3 | Sense | 316 | Exon 3 | ACGAAAAGGGGCAGGTCTGTCT | RT-PCR |
| UBE2L3 | NM_003347 | UBE2L3_q1 | Sense | 345 | Exon 3 | ATTAGTGCCGAAAACTGGAAGC | RT-PCR, qPCR |
| UBE2L3 | NM_003347 | UBE2L3_R1 | Reverse | 363 | Exon 3 | GGTCGGTTTTGGTTGCTGGCTT | RT-PCR |

TABLE 10-continued

Oligonucleotide primers used for RT-PCR, qPCR, 5' RLM-RACE and cloning.

| Gene | Refseq. | Primer | Type | Bases | Exon | Sequence(5' to 3') | application |
|---|---|---|---|---|---|---|---|
| KRAS | NM_004985 | KRAS_S1 | Sense | 204 | Exon 2 | TAGTTGGAGCTGGTGGCGTAGG | RT-PCR |
| KRAS | NM_004985 | KRAS_R4 | Reverse | 204 | Exon 2 | CCTACGCCACCAGCTCCAACTA | RT-PCR |
| KRAS | NM_004985 | KRAS_R3 | Reverse | 228 | Exon 2 | AGCTGTATCGTCAAGGCACTCT | RT-PCR |
| KRAS | NM_004985 | KRAS_q2 | Reverse | 349 | Exon 3 | CTCCTCTTGACCTGCTGTGTCG | RT-PCR, qPCR |
| KRAS | NM_004985 | KRAS_R7 | Reverse | 540 | Exon 4 | GTGTCTACTGTTCTAGAAGGCA | RT-PCR |
| KRAS | NM_004985 | KRAS_R2 | Reverse | 1594 | Exon 5 | AGAGCAGTCTGACACAGGGAGA | RT-PCR |
| KRAS | NM_004985 | KRAS_R1 | Reverse | 1893 | Exon 5 | GTCAGCAGGACCACCACAGAGT | RT-PCR |
| KRAS | NM_004985 | KRAS_R6 | Reverse | 3313 | Exon 5 | ACTGGCATCTGGTAGGCACTCA | RT-PCR |
| GAPDH | NM_002046 | GAPDH_S1 | Sense | 822 | Exon 8 | GTCAGTGGTGGACCTGACCT | RT-PCR |
| GAPDH | NM_002046 | GAPDH_R1 | Reverse | 1014 | Exon 8 | TGAGCTTGACAAAGTGGTCG | RT-PCR |
| GAPDH | NM_002046 | GAPDH_S2 | Sense | 556 | Exon 7 | TGCACCACCAACTGCTTAGC | qPCR |
| GAPDH | NM_002046 | GAPDH_R2 | Reverse | 622 | Exon 1 | GGCATGGACTGTGGTCATGAG | qPCR |
| UBE2L3 | NM_003347 | N-FLAG | Sense | 81 | Exon 1 | TCCACCATGGATTACAAGGATGACGACGATAA GGCGGCCAGCAGGAGGCTGATGAAGGAGCTTG | Cloning |
| UBE2L3 | NM_003347 | wild type | Sense | 78 | Exon 1 | TCCACCATGGCGGCCAGCAGGAGGCTGATGAA GGAGCTTG | Cloning |
| KRAS4B | NM_004985 | wild type 4B | Reverse | 717 | Exon 5 | TTACATAATTACACACTTTGTCTTTGACTTCT | Cloning |
| KRAS4A | NM_033360 | wild type 4A | Reverse | 720 | Exon 5 | TTACATTATAATGCATTTTTTAATTTTCACAC | Cloning |

TABLE 11

Summary of the KRAS rearrangement and UBE2L3-KRAS fusion status by FISH analysis of a series of prostate cancer tissue microarrays. Table shows the number of positive cases divided by total number of evaluable cases.

| Tissue type | KRAS rearrangement | UBE2L3-KRAS fusion |
|---|---|---|
| Localized PCA | 0/78 (0%) | 0/67 (0%) |
| Metastastic PCA | 0/29 (0%) | 0/18 (0%) |

All publications, patents, patent applications and accession numbers mentioned in the above specification are herein incorporated by reference in their entirety. Although the invention has been described in connection with specific embodiments, it should be understood that the invention as claimed should not be unduly limited to such specific embodiments. Indeed, various modifications and variations of the described compositions and methods of the invention will be apparent to those of ordinary skill in the art and are intended to be within the scope of the following claims.

We claim:

1. A method for detecting a RAF gene fusion in a biological sample, the method comprising:
   a) forming a hybridized structure comprising:
      i) a nucleic acid comprising a RAF gene fusion comprising a 5' component joined at a fusion junction to a 3' component, said 3' component comprising a rapidly accelerated fibrosarcoma (RAF) kinase domain and said 5' component comprising a transcriptional regulatory region from an androgen regulated gene; and
      ii) a detectably labeled probe specifically hybridized to said nucleic acid and spanning said fusion junction; and
   b) detecting the presence of the RAF gene fusion in the biological sample by detecting said hybridized structure in said biological sample.

2. The method of claim 1 wherein the transcriptional regulatory region comprises a promoter region.

3. The method of claim 1 wherein the transcriptional regulatory region comprises an androgen response element.

4. The method of claim 1 comprising detecting wherein said nucleic acid comprising said RAF gene fusion comprises a chromosomal rearrangement of genomic DNA.

5. The method of claim 1 wherein said nucleic acid comprising said RAF gene fusion is a chimeric mRNA transcript.

6. The method of claim 1, wherein the biological sample is selected from the group consisting of tissue, blood, plasma, serum, urine, urine supernatant, urine cell pellet, semen, prostatic secretions, and prostate cells.

7. The method of claim 1 wherein said nucleic acid comprising said RAF gene fusion is an amplification product.

8. The method of claim 1 wherein the biological sample is from a patient having or suspected of having prostate cancer.

9. The method of claim 1 further comprising treating a patient that is the source of the biological sample.

10. A method for detecting a RAF gene fusion in a biological sample, the method comprising:
    a) forming a hybridized structure comprising:
       i) a nucleic acid comprising a RAF gene fusion comprising a 5' component and a 3' component, said 3' component comprising a rapidly accelerated fibrosarcoma (RAF) kinase domain and said 5' component comprising a transcriptional regulatory region from an androgen regulated gene; and
       ii) a first detectably labeled nucleic acid probe specifically hybridized to said 5' component and a second detectably labeled nucleic acid probe specifically hybridized to said 3' component; and
    b) detecting the presence of the RAF gene fusion in the biological sample by detecting said hybridized structure in said biological sample.

11. The method of claim 10 wherein the transcriptional regulatory region comprises a promoter region.

12. The method of claim 10 wherein the transcriptional regulatory region comprises an androgen response element.

13. The method of claim 10 wherein said nucleic acid comprising said RAF gene fusion comprises a chromosomal rearrangement of genomic DNA.

14. The method of claim 10 wherein said nucleic acid comprising said RAF gene fusion is a chimeric mRNA transcript.

15. The method of claim 10, wherein the biological sample is selected from the group consisting of tissue, blood, plasma, serum, urine, urine supernatant, urine cell pellet, semen, prostatic secretions, and prostate cells.

16. The method of claim 10 wherein said nucleic acid comprising said RAF gene fusion is an amplification product.

17. The method of claim 10 wherein the biological sample is from a patient having or suspected of having prostate cancer.

18. The method of claim 10 further comprising treating a patient that is the source of the biological sample.

19. The method of claim 10 wherein detecting said hybridized structure in said biological sample comprises a fluorescence in situ hybridization method.

20. A method for detecting a RAF gene fusion in a biological sample, the method comprising:
    a) forming a hybridized structure comprising:
       i) a nucleic acid comprising a gene fusion comprising a 5' component and a 3' component, said 3' component comprising a rapidly accelerated fibrosarcoma (RAF) kinase domain and said 5' component comprising a transcriptional regulatory region from an androgen regulated gene; and
       ii) a first amplification primer specifically hybridized to said 5' component and a second amplification primer specifically hybridized to said 3' component;
    b) amplifying a portion of the nucleic acid using a nucleic acid amplification reaction to produce an amplification product; and
    c) detecting the presence of the RAF gene fusion in the biological sample by detecting the gene fusion amplification product.

21. The method of claim 20 wherein the transcriptional regulatory region comprises a promoter region.

22. The method of claim 20 wherein the transcriptional regulatory region comprises an androgen response element.

23. The method of claim 20, wherein the biological sample is selected from the group consisting of tissue, blood, plasma, serum, urine, urine supernatant, urine cell pellet, semen, prostatic secretions, and prostate cells.

24. The method of claim 20 wherein the biological sample is from a patient having or suspected of having prostate cancer.

25. The method of claim 20 further comprising treating a patient that is the source of the biological sample.

26. The method of claim 20 wherein detecting the gene fusion amplification product comprises use of a real-time amplification method, a labeled oligonucleotide probe, or an intercalating dye.

* * * * *

UNITED STATES PATENT AND TRADEMARK OFFICE
CERTIFICATE OF CORRECTION

| | |
|---|---|
| PATENT NO. | : 9,926,602 B2 |
| APPLICATION NO. | : 14/302199 |
| DATED | : March 27, 2018 |
| INVENTOR(S) | : Arul M. Chinnaiyan and Xiaosong Wang |

Page 1 of 1

It is certified that error appears in the above-identified patent and that said Letters Patent is hereby corrected as shown below:

On the Title Page

Item (71), the Applicant should read:
Applicant: THE REGENTS OF THE UNIVERSITY OF MICHIGAN, Ann Arbor, MI (US)

In the Claims

Column 87, Claim 4, Line 36 should read:
"The method of claim 1 wherein said nucleic acid comprising said RAF gene fusion comprises a chromosomal rearrangement of genomic DNA."

Signed and Sealed this
First Day of May, 2018

Andrei Iancu
*Director of the United States Patent and Trademark Office*

SEQUENCE LISTING

```
<160> NUMBER OF SEQ ID NOS: 82

<210> SEQ ID NO 1
<211> LENGTH: 19
<212> TYPE: DNA
<213> ORGANISM: Artificial Sequence
<220> FEATURE:
<223> OTHER INFORMATION: Synthetic

<400> SEQUENCE: 1
ccaccgaaga tcacattta                                                  19

<210> SEQ ID NO 2
<211> LENGTH: 19
<212> TYPE: DNA
<213> ORGANISM: Artificial Sequence
<220> FEATURE:
<223> OTHER INFORMATION: Synthetic
```

```
<400> SEQUENCE: 2
gaagttatgg aattccttt                                              19

<210> SEQ ID NO 3
<211> LENGTH: 19
<212> TYPE: DNA
<213> ORGANISM: Artificial Sequence
<220> FEATURE:
<223> OTHER INFORMATION: Synthetic

<400> SEQUENCE: 3
ccgaccaagg cctgctgaa                                              19

<210> SEQ ID NO 4
<211> LENGTH: 9
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: n is a or t

<400> SEQUENCE: 4 acagngaaa                                                          9

<210> SEQ ID NO 5
<211> LENGTH: 9
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: n is a or t

<400> SEQUENCE: 5 acagngaaa                                                          9

<210> SEQ ID NO 6
<211> LENGTH: 18
<212> TYPE: DNA
<213> ORGANISM: Artificial Sequence
<220> FEATURE:
<223> OTHER INFORMATION: Synthetic

<400> SEQUENCE: 6
agccgcgcgc ctcggcca                                               18

<210> SEQ ID NO 7
<211> LENGTH: 24
<212> TYPE: DNA
<213> ORGANISM: Artificial Sequence
<220> FEATURE:
<223> OTHER INFORMATION: Synthetic

<400> SEQUENCE: 7
atcaggaatc tcccaatcat cact                                        24

<210> SEQ ID NO 8
<211> LENGTH: 23
<212> TYPE: DNA
<213> ORGANISM: Artificial Sequence
<220> FEATURE:
<223> OTHER INFORMATION: Synthetic
```

```
<400> SEQUENCE: 8
gtaccagccc cacccctcta tcc                                              23

<210> SEQ ID NO 9
<211> LENGTH: 24
<212> TYPE: DNA
<213> ORGANISM: Artificial Sequence
<220> FEATURE:
<223> OTHER INFORMATION: Synthetic

<400> SEQUENCE: 9
tcagtggaca ggaaacgcac cata                                             24

<210> SEQ ID NO 10
<211> LENGTH: 24
<212> TYPE: DNA
<213> ORGANISM: Artificial Sequence
<220> FEATURE:
<223> OTHER INFORMATION: Synthetic

<400> SEQUENCE: 10
gccccaaatt ctcaccagtc cgtc                                             24

<210> SEQ ID NO 11
<211> LENGTH: 22
<212> TYPE: DNA
<213> ORGANISM: Artificial Sequence
<220> FEATURE:
<223> OTHER INFORMATION: Synthetic

<400> SEQUENCE: 11
tcagtggaca ggaaacgcac ca                                               22

<210> SEQ ID NO 12
<211> LENGTH: 22
<212> TYPE: DNA
<213> ORGANISM: Artificial Sequence
<220> FEATURE:
<223> OTHER INFORMATION: Synthetic

<400> SEQUENCE: 12
atgaaacact tggtagacgg ga                                               22

<210> SEQ ID NO 13
<211> LENGTH: 22
<212> TYPE: DNA
<213> ORGANISM: Artificial Sequence
<220> FEATURE:
<223> OTHER INFORMATION: Synthetic

<400> SEQUENCE: 13
tcagtggaca ggaaacgcac ca                                               22

<210> SEQ ID NO 14
<211> LENGTH: 24
<212> TYPE: DNA
<213> ORGANISM: Artificial Sequence
<220> FEATURE:
<223> OTHER INFORMATION: Synthetic

<400> SEQUENCE: 14
aacatataga ggccctattg gaca                                             24
```

```
<210> SEQ ID NO 15
<211> LENGTH: 23
<212> TYPE: DNA
<213> ORGANISM: Artificial Sequence
<220> FEATURE:
<223> OTHER INFORMATION: Synthetic

<400> SEQUENCE: 15
agaagatgta acggtatcca ttg                                               23

<210> SEQ ID NO 16
<211> LENGTH: 25
<212> TYPE: DNA
<213> ORGANISM: Artificial Sequence
<220> FEATURE:
<223> OTHER INFORMATION: Synthetic

<400> SEQUENCE: 16
ggagttacag tccgagacag tctaa                                             25

<210> SEQ ID NO 17
<211> LENGTH: 25
<212> TYPE: DNA
<213> ORGANISM: Artificial Sequence
<220> FEATURE:
<223> OTHER INFORMATION: Synthetic

<400> SEQUENCE: 17
cagtaagcca ggaaatatca gtgtc                                             25

<210> SEQ ID NO 18
<211> LENGTH: 25
<212> TYPE: DNA
<213> ORGANISM: Artificial Sequence
<220> FEATURE:
<223> OTHER INFORMATION: Synthetic

<400> SEQUENCE: 18
agcgttgtag tacagaagtt ccact                                             25

<210> SEQ ID NO 19
<211> LENGTH: 23
<212> TYPE: DNA
<213> ORGANISM: Artificial Sequence
<220> FEATURE:
<223> OTHER INFORMATION: Synthetic

<400> SEQUENCE: 19
agatgttagg gcagtctctg cta                                               23

<210> SEQ ID NO 20
<211> LENGTH: 26
<212> TYPE: DNA
<213> ORGANISM: Artificial Sequence
<220> FEATURE:
<223> OTHER INFORMATION: Synthetic

<400> SEQUENCE: 20
tgtgcatata aacacaatag aacctg                                            26

<210> SEQ ID NO 21
<211> LENGTH: 21
<212> TYPE: DNA
<213> ORGANISM: Artificial Sequence
<220> FEATURE:
<223> OTHER INFORMATION: Synthetic
```

<400> SEQUENCE: 21
ttcgattcct gtcttctgag g                                              21

<210> SEQ ID NO 22
<211> LENGTH: 23
<212> TYPE: DNA
<213> ORGANISM: Artificial Sequence
<220> FEATURE:
<223> OTHER INFORMATION: Synthetic

<400> SEQUENCE: 22
aaaacacttg gtagacggga ctc                                            23

<210> SEQ ID NO 23
<211> LENGTH: 24
<212> TYPE: DNA
<213> ORGANISM: Artificial Sequence
<220> FEATURE:
<223> OTHER INFORMATION: Synthetic

<400> SEQUENCE: 23
cttgtaactg ctgaggtgta ggtg                                           24

<210> SEQ ID NO 24
<211> LENGTH: 25
<212> TYPE: DNA
<213> ORGANISM: Artificial Sequence
<220> FEATURE:
<223> OTHER INFORMATION: Synthetic

<400> SEQUENCE: 24
ttgtatcacc atctccatat cattg                                          25

<210> SEQ ID NO 25
<211> LENGTH: 21
<212> TYPE: DNA
<213> ORGANISM: Artificial Sequence
<220> FEATURE:
<223> OTHER INFORMATION: Synthetic

<400> SEQUENCE: 25
ggatgattga cttggcgtgt a                                              21

<210> SEQ ID NO 26
<211> LENGTH: 24
<212> TYPE: DNA
<213> ORGANISM: Artificial Sequence
<220> FEATURE:
<223> OTHER INFORMATION: Synthetic

<400> SEQUENCE: 26
ctacagtgaa atctcgatgg agtg                                           24

<210> SEQ ID NO 27
<211> LENGTH: 23
<212> TYPE: DNA
<213> ORGANISM: Artificial Sequence
<220> FEATURE:
<223> OTHER INFORMATION: Synthetic

<400> SEQUENCE: 27
tcatacagaa caattccaaa tgc                                            23

<210> SEQ ID NO 28
<211> LENGTH: 21
<212> TYPE: DNA
<213> ORGANISM: Artificial Sequence
<220> FEATURE:
<223> OTHER INFORMATION: Synthetic

<400> SEQUENCE: 28
cgaggatacc tgtctccaga t                                              21

<210> SEQ ID NO 29
<211> LENGTH: 21
<212> TYPE: DNA
<213> ORGANISM: Artificial Sequence
<220> FEATURE:
<223> OTHER INFORMATION: Synthetic

<400> SEQUENCE: 29
gatgcactgc ggtgaatttt t                                              21

<210> SEQ ID NO 30
<211> LENGTH: 25
<212> TYPE: DNA
<213> ORGANISM: Artificial Sequence
<220> FEATURE:
<223> OTHER INFORMATION: Synthetic

<400> SEQUENCE: 30
agtgagagag ttcaggagag tagca                                          25

<210> SEQ ID NO 31
<211> LENGTH: 27
<212> TYPE: DNA
<213> ORGANISM: Artificial Sequence
<220> FEATURE:
<223> OTHER INFORMATION: Synthetic

<400> SEQUENCE: 31
aagtataaat tttagtttgg ggaaaaa                                        27

<210> SEQ ID NO 32
<211> LENGTH: 21
<212> TYPE: DNA
<213> ORGANISM: Artificial Sequence
<220> FEATURE:
<223> OTHER INFORMATION: Synthetic

<400> SEQUENCE: 32
catgagcact gtagcaccaa a                                              21

<210> SEQ ID NO 33
<211> LENGTH: 21
<212> TYPE: DNA
<213> ORGANISM: Artificial Sequence
<220> FEATURE:
<223> OTHER INFORMATION: Synthetic

<400> SEQUENCE: 33
agcagctgta gggaagtagc c                                              21

<210> SEQ ID NO 34
<211> LENGTH: 21
<212> TYPE: DNA
<213> ORGANISM: Artificial Sequence
<220> FEATURE:
<223> OTHER INFORMATION: Synthetic

<400> SEQUENCE: 34
gtactaccca gcaggcactc a                                              21

<210> SEQ ID NO 35
<211> LENGTH: 21
<212> TYPE: DNA
<213> ORGANISM: Artificial Sequence
<220> FEATURE:
<223> OTHER INFORMATION: Synthetic

<400> SEQUENCE: 35
ctgggactcc actatcacca a                                              21

<210> SEQ ID NO 36
<211> LENGTH: 21
<212> TYPE: DNA
<213> ORGANISM: Artificial Sequence
<220> FEATURE:
<223> OTHER INFORMATION: Synthetic

<400> SEQUENCE: 36
atggagcaca tacagggagc t                                              21

<210> SEQ ID NO 37
<211> LENGTH: 23
<212> TYPE: DNA
<213> ORGANISM: Artificial Sequence
<220> FEATURE:
<223> OTHER INFORMATION: Synthetic

<400> SEQUENCE: 37
ttaaatacaa acccattctt tgg                                            23

<210> SEQ ID NO 38
<211> LENGTH: 20
<212> TYPE: DNA
<213> ORGANISM: Artificial Sequence
<220> FEATURE:
<223> OTHER INFORMATION: Synthetic

<400> SEQUENCE: 38
atgacggcct ctccggatta                                                20

<210> SEQ ID NO 39
<211> LENGTH: 20
<212> TYPE: DNA
<213> ORGANISM: Artificial Sequence
<220> FEATURE:
<223> OTHER INFORMATION: Synthetic

<400> SEQUENCE: 39
ctagaagaca ggcagcctcg                                                20

<210> SEQ ID NO 40
<211> LENGTH: 14
<212> TYPE: DNA
<213> ORGANISM: Artificial Sequence
<220> FEATURE:
<223> OTHER INFORMATION: Synthetic

<400> SEQUENCE: 40
cagcaaccaa aacc                                                      14

```
<210> SEQ ID NO 41
<211> LENGTH: 22
<212> TYPE: DNA
<213> ORGANISM: Artificial Sequence
<220> FEATURE:
<223> OTHER INFORMATION: Synthetic

<400> SEQUENCE: 41
acagagtggc gagtccttgt ct                                            22

<210> SEQ ID NO 42
<211> LENGTH: 22
<212> TYPE: DNA
<213> ORGANISM: Artificial Sequence
<220> FEATURE:
<223> OTHER INFORMATION: Synthetic

<400> SEQUENCE: 42
tcacccacat cacccacctc tc                                            22

<210> SEQ ID NO 43
<211> LENGTH: 22
<212> TYPE: DNA
<213> ORGANISM: Artificial Sequence
<220> FEATURE:
<223> OTHER INFORMATION: Synthetic

<400> SEQUENCE: 43
aagttgacgg ctctcgacta cc                                            22

<210> SEQ ID NO 44
<211> LENGTH: 22
<212> TYPE: DNA
<213> ORGANISM: Artificial Sequence
<220> FEATURE:
<223> OTHER INFORMATION: Synthetic

<400> SEQUENCE: 44
gtcctttcaa gattcaagat cg                                            22

<210> SEQ ID NO 45
<211> LENGTH: 22
<212> TYPE: DNA
<213> ORGANISM: Artificial Sequence
<220> FEATURE:
<223> OTHER INFORMATION: Synthetic

<400> SEQUENCE: 45
gggaaggagc agcaccaaat cc                                            22

<210> SEQ ID NO 46
<211> LENGTH: 22
<212> TYPE: DNA
<213> ORGANISM: Artificial Sequence
<220> FEATURE:
<223> OTHER INFORMATION: Synthetic

<400> SEQUENCE: 46
agatggcggc cagcaggagg ct                                            22

<210> SEQ ID NO 47
<211> LENGTH: 22
<212> TYPE: DNA
<213> ORGANISM: Artificial Sequence
<220> FEATURE:
<223> OTHER INFORMATION: Synthetic
```

```
<400> SEQUENCE: 47
acgaaaaggg gcaggtctgt ct                                              22

<210> SEQ ID NO 48
<211> LENGTH: 22
<212> TYPE: DNA
<213> ORGANISM: Artificial Sequence
<220> FEATURE:
<223> OTHER INFORMATION: Synthetic

<400> SEQUENCE: 48
attagtgccg aaaactggaa gc                                              22

<210> SEQ ID NO 49
<211> LENGTH: 22
<212> TYPE: DNA
<213> ORGANISM: Artificial Sequence
<220> FEATURE:
<223> OTHER INFORMATION: Synthetic

<400> SEQUENCE: 49
ggtcggtttt ggttgctggc tt                                              22

<210> SEQ ID NO 50
<211> LENGTH: 22
<212> TYPE: DNA
<213> ORGANISM: Artificial Sequence
<220> FEATURE:
<223> OTHER INFORMATION: Synthetic

<400> SEQUENCE: 50
tagttggagc tggtggcgta gg                                              22

<210> SEQ ID NO 51
<211> LENGTH: 22
<212> TYPE: DNA
<213> ORGANISM: Artificial Sequence
<220> FEATURE:
<223> OTHER INFORMATION: Synthetic

<400> SEQUENCE: 51
cctacgccac cagctccaac ta                                              22

<210> SEQ ID NO 52
<211> LENGTH: 22
<212> TYPE: DNA
<213> ORGANISM: Artificial Sequence
<220> FEATURE:
<223> OTHER INFORMATION: Synthetic

<400> SEQUENCE: 52
agctgtatcg tcaaggcact ct                                              22

<210> SEQ ID NO 53
<211> LENGTH: 22
<212> TYPE: DNA
<213> ORGANISM: Artificial Sequence
<220> FEATURE:
<223> OTHER INFORMATION: Synthetic

<400> SEQUENCE: 53
ctcctcttga cctgctgtgt cg                                              22
```

```
<210> SEQ ID NO 54
<211> LENGTH: 22
<212> TYPE: DNA
<213> ORGANISM: Artificial Sequence
<220> FEATURE:
<223> OTHER INFORMATION: Synthetic

<400> SEQUENCE: 54
gtgtctactg ttctagaagg ca                                              22

<210> SEQ ID NO 55
<211> LENGTH: 22
<212> TYPE: DNA
<213> ORGANISM: Artificial Sequence
<220> FEATURE:
<223> OTHER INFORMATION: Synthetic

<400> SEQUENCE: 55
agagcagtct gacacaggga ga                                              22

<210> SEQ ID NO 56
<211> LENGTH: 22
<212> TYPE: DNA
<213> ORGANISM: Artificial Sequence
<220> FEATURE:
<223> OTHER INFORMATION: Synthetic

<400> SEQUENCE: 56
gtcagcagga ccaccacaga gt                                              22

<210> SEQ ID NO 57
<211> LENGTH: 22
<212> TYPE: DNA
<213> ORGANISM: Artificial Sequence
<220> FEATURE:
<223> OTHER INFORMATION: Synthetic

<400> SEQUENCE: 57
actggcatct ggtaggcact ca                                              22

<210> SEQ ID NO 58
<211> LENGTH: 20
<212> TYPE: DNA
<213> ORGANISM: Artificial Sequence
<220> FEATURE:
<223> OTHER INFORMATION: Synthetic

<400> SEQUENCE: 58
gtcagtggtg gacctgacct                                                 20

<210> SEQ ID NO 59
<211> LENGTH: 20
<212> TYPE: DNA
<213> ORGANISM: Artificial Sequence
<220> FEATURE:
<223> OTHER INFORMATION: Synthetic

<400> SEQUENCE: 59
tgagcttgac aaagtggtcg                                                 20

<210> SEQ ID NO 60
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 60
tgcaccacca actgcttagc                                              20

<210> SEQ ID NO 61
<211> LENGTH: 21
<212> TYPE: DNA
<213> ORGANISM: Artificial Sequence
<220> FEATURE:
<223> OTHER INFORMATION: Synthetic

<400> SEQUENCE: 61
ggcatggact gtggtcatga g                                            21

<210> SEQ ID NO 62
<211> LENGTH: 64
<212> TYPE: DNA
<213> ORGANISM: Artificial Sequence
<220> FEATURE:
<223> OTHER INFORMATION: Synthetic

<400> SEQUENCE: 62
tccaccatgg attacaagga tgacgacgat aaggcggcca gcaggaggct gatgaaggag  60
cttg                                                               64

<210> SEQ ID NO 63
<211> LENGTH: 40
<212> TYPE: DNA
<213> ORGANISM: Artificial Sequence
<220> FEATURE:
<223> OTHER INFORMATION: Synthetic

<400> SEQUENCE: 63
tccaccatgg cggccagcag gaggctgatg aaggagcttg                        40

<210> SEQ ID NO 64
<211> LENGTH: 32
<212> TYPE: DNA
<213> ORGANISM: Artificial Sequence
<220> FEATURE:
<223> OTHER INFORMATION: Synthetic

<400> SEQUENCE: 64
ttacataatt acacactttg tctttgactt ct                                32

<210> SEQ ID NO 65
<211> LENGTH: 32
<212> TYPE: DNA
<213> ORGANISM: Artificial Sequence
<220> FEATURE:
<223> OTHER INFORMATION: Synthetic

<400> SEQUENCE: 65
ttacattata atgcattttt taattttcac ac                                32

<210> SEQ ID NO 66
<211> LENGTH: 13
<212> TYPE: DNA
<213> ORGANISM: Artificial Sequence
<220> FEATURE:
<223> OTHER INFORMATION: Synthetic

<400> SEQUENCE: 66
gcgcctcggc cag                                                     13
```

<210> SEQ ID NO 67
<211> LENGTH: 14
<212> TYPE: DNA
<213> ORGANISM: Artificial Sequence
<220> FEATURE:
<223> OTHER INFORMATION: Synthetic

<400> SEQUENCE: 67
gccccaaatt ctca                                                      14

<210> SEQ ID NO 68
<211> LENGTH: 13
<212> TYPE: DNA
<213> ORGANISM: Artificial Sequence
<220> FEATURE:
<223> OTHER INFORMATION: Synthetic

<400> SEQUENCE: 68
cgtactatcc cag                                                       13

<210> SEQ ID NO 69
<211> LENGTH: 14
<212> TYPE: DNA
<213> ORGANISM: Artificial Sequence
<220> FEATURE:
<223> OTHER INFORMATION: Synthetic

<400> SEQUENCE: 69
attgtttcca aatt                                                      14

<210> SEQ ID NO 70
<211> LENGTH: 40
<212> TYPE: DNA
<213> ORGANISM: Artificial Sequence
<220> FEATURE:
<223> OTHER INFORMATION: Synthetic

<400> SEQUENCE: 70
cacgcgctgg ctccgggtga cagccgcgcg cctcggccag                          40

<210> SEQ ID NO 71
<211> LENGTH: 40
<212> TYPE: DNA
<213> ORGANISM: Artificial Sequence
<220> FEATURE:
<223> OTHER INFORMATION: Synthetic

<400> SEQUENCE: 71
ctgcacgcgc tggctccggg tgacagccgc gcgcctcggc                          40

<210> SEQ ID NO 72
<211> LENGTH: 40
<212> TYPE: DNA
<213> ORGANISM: Artificial Sequence
<220> FEATURE:
<223> OTHER INFORMATION: Synthetic

<400> SEQUENCE: 72
cggaaccagc ctgcacgcgc tggctccggg tgacagccgc                          40

<210> SEQ ID NO 73
<211> LENGTH: 40
<212> TYPE: DNA
<213> ORGANISM: Artificial Sequence
<220> FEATURE:
<223> OTHER INFORMATION: Synthetic -continued

<400> SEQUENCE: 73
tgggagctaa tgaggatcgg tctcgttgcc caaattgatt                          40

<210> SEQ ID NO 74
<211> LENGTH: 40
<212> TYPE: DNA
<213> ORGANISM: Artificial Sequence
<220> FEATURE:
<223> OTHER INFORMATION: Synthetic

<400> SEQUENCE: 74
ggagctgatg aggatcggtc tcgttgccca aattgatttc                          40

<210> SEQ ID NO 75
<211> LENGTH: 40
<212> TYPE: DNA
<213> ORGANISM: Artificial Sequence
<220> FEATURE:
<223> OTHER INFORMATION: Synthetic

<400> SEQUENCE: 75
tcggaagggc tgtggaattg aatggatttt tgaaggagac                          40

<210> SEQ ID NO 76
<211> LENGTH: 40
<212> TYPE: DNA
<213> ORGANISM: Artificial Sequence
<220> FEATURE:
<223> OTHER INFORMATION: Synthetic

<400> SEQUENCE: 76
ggattttgaa ggagacggac tggtgagaat ttggggcctg                          40

<210> SEQ ID NO 77
<211> LENGTH: 21
<212> TYPE: DNA
<213> ORGANISM: Artificial Sequence
<220> FEATURE:
<223> OTHER INFORMATION: Synthetic

<400> SEQUENCE: 77
accgaccaag gcctgctgaa a                                              21

<210> SEQ ID NO 78
<211> LENGTH: 295
<212> TYPE: PRT
<213> ORGANISM: Artificial Sequence
<220> FEATURE:
<223> OTHER INFORMATION: Synthetic

<400> SEQUENCE: 78

Met Ala Ala Ser Arg Arg Leu Met Lys Glu Leu Glu Glu Ile Arg Lys
1               5                   10                  15

Cys Gly Met Lys Asn Phe Arg Asn Ile Gln Val Asp Glu Ala Asn Leu
            20                  25                  30

Leu Thr Trp Gln Gly Leu Ile Val Pro Asp Asn Pro Pro Tyr Asp Lys
        35                  40                  45

Gly Ala Phe Arg Ile Glu Ile Asn Phe Pro Ala Glu Tyr Pro Phe Lys
    50                  55                  60

Pro Pro Lys Ile Thr Phe Lys Thr Lys Ile Tyr His Pro Asn Ile Asp
65                  70                  75                  80

Glu Lys Gly Gln Val Cys Leu Pro Val Ile Ser Ala Glu Asn Trp Lys
                85                  90                  95

```
Pro Ala Thr Lys Thr Asp Gln Gly Leu Leu Lys Met Thr Glu Tyr Lys
            100                 105                 110

Leu Val Val Gly Ala Gly Val Gly Lys Ser Ala Leu Thr Ile
        115                 120                 125

Gln Leu Ile Gln Asn His Phe Val Asp Glu Tyr Asp Pro Thr Ile Glu
    130                 135                 140

Asp Ser Tyr Arg Lys Gln Val Val Ile Asp Gly Glu Thr Cys Leu Leu
145                 150                 155                 160

Asp Ile Leu Asp Thr Ala Gly Gln Glu Glu Tyr Ser Ala Met Arg Asp
                165                 170                 175

Gln Tyr Met Arg Thr Gly Glu Gly Phe Leu Cys Val Phe Ala Ile Asn
            180                 185                 190

Asn Thr Lys Ser Phe Glu Asp Ile His His Tyr Arg Glu Gln Ile Lys
        195                 200                 205

Arg Val Lys Asp Ser Glu Asp Val Pro Met Val Leu Val Gly Asn Lys
    210                 215                 220

Cys Asp Leu Pro Ser Arg Thr Val Asp Thr Lys Gln Ala Gln Asp Leu
225                 230                 235                 240

Ala Arg Ser Tyr Gly Ile Pro Phe Ile Glu Thr Ser Ala Lys Thr Arg
                245                 250                 255

Gln Gly Val Asp Asp Ala Phe Tyr Thr Leu Val Arg Glu Ile Arg Lys
            260                 265                 270

His Lys Glu Lys Met Ser Lys Asp Gly Lys Lys Lys Lys Lys Lys Ser
        275                 280                 285

Lys Thr Lys Cys Val Ile Met
    290                 295

<210> SEQ ID NO 79
<211> LENGTH: 9
<212> TYPE: PRT
<213> ORGANISM: Artificial Sequence
<220> FEATURE:
<223> OTHER INFORMATION: Synthetic

<400> SEQUENCE: 79

Ile Tyr His Pro Asn Ile Asp Glu Lys
1               5

<210> SEQ ID NO 80
<211> LENGTH: 12
<212> TYPE: PRT
<213> ORGANISM: Artificial Sequence
<220> FEATURE:
<223> OTHER INFORMATION: Synthetic

<400> SEQUENCE: 80

Ser Tyr Gly Ile Pro Phe Ile Glu Thr Ser Ala Lys
1               5                   10

<210> SEQ ID NO 81
<211> LENGTH: 9
<212> TYPE: PRT
<213> ORGANISM: Artificial Sequence
<220> FEATURE:
<223> OTHER INFORMATION: Synthetic

<400> SEQUENCE: 81

Ser Phe Glu Asp Ile His His Tyr Arg
1               5
```

```
<210> SEQ ID NO 82
<211> LENGTH: 7
<212> TYPE: PRT
<213> ORGANISM: Artificial Sequence
<220> FEATURE:
<223> OTHER INFORMATION: Synthetic

<400> SEQUENCE: 82

Thr Asp Gln Gly Leu Leu Lys
1               5
```